(12) United States Patent
Segal et al.

(10) Patent No.: US 11,946,922 B2
(45) Date of Patent: *Apr. 2, 2024

(54) ADDRESSING INCOMPLETE SOIL SAMPLE DATA IN SOIL ENRICHMENT PROTOCOL PROJECTS

(71) Applicant: Indigo Ag, Inc., Charlestown, MA (US)

(72) Inventors: Brian Segal, Charlestown, MA (US); Charles David Brummitt, Charlestown, MA (US)

(73) Assignee: INDIGO AG, INC., Charlestown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/066,477

(22) Filed: Dec. 15, 2022

(65) Prior Publication Data

US 2023/0147951 A1     May 11, 2023

Related U.S. Application Data

(63) Continuation of application No. 17/724,912, filed on Apr. 20, 2022, now Pat. No. 11,592,431.

(60) Provisional application No. 63/319,629, filed on Mar. 14, 2022, provisional application No. 63/306,284, filed on Feb. 3, 2022, provisional application No. 63/238,541, filed on Aug. 30, 2021, provisional application No. 63/177,376, filed on Apr. 20, 2021.

(51) Int. Cl.
    *G01N 33/24*       (2006.01)
(52) U.S. Cl.
    CPC .................. *G01N 33/24* (2013.01)

(58) Field of Classification Search
    CPC ....................................................... G01N 33/24
    See application file for complete search history.

(56) References Cited

U.S. PATENT DOCUMENTS

7,974,853 B1 * 7/2011 Zimmerman .......... G06Q 10/04
                                                    705/7.11
11,592,431 B2   2/2023 Segal et al.
                        (Continued)

FOREIGN PATENT DOCUMENTS

WO    WO-2022/226023 A1    10/2022

OTHER PUBLICATIONS

Roper et.al., "Comparing Four Methods of Measuring Soil Organic Matter in North Carolina Soils", pp. 466-474 (Year: 2019).*

(Continued)

*Primary Examiner* — Michael J Dalbo
*Assistant Examiner* — Kaleria Knox
(74) *Attorney, Agent, or Firm* — Fenwick & West LLP

(57) ABSTRACT

In various embodiments, methods, systems, and computer program products are provided for estimating greenhouse gas emissions. In particular, methods, systems, and computer program products are presented for the task of quantifying emissions reduction from changes in stocks of soil organic carbon (SOC). The methods apply more generally to tasks that involve quantification of a total or average across a population of land (and/or possibly any space and any time) using measurements at a sample from that population. The sample may not be representative or unbiased. In some examples, estimating greenhouse gas emissions may apply to quantifying the total stock of SOC in land, the total nitrous oxide emissions in land and a time interval.

23 Claims, 34 Drawing Sheets

(56) References Cited

U.S. PATENT DOCUMENTS

| | | | |
|---|---|---|---|
| 2010/0198736 A1 | 8/2010 | Marino | |
| 2013/0197814 A1 | 8/2013 | McBratney et al. | |
| 2017/0286574 A1* | 10/2017 | Chappell | G06F 30/20 |
| 2018/0070527 A1 | 3/2018 | Richt | |
| 2018/0075545 A1 | 3/2018 | Richt | |
| 2019/0335674 A1 | 11/2019 | Basso | |
| 2019/0347836 A1* | 11/2019 | Sangireddy | A01C 21/005 |
| 2020/0027096 A1 | 1/2020 | Cooner | |
| 2020/0068797 A1* | 3/2020 | Folle | G06Q 50/02 |
| 2022/0343229 A1 | 10/2022 | Gruber et al. | |

OTHER PUBLICATIONS

Chabala et.al., "Application of Ordinary Kriging in Mapping Soil Organic Carbon in Zambia", pp. 338-343, Apr. 2017 (Year: 2017).*

Chabala et al., "Application of Ordinary Kriging in Mapping Soil Organic Carbon in Zambia", Pedosphere, 27(2): 338-343, (2017).

Cotching et al., "Land use and management influence on surface soil organic carbon in Tasmania", Soil Research, 2013(51):615-630, (2013).

International Search Report and Written Opinion for Application No. PCT/US2022/025478 dated Aug. 14, 2022.

Jobbagy et al., "The verticle distribution of soil organic carbon and its relation to climate and vegetation", Ecology Society of America, 1210(2): 423-436, (2002).

Roper, "Comparing Four Methods of Measuring Soil Organic Matter in North Carolina Soils", Soil Science Society of America Journal 83: 466-474 (2019).

* cited by examiner

The estimation strategy (and post-stratification) for each pre-stratum.

| | Adjusted? | Population (and post-stratification, if applicable) |
|---|---|---|
| Pre-stratum 1 = {"Stratum A"} | Yes | zone \| post-strat \| area<br>1 \| 1 \| 4<br>2 \| 1 \| 7<br>... \| ... \| ... |
| Pre-stratum 2 = {Stratum "B"} | No | field \| area<br>1 \| 40<br>2 \| 19<br>... \| ... |
| ... | ... | ... |
| Pre-stratum G = {"Stratum D"} | Yes | zone \| post-strat \| area<br>102 \| 1 \| 12<br>103 \| 2 \| 9<br>... \| ... \| ... |

From Fig. 3C → … → To Fig. 3E

The unadjusted analysis for each pre-stratum, so that the result can be compared with the adjusted analysis above

| | Adjusted? | Population |
|---|---|---|
| Pre-stratum 1 = {"Stratum A"} | No | field \| area<br>1 \| 40<br>2 \| 19<br>... \| ... |
| Pre-stratum 2 = {"Stratum B"} | No | field \| area<br>3 \| 40<br>4 \| 19<br>... \| ... |
| ... | ... | ... |
| Pre-stratum G = {"Stratum D"} | No | field \| area<br>5 \| 40<br>6 \| 19<br>... \| ... |

Fig. 3D

| | Mean GHG emission reductions (tons CO2e/ha) | Area of post-stratum (ha) | Total GHG emission reductions (tons CO2e) | Variance of GHG emission reductions |
|---|---|---|---|---|
| Post stratum 1 | 0.3 | 200 | 0.3 × 200 = 60 | 6 |
| Post stratum 2 | 0.35 | 150 | 0.35 × 150 = 52.5 | 5 |
| Post stratum 3 | 0.25 | 300 | 0.25 × 300 = 75 | 7 |
| Project total | | | 60 + 52.5 + 75 = 187.5 | 6 + 5 + 7 = 18 |

Fig. 7D

ADDRESSING INCOMPLETE SOIL SAMPLE DATA IN SOIL ENRICHMENT PROTOCOL PROJECTS

CROSS-REFERENCE TO RELATED APPLICATIONS

This application is a continuation of U.S. application Ser. No. 17/724,912, filed Apr. 20, 2022, now U.S. Pat. No. 11,592,431, which claims the benefit of U.S. Provisional Application No. 63/177,376 filed Apr. 20, 2021, U.S. Provisional Application No. 63/238,541 filed Aug. 30, 2021, U.S. Provisional Application No. 63/306,284 filed Feb. 3, 2022 and U.S. Provisional Application No. 63/319,629 filed Mar. 14, 2022, each of which is hereby incorporated by reference in its entirety.

BACKGROUND

Embodiments of the present disclosure relate to determining carbon credits with incomplete predictions of emissions reduction for a given land region (or, more generally, for estimating global quantities in space or in space and time). When determining carbon credits for land use (e.g., farming of commodities), field-scale data may be thin, satellite data may be unreliable (e.g., low-resolution, variable orbits, etc.) and soil measurements may be unavailable (e.g., fields are temporarily inaccessible due to weather or tall crops; samples were lost or degraded in shipment, etc.), thus resulting in missing data points for greenhouse gas emission reduction. These missing data points can bias the estimates of the total emissions reduction of the whole land region.

Accordingly, there exists a need for a method to assess the potential for bias using data known across the whole region and time period, and to make statistical adjustments to reduce that bias in estimates of greenhouse gas emission reduction.

BRIEF SUMMARY

In various embodiments, a method for estimating greenhouse gas emissions is provided such that bias from missing data is assessed and mitigated. The goal of this method is to quantify reductions in emissions—such as reductions in nitrous oxide, methane, and carbon dioxide in a plurality of tracts of land that grow commodity crops—in such a way that the population-wide estimates are unlikely to be biased toward over-estimating emissions reduction. The method applies to quantification of carbon credits that involves estimating emissions reduction at a subset of the population and estimating the population-wide emissions reduction from that measured subset. For example, in quantifying emissions reduction from changing the way commodity crops are grown, a plurality of soil sample locations within a land area are planned to be sampled, and soil attributes for at least some of the plurality of soil sample locations are measured. Emissions reduction from avoiding emissions and increasing the amount of soil organic carbon (SOC) are estimated using those soil measurements, by measuring the change in carbon stocks over time or by providing the soil measurement results to computer models that predict emissions using those measurements to initialize the computer models. The plurality of sample points where emissions reduction is planned to be estimated may be referred to as the planned points, and the plurality of sample points where emissions reduction is successfully estimated may be referred to as the observed points. Points where emissions reduction was planned to be estimated but where emissions reduction was not estimated may be referred to as missing, and these missing measurements can create bias in the estimates of emissions reduction across the population of land based on estimates at the observed points. Estimates of emissions reduction can be missing at points for a number of reasons; examples include the soil measurement is missing; the soil measurement failed a quality check; the computer model raised an error when processing the soil measurement; etc. The population of land across which emissions reduction is estimated is divided into a plurality of pre-strata, and within each pre-stratum a plurality of sample locations are chosen. For each pre-stratum of the plurality of pre-strata: an assessment of bias is determined for the pre-stratum based on attributes of the observed points and attributes of all planned points. A plurality of post-strata are determined based on the pre-stratum when the indicators of bias are above a predetermined threshold. The plurality of post-strata are disjoint subsets of the population. A total estimated emissions reduction of the land area is determined based on the plurality of post-strata and the estimated emissions reduction of the land area.

In various embodiments, a system is provided including a database describing the geospatial boundaries of a population of land, a database of attributes describing small areas within that population of land, a database of locations where soil samples are planned to be taken in that population of land, a database of locations where soil samples were taken, and a computing node comprising a computer readable storage medium having program instructions embodied therewith. The database of land attributes can involve data at many spatial scales, such as region, county, field, or sub-field scales. Examples of attributes of land in that database include soil attributes (e.g., pH, texture, parent material, soil organic matter, nutrient content, water content, bulk density, etc.), the way the land is managed (e.g., fertilizer application amount and timing, planting rate, crop type, tillage method, tillage depth, etc.), topographic information (e.g., slope, aspect, an indicator of soil wetness based on topography, etc.), and weather (e.g., annual precipitation, mean daily high temperature, etc.). The program instructions are executable by a processor of the computing node to cause the processor to perform a method where a plurality of planned soil sample locations are received from the soil sample location database, and attributes for those planned sample locations are retrieved from the land attribute database by determining which land in the land attribute database the sample location intersects or belongs to. Emissions reduction in the population of land are estimated using the soil measurements taken at the sample locations, such as by using computer models that predict the change in soil organic carbon (SOC) and emissions of methane and nitrous oxide, using the soil measurements as inputs. The population is divided into a plurality of disjoint subsets call pre-strata. Within each pre-stratum of the plurality of pre-strata, the plurality of soil sample locations are chosen using a random selection process. For each pre-stratum of the plurality of pre-strata: an assessment of bias is determined for the pre-stratum; and a plurality of post-strata are determined based on the pre-stratum when the indicator of bias is above a predetermined threshold. The plurality of post-strata are disjoint subsets of the population of land. A total estimated emissions reduction of the population land area is determined based on the plurality of post-strata and the estimated emissions reduction of the land area in the post-strata.

In various embodiments, a method for estimating greenhouse gas emissions is provided where a plurality of soil sample locations within a land area, soil attributes for at least some of the plurality of soil sample locations, and regional soil data of the land area are received. Soil organic carbon (SOC) emissions reduction of the land area are estimated. A plurality of pre-strata are determined based on the plurality of soil sample locations and the regional soil data. Each pre-stratum of the plurality of pre-strata include a plurality of soil sample points across the land area. For each pre-stratum of the plurality of pre-strata: a potential for bias is determined for the pre-stratum; and a plurality of post-strata are determined based on the pre-stratum when the potential for bias is above a predetermined threshold. The plurality of post-strata are disjoint subsets of the pre-stratum. A total estimated emissions reduction of the land area is determined based on the plurality of post-strata and the estimated SOC emissions reduction of the land area.

Estimating SOC emissions reduction may include that a plurality of simulations of SOC emissions reduction are generated based on soil attributes of the land area. The plurality of simulations may include Monte Carlo simulations. The soil attributes may include % SOC, soil texture, pH, and bulk density. The regional soil data may include land management practices. The regional soil data may include soil characteristics. At least two of the plurality of pre-strata may be combined. Determining the plurality of pre-strata may include that a zone attribute table and a point attribute table are applied. Determining the potential for bias may include that a first average value of an attribute among observed sample locations is determined, a second average value of the attribute among all locations where samples were planned to be taken is determined, a pooled standard deviation is determined based on variation associated with the attribute, and the pre-strata is labelled as likely including bias when the difference between the first and second average values, divided by the pooled standard deviation, is above a predetermined threshold. Determining the post-stratum may further include that the land area is partitioned into a plurality of fields, each field comprising one or more soil sample locations of the plurality of soil sample locations, and that the plurality of fields are binned into a plurality of bins based on at least one variable. Determining the post-stratum may further include that one or more rules is applied to the binned plurality of fields. The at least one variable may include land management practices. The at least one variable may include soil texture. The at least one variable may include crop type. Binning may include that clustering is applied to the plurality of fields. Clustering may include k-means clustering. At least one of the plurality of fields may include at least one observed soil measurement at the one or more soil sample locations. At least one of the plurality of fields may include at least one missing soil measurements at the one or more soil sample locations. Determining the total estimated emissions reduction may include that for each post-stratum: a mean emissions reduction is determined based on the at least one observed soil measurement in the plurality of fields within the post-stratum, a total emissions reduction is determined based on the mean emission reduction and a total area of the post-stratum, and a variance of the total emissions reduction is determined. A standardized mean difference may be determined for all attributes that are known across all the planned sample points and are thought to be related to emissions reduction. Determining the total estimated emissions reduction may further include that: each total emissions reduction is summed, and each variance is summed. A potential for bias for each post-stratum in the plurality of post-strata may be determined.

In various embodiments, a system is provided including a soil attribute database, a soil sample location database, a regional soil data database, and a computing node comprising a computer readable storage medium having program instructions embodied therewith. The program instructions are executable by a processor of the computing node to cause the processor to perform a method where a plurality of soil sample locations within a land area are received from the soil sample location database, soil attributes for at least some of the plurality of soil sample locations are received from the soil attribute database, and regional soil data of the land area are received from the regional soil data database. Soil organic carbon (SOC) emissions reduction of the land area are estimated. A plurality of pre-strata are determined based on the plurality of soil sample locations and the regional soil data. Each pre-stratum of the plurality of pre-strata include a plurality of soil sample points across the land area. For each pre-stratum of the plurality of pre-strata: a potential for bias is determined for the pre-stratum; and a plurality of post-strata are determined based on the pre-stratum when the potential for bias is above a predetermined threshold. The plurality of post-strata are disjoint subsets of the pre-stratum. A total estimated emissions reduction of the land area is determined based on the plurality of post-strata and the estimated SOC emissions reduction of the land area.

Estimating SOC emissions reduction may include that a plurality of simulations of SOC emissions reduction are generated based on soil attributes of the land area. The plurality of simulations may include Monte Carlo simulations. The soil attributes may include % SOC, soil texture, pH, and bulk density. The regional soil data may include land management practices. The regional soil data may include soil characteristics. At least two of the plurality of pre-strata may be combined. Determining the plurality of pre-strata may include that a zone attribute table and a point attribute table are applied. Determining the potential for bias may include that an estimated variance of the SOC emissions reduction estimate is determined, a pre-strata variance is determined, a difference between the pre-strata variance to the estimated variance is determined, and the pre-strata is labeled as likely including bias when the difference is above a predetermined threshold. Determining the post-stratum may further include that the land area is partitioned into a plurality of fields, each field comprising one or more soil sample locations of the plurality of soil sample locations, and that the plurality of fields are binned into a plurality of bins based on at least one variable. Determining the post-stratum may further include that one or more rules is applied to the binned plurality of fields. The at least one variable may include land management practices. The at least one variable may include soil texture. The at least one variable may include crop type. Binning may include that clustering is applied to the plurality of fields. Clustering may include k-means clustering. At least one of the plurality of fields may include at least one observed soil measurement at the one or more soil sample locations. At least one of the plurality of fields may include at least one missing soil measurements at the one or more soil sample locations. Determining the total estimated emissions reduction may include that for each post-stratum: a mean emissions reduction is determined based on the at least one observed soil measurement in the plurality of fields within the post-stratum, a post-stratum emissions reduction is determined based on the mean emission reduction and a total area of the post-stratum, and a post-stratum variance of the post-stratum emissions reduction is determined. A standardized mean difference may be determined for all attributes that are known across all the planned sample points and are thought to be related to emissions reduction. Determining the total estimated emissions reduction may further include that: each post-stratum emissions reduction is summed, and each post-stratum variance is summed. A potential for bias for each post-stratum in the plurality of post-strata may be determined.

In various embodiments, a computer program product for estimating greenhouse gas emissions is provided including a computer readable storage medium having program instructions embodied therewith. The program instructions are executable by a processor to cause the processor to perform a method where a plurality of planned points within a land area, attributes for the plurality of soil sample locations, and attributes of the land area are received. Soil organic carbon (SOC) emissions reduction of the land area are estimated. A plurality of pre-strata are determined based on the plurality of soil sample locations and the regional soil data. Each pre-stratum of the plurality of pre-strata include a plurality of soil sample points across the land area. For each pre-stratum of the plurality of pre-strata: a potential for bias is determined for the pre-stratum; and a plurality of post-strata are determined based on the pre-stratum when the potential for bias is above a predetermined threshold. The plurality of post-strata are disjoint subsets of the pre-stratum. A total estimated emissions reduction of the land area is determined based on the plurality of post-strata and the estimated SOC emissions reduction of the land area.

Estimating SOC emissions reduction may include that a plurality of simulations of SOC emissions reduction are generated based on soil attributes of the land area. The plurality of simulations may include Monte Carlo simulations. The soil attributes may include % SOC, soil texture, pH, and bulk density. The regional soil data may include land management practices. The regional soil data may include soil characteristics. At least two of the plurality of pre-strata may be combined. Determining the plurality of pre-strata may include that a zone attribute table and a point attribute table are applied. Determining the potential for bias may include that a first average value of an attribute among observed sample locations is determined, a second average value of the attribute among all locations where samples were planned to be taken is determined, a pooled standard deviation is determined based on variation associated with the attribute, and the pre-strata is labelled as likely including bias when the difference between the first and second average values, divided by the pooled standard deviation, is above a predetermined threshold. Determining the post-stratum may further include that the land area is partitioned into a plurality of fields, each field comprising one or more soil sample locations of the plurality of soil sample locations, and that the plurality of fields are binned into a plurality of bins based on at least one variable. Determining the post-stratum may further include that one or more rules is applied to the binned plurality of fields. The at least one variable may include land management practices. The at least one variable may include soil texture. The at least one variable may include crop type. Binning may include that clustering is applied to the plurality of fields. Clustering may include k-means clustering. At least one of the plurality of fields may include at least one observed soil measurement at the one or more soil sample locations. At least one of the plurality of fields may include at least one missing soil measurements at the one or more soil sample locations. Determining the total estimated emissions reduction may include that for each post-stratum: a mean emissions reduction is determined based on the at least one observed soil measurement in the plurality of fields within the post-stratum, a post-stratum emissions reduction is determined based on the mean emission reduction and a total area of the post-stratum, and a post-stratum variance of the post-stratum emissions reduction is determined. A standardized mean difference may be determined for all attributes that are known across all the planned sample points and are thought to be related to emissions reduction. Determining the total estimated emissions reduction may further include that: each post-stratum emissions reduction is summed, and each post-stratum variance is summed. A potential for bias for each post-stratum in the plurality of post-strata may be determined.

BRIEF DESCRIPTION OF THE SEVERAL VIEWS OF THE DRAWINGS

FIGS. 3A-3F illustrate a flow diagram for estimating greenhouse gas emissions reduction according to embodiments of the present disclosure.

FIGS. 7A-7D illustrate exemplary post-strata grouping and total greenhouse gas emissions reduction according to embodiments of the present disclosure.

DETAILED DESCRIPTION

Figure 1:
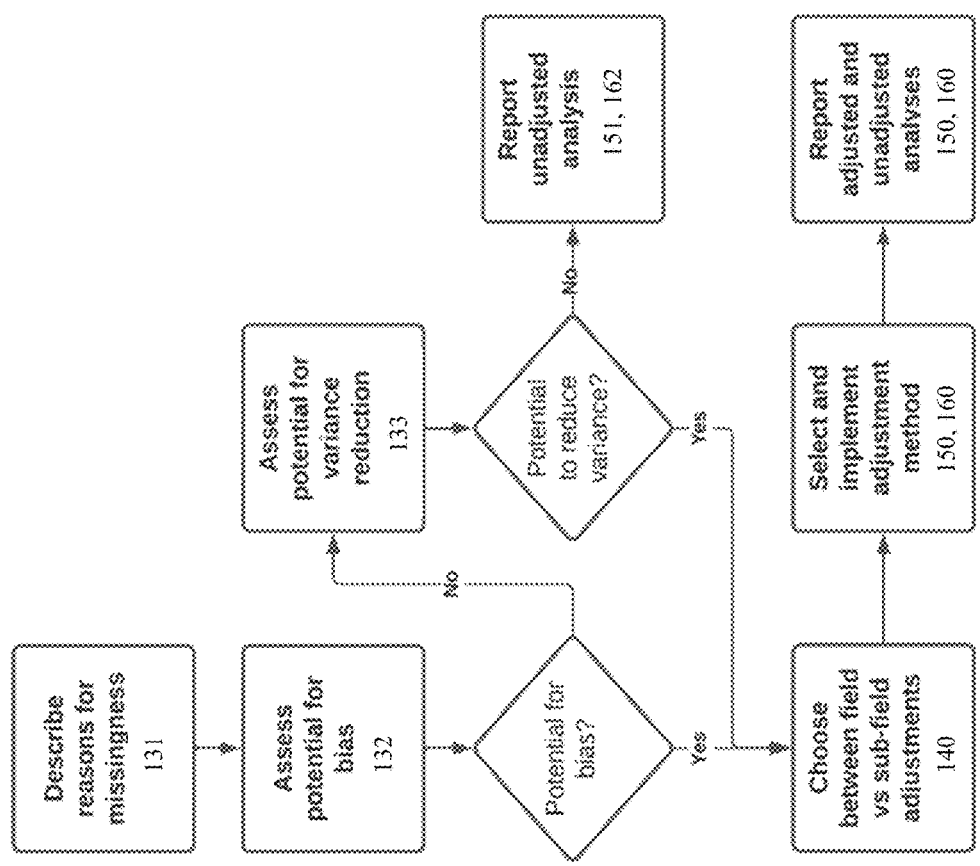
FIG. 1 depicts overall steps and decisions in addressing incomplete soil samples according to embodiments of the present disclosure.

The disclosure herein provides guidance for statistical techniques to reduce bias from missing samples in projects that estimate ecosystem effects, for example carbon offsets.

Adoption of certain farming practices can produce verifiable environmental characteristics. For example, increasing the soil organic carbon and/or reducing greenhouse gas emissions can reduce water usage and can reduce chemical contamination (e.g., reduce nitrogen run-off, reduce insecticide/pesticide/herbicide residue, and the like). These environmental characteristics can be quantified and monetized as ecosystem credits (e.g., a carbon credit equivalent to 1 metric ton of carbon sequestered) under a particular methodology (e.g., a set of requirements). Examples of methodologies can include protocols administered by Climate Action Reserve (CAR) (climateactionreserve.org), the Soil Enrichment Protocol (SEP), methodologies administered by Verra (verra.org), such as the Methodology for Improved Agricultural Land Management, farming sustainability certifications, and other similar programs. One or more participants or groups of participants whose adoption of certain farming practices are quantified, verified and/or tracked for compliance with a methodology may be referred to as a "project." Methodologies can provide guidance on how to account for, report, and verify greenhouse gas (GHG) emission reductions and removals on agricultural lands due to the adoption of sustainable land management practices. For example, GHG emission reductions and removals covered by the SEP include $CO_2$, $N_2O$, and $CH_4$ emission reductions as well as soil organic carbon (SOC) stock change.

While the emission reductions of some sustainable land management practices can be calculated with default equations (e.g., reduced CO2 and N2O emissions due to reduced biomass burning), others can be predicted with biogeochemical models (e.g., increased SOC stocks due to adoption of cover crops and no-till practices). Soil attributes at the project initiation—such as carbon concentration (% SOC), pH, texture, and bulk density—are key inputs to these biogeochemical models. For this reason, soil attributes may be directly measured at the initiation of an SEP project, as well as at least every five years thereafter, as described in various embodiments herein. These directly measured soil attributes can be used as input to biogeochemical models, which are then used to predict GHG emissions and SOC levels under two scenarios:

Baseline scenario: Assuming growers had not adopted new sustainable land management practices Project scenario: Accounting for the additional sustainable land management practices that growers adopted due to the project The GHG emission reductions and removals are then estimated as the difference in emissions and SOC stock between the project and baseline scenarios.

The soil measurements may and sometimes must be taken at randomly selected locations (points) according to a sample design with the aim of collecting a representative sample of soils. The biogeochemical models make projections under the above scenarios at each sampled point. However, it may not be possible to collect and analyze soil from all selected points due either to reasons that may be associated with soil attributes (e.g., frozen soil or localized flooding), or reasons that are likely unassociated with soil attributes (e.g., equipment failure, lost sample labels, laboratory mishap). These missing points represent survey nonresponse. As a first step to addressing survey nonresponse, all possible attempts should be made to collect data from the selected points in follow-up efforts. However, due to resource and logistical constraints, physical barriers (e.g., irrigation equipment below the surface at selected points), or other challenges, some samples may remain missing despite best efforts to collect and analyze them. The missing points could represent entire fields or portions of fields.

If the nonresponse is due to reasons unrelated to the soil attributes used as inputs to the biogeochemical models (and thus independent of estimated GHG emission reductions and removals), then the nonresponse would not cause bias. However, if nonresponse is correlated with emission reductions and removals, then a naive analysis of the observed data could lead to biased estimates because points with high or low emission reductions might be over- or under-represented in the sample.

The distinction of when nonresponse does and does not cause bias is related to common classifications of missing data. In particular, when soil samples are missing completely at random (MCAR), then by definition nonresponse cannot be related to field attributes and there is no concern for bias. In contrast, if the soil samples are missing at random (MAR) or missing not at random (MNAR), then nonresponse could cause bias if the missingness is associated with emission reductions or removals. Said another way, MCAR is a sufficient but not necessary condition for ensuring a lack of bias in the presence of nonresponse; a lack of association between missingness and the outcome is a necessary condition.

The disclosure herein provides guidance on analytic approaches for addressing missing soil samples in one or more projects, with the aim of mitigating potential bias and reducing variance. Before making any analytic adjustments to address missing data, all reasonable attempts should be made to collect and analyze samples at all selected points.

Balancing Completeness, Timeliness, and Uncertainty

In large projects comprising thousands of growers and many times that many fields (sometimes referred to as "aggregated projects"), completing a sample may take years because opportunities for sampling are brief and spaced months apart. For example, a field may be available for sampling during a two-week period after harvest of a cash crop and before the subsequent cover crop is too tall for sampling crews to navigate it; if one misses that window, one may wait six months for another opportunity to sample the field. Insisting on a complete sample jeopardizes the ability of such projects to issue credits in a timely manner. Meanwhile, insisting on smaller sample sizes (that are more likely to be completed) results in intolerably high uncertainty. The optimum lies between these extremes: choose a sample size that is large yet plausible to complete, and use the techniques described herein to minimize bias from a relatively small fraction of missing data.

Background on Soil Samples and Sample Points in Projects

In some projects, a sample design selects points at which to take multiple samples of soil for various measurements. Some methodologies such as the SEP may require that project developers measure the concentration of soil organic carbon (abbreviated % SOC) and bulk density in their project, as described in various embodiments herein. Other soil measurements, such as texture and pH, can be taken if desired (for example, to improve accuracy of biogeochemical model predictions).

Different equipment is used for these measurements. As a result, some or all samples may be missing at a point. For example, bulk density cores are particularly prone to breaking due to the amount of force applied, resulting in some points having a % SOC measurement but missing a bulk density measurement.

The main focus is on the missingness of % SOC measurements (because they vary significantly in space and are a key variable that many projects aim to influence). Thus, a sample point is missing if its % SOC measurement is missing. Because of the importance of % SOC measurements, it is recommended that it be measured at every point chosen by the sample design.

The disclosure herein also covers missingness of bulk density, texture, and pH measurements. Projects may take these measurements at a random subset of points where % SOC is measured because the former measurements are expensive to take, lead to more injuries to soil samplers (in the case of bulk density), and/or vary less within fields than % SOC does. At points where these measurements were missing—either deliberately so (to reduce costs) or due to unforeseen challenges (e.g., sample lost in shipment; part of a field was flooded)—they can be imputed using models, subject to the requirements, as described in various embodiments herein.

FIG. 1 shows the overall steps and decisions for addressing incomplete soil samples after all reasonable attempts have been made to collect and analyze missing samples. The process in FIG. 1 begins with a description of why samples were missing and an assessment of whether the missing samples could potentially cause bias (as described in more detail below). If these investigations conclude that there is potential for bias, then statistical adjustments may be made at either the field or sub-field level (140, described further below) with approved statistical methods (150, 160, described further below) to minimize potential bias. In addition to the adjusted estimates of GHG emission reductions/removals, an unadjusted analysis (151, 162, described further below) may be reported for comparison.

If the investigations do not raise concerns for potential bias, then an unadjusted analysis may be required (the variance may also reflect the observed sample size; see, e.g., Equation (4)). However, a statistical adjustment method may also be conducted with the aim of reducing variance (133, described further below).

Investigating Missing Soil Samples

Describing Reasons for Missing Soil Samples (131)

The reason that each planned soil sample is missing (for all types of samples: % SOC, bulk density, pH, and texture) should be tabulated and categorized as to whether or not it is related to field attributes associated with emission reductions and removals, and thus a potential concern for bias. Table 1 provides an example, though the most relevant categorization of reasons for missingness may vary across projects. However, in all cases the reasons should be grouped into those that are potentially concerning (related to field attributes) and those that are not concerning (unrelated to field attributes). In rare cases, it may not be known why a sample is missing, in which case the reason should be categorized as "Unknown."

TABLE 1

Reasons why planned soil samples are missing (example template)

| | Count (% of total planned samples) | | |
|---|---|---|---|
| Reason for missingness | % SOC | Bulk density | Texture and pH |
| Potentially concerning (related to field attributes) | | | |
| Seasonal delay | n (%) | n (%) | n (%) |
| Short-term weather delay | n (%) | n (%) | n (%) |
| Crop already established | n (%) | n (%) | n (%) |
| Livestock in area temporarily | n (%) | n (%) | n (%) |
| Unknown | n (%) | n (%) | n (%) |
| Not concerning (unrelated to field attributes) | | | |
| Field equipment failure (unrelated to the soil) | n (%) | n (%) | n (%) |
| Inadvertently missed by field staff | n (%) | n (%) | n (%) |
| Laboratory error | n (%) | n (%) | n (%) |

In addition, details should be provided for each missing soil sample, including:

1. The date at which the problem occurred or was reported
2. A 1-2 sentence description of the problem, and
3. An overall categorization to cross-reference the reasons for missingness in Table 1.

As an example, the 1-2 sentence descriptions might be along the lines of "Sample tested positive for excess lime, but results were reported as total carbon percent. Lab could not guarantee that samples received acid pre-treatment," or "Sample could not be taken due to localized flooding."

Verifiers are encouraged to use the information in Table 1, and the more detailed information about individual soil samples, to understand the causes of missing soil measurements and to better interpret the adjustments made to address them.

Assessing Implications for Bias (132)

To assess whether the potentially concerning missing % SOC samples might be associated with GHG emission reductions and removals, the marginal distributions of factors associated with emission reductions and removals should be compared between points with missing and observed % SOC, such as in Table 2. Table 2 is an example, and the exact attributes and categorizations of attributes may vary across projects. Additional guidance is provided below on alternative attributes that may be included in Table 2.

TABLE 2

Attributes of sample points with all and observed % SOC. For categorical variables such as the binned total precipitation, the n values in a column sum to the number of such samples (all or observed). For continuous variables such as SSURGO % SOC, the mean and standard deviation are provided.

| Attribute | All (n) | Observed (n) | Standardized difference |
|---|---|---|---|
| Land Resource Region | | | d |
| F | n (%) | n (%) | |
| K | n (%) | n (%) | |
| M | n (%) | n (%) | |
| Total precipitation | | | d |
| <10 inches | n (%) | n (%) | |
| 10-15 inches | n (%) | n (%) | |
| 15-20 inches | n (%) | n (%) | |
| SSURGO clay content | | | d |
| <10 inches | n (%) | n (%) | |
| 10-15 inches | n (%) | n (%) | |
| 15-20 inches | n (%) | n (%) | |
| SSURGO % SOC | mean (sd) | mean (sd) | d |
| Practice management change | | | d |
| Conventional tillage to no-till | n (%) | n (%) | |
| Conventional tillage to reduced tillage | n (%) | n (%) | |
| Began manure application | n (%) | n (%) | |
| Began returning residue | n (%) | n (%) | |
| Corn/soy rotation to corn/wheat | n (%) | n (%) | |

The standardized difference (also referred to as standardized mean difference, abbreviated "SMD") between i.) all points in the planned sample and ii) points with observed % SOC should be calculated for all attributes in Table 2. For example, let $p_{all,kl}$ an $p_{obs,kl}$ be the proportion of points in category 1 for attribute k among all points in the planned sample and observed points, respectively. The proportions sum to 1 within an attribute ($\Sigma_l p_{all,kl}=1$ and $\Sigma_l p_{obs,kl}=1$). The standardized difference is defined for a dichotomous attribute as:

$$d_k = \frac{p_{obs,k2} - p_{all,k2}}{p_{all,k2}(1 - p_{all,k2})} \quad (1)$$

which scales the difference in proportions by the pooled standard deviation.

The standardized difference for continues variables with means $\bar{x}_{1k}$ and $\bar{x}_{2k}$ is $$d_k = (\bar{x}_{obs,k} - \bar{x}_{all,k})/S_{all} \quad (2)$$

where $s_{all}$ is the pooled standard deviation. Equation (2) should be used for any continuous variables in Table 2 that are not categorized.

The set of all points is a probability sample from the target population, but emission reductions can, at times only, be estimated at points with observed % SOC. Therefore, it is desirable to compare the distribution of field attributes between i) all points in the planned sample, and ii) points with observed % SOC. This will help to determine whether emission reductions estimated with group (ii) might be biased for emission reductions in group (i). If some land had zero chance of having sample locations chosen in it (e.g., because the land was added to the population after a random selection of sample locations was chosen), the potential for bias resulting from that land having zero chance of being sampled can be assessed by assigning new synthetic sample locations to that land; those synthetic points will appear in the list i) of all planned points and not in the list ii) of observed points. For example, the number of synthetic points could be determined by using the same spatial density used elsewhere in the pre-stratum that the land would have belonged to (had the land been included at the time when sample points were originally chosen); then the locations of those synthetic points could be chosen using a simple random sample.

If $|d_k| \leq 0.1$ for all attributes k, then there may be minimal or no concern for bias. The threshold of 0.1 is commonly used in observational medical and behavioral studies, though a threshold of 0.25 is also used in some scientific fields. Statistical hypothesis tests and p-values should not be used to assess whether there is a concern for bias, because p-values are a function of sample size (e.g., for large sample sizes, the point null hypothesis of no difference may be rejected even if the magnitude of the difference is too small to cause a concern for bias).

The standardized differences should be recomputed after making adjustments to assess how well the adjustment reduced concern for potential bias. For example, if post-stratification is used, the standardized differences should be recomputed within each post-stratum. If the post-stratified standardized differences are not all less than 0.1 in magnitude, then changes can be made to the post-stratification (e.g., splitting post-strata into multiple post-strata) to further reduce imbalance, though the post-strata sample size requirements described below may still be met. As long as the decision on whether to change the post-strata are based on the standardized differences and not on estimated GHG emission reductions/removals, there is no concern for cherry-picking results. This recommendation is in line with common practice in observational research for selecting matches that achieve covariate balance.

The standardized difference d k assesses differences in marginal distributions, so there may be differences in joint distributions that go undetected. In addition, for attributes with many categories, the counts in each category may be small (e.g., less than 10 sample points) leading to unstable estimates.

The limitations and context noted above, together with the reasons for missingness in Table 1, should be taken into account when assessing the standardized differences and determining whether the concerning missing soil samples could potentially cause bias. The reasoning and conclusion may be documented and address all of the points above.

Other descriptive summaries that may be considered but which are not required include:

- A choropleth map showing the location of all fields in the project, with coloring or shading to indicate the proportion of sample points that are missing
- A histogram showing the distribution of sampling proportions within fields
- A scatter plot comparing field acreage and proportion sampled Note that for dichotomous variables, the absolute value of the standardized difference between the proportions in category $l=1$ is identical to that between the proportions in category $l=2$ because $p_{1k1}=1-p_{1k2}$ and $p_{2k1}=1-p_{2k2}$. Therefore one standardized difference d may only be reported per attribute.

Assessing Potential for Variance Reduction (133)

If there is minimal to no potential for bias, then the analysis can focus on reducing variance. In particular, post-stratification can reduce variance if GHG emission reductions/removals are homogeneous within post-strata. To assess the potential for using post-stratification to reduce variance, the overall distribution of outcomes can be visually inspected, such as with a histogram for each GHG emission reduction/removal. A very tight distribution may indicate lower potential for identifying post-strata with greater within-stratum homogeneity than in the full sample. Conversely, a very spread out distribution may indicate greater potential to identify post-strata with greater within-stratum homogeneity, though this is not guaranteed. In addition to visually inspecting outcome distributions, summary statistics such as the standard deviation can be calculated overall and within groups. All visuals and statistics should be discussed with agronomists, soil scientists, and other domain experts. The rationale for any decisions related to the potential to reduce variance, as well as all visuals and statistics used to support this decision, may be documented.

Guidelines for variance reduction when post-stratifying are provided below to prevent post-strata from being too small or too sparsely sampled.

Determining Whether to Make Adjustments at the Field or Sub-Field Level (140)

The statistical adjustment methods described below can be applied at both the field and sub-field levels. For example, post-stratification could group together similar fields or similar sub-field areas. In the latter approach, the sub-field areas grouped together in a single post-stratum would not necessarily belong to the same field. For example, if two nearby fields both have a portion that is predominantly loam and another portion that is sandy loam, then post-stratification at the sub-field level might combine the loam portions of each field into one post-stratum and the sandy loam portions of each field into another post-stratum. While not currently recommended, calibration and multilevel modeling with post-stratification can also be implemented at both the field and sub-field levels.

Table 3 provides a list of topics and considerations relevant for deciding between field level and sub-field level nonresponse adjustments. For a particular project, the topics and considerations in Table 3 should be taken into account when selecting an approach. Table 3 is not necessarily exhaustive, and there may be other relevant topics and considerations for any given project.

TABLE 3

Topics and considerations for deciding between nonresponse adjustments at the field versus sub-field level

| Topic | Considerations |
| --- | --- |
| Geographic boundaries | It may be more challenging to identify reliable boundaries for sub-field areas than for entire fields. |
| Within-field variation in soil attributes | If fields are heterogeneous with respect to soil attributes such as % SOC, bulk density, soil texture, and pH, then making adjustments at the sub-field level will lead to more homogeneous groups, which can result in greater variance reduction for some methods such as post-stratification. |
| Variance estimation | In sampling designs, it is typical for fields to be the primary sampling unit. In these sampling designs, the estimation of variance may be more complex when forming post-strata at the sub-field level. However, bootstrap or jackknife methods may be used in these situations where resampling is done at the primary unit level (see Examples 4 and 10) |
| Computational demand | It may be less computationally intensive to adjust for non-response at the field level, both for the reason noted above regarding the use of bootstrap and jackknife methods, and because field-level data may be represented with fewer rows. |

Figure 2:
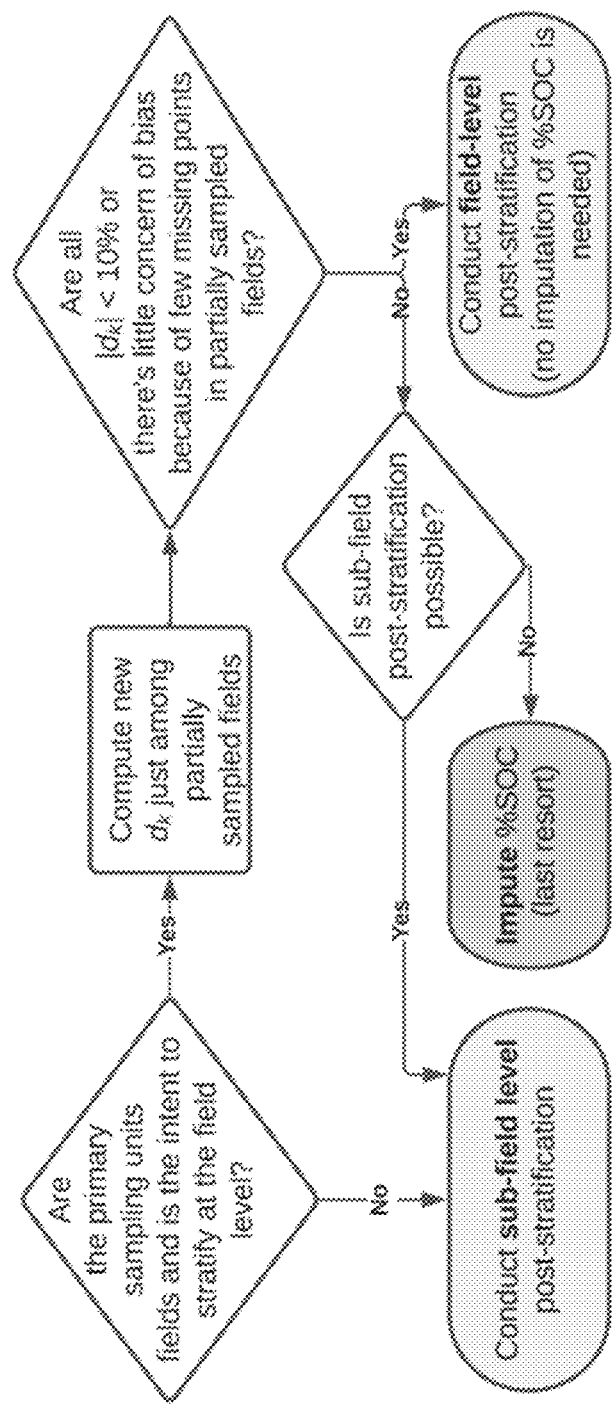
FIG. 2 depicts a flow diagram for deciding whether to impute SOC concentration values to handle bias in partially-sampled fields when post-stratifying at the field level for sampling designs in which fields are the primary units according to embodiments of the present disclosure.

Addressing Missingness in Partially Sampled Fields if Post-Stratifying at the Field Level Some fields are partially sampled, meaning that some of the SOC concentration measurements are taken, but others are missing. When post-stratifying at the field level in sampling designs for which fields are the primary sampling units, one should check whether missingness within fields is associated with emission reductions/removals. This association may be hard to assess given the small number of points within field. (Ideally, a Table 2 would be made for each field.) Here, a workaround is given, depicted in the flow diagram in FIG. 2.

The first step is to pool information among partially-sampled fields to compute new standardized differences, denoted as $d_k^{partial}$, using just the partially-sampled fields. If in the partially-sampled $|d_k^{partial}| \leq 0.1$ for all attributes k and categories E, then field-level post-stratification can proceed without further adjustments because the estimated averages in each field appear to be unbiased.

If, however, are not all less than 10%, then simply post-stratifying at the field level may not suffice to eliminate concern for bias. In this case, it is recommended to post-stratify at the sub-field level (see, e.g., Examples 4 and 10). If, however, post-stratifying at the sub-field level is infeasible (e.g., because it is difficult to obtain data that vary at sub-field levels), then one may, as a last resort, impute SOC concentration values according to the guidelines described below. The decision of whether to make adjustments at the field versus sub-field level may be documented in a written report and address, at a minimum, all of the topics and considerations in Table 3.

Combining points across all partially sampled fields (separately for observed and missing points) could potentially mask within-field differences. For example, one field might be missing points due to localized flooding in a lowland portion, and another field might be missing points due to cattle grazing in a highland portion. In aggregate across the two fields, the proportion of missing points in lowland areas might seem similar to the proportion of observed points in lowland areas, but within each field the proportions might not be similar. This should be considered as a potential limitation when interpreting results.

Selecting and Implementing a Statistical Adjustment Method (150)

This section describes statistical methods that can be used to estimate total GHG emission reductions/removals and variance about the total. All examples are presented in terms of totals, but it is straightforward to alter the formulas to estimate areal means and associated variances. The decision and rationale for the selected method should be documented.

The estimators in Examples 1 through 5 of this section are applicable when GHG emission reductions/removals are predicted with biogeochemical models for which calibration is not necessary. This assumption simplifies the calculations and presentation, though in practice biogeochemical models typically need to go through a calibration process before being used in a project. While necessary for minimizing bias, the calibration process can introduce additional uncertainty that may be accounted for. Examples of how to extend the estimators in the current section to projects that use Bayesian-calibrated biogeochemical models are provided below in the section titled Statistical adjustment methods using predictions from Bayesian calibrated models (160).

Unadjusted Analysis (151)

As described above, an unadjusted analysis may always be required for comparison to adjusted analyses. An unadjusted analysis may also be provided as the sole analysis if there is no concern over potential nonresponse bias as discussed above.

In an unadjusted analysis, the observed data are analyzed as though there were no missing data. The exact calculations will depend on the sampling design, though examples are provided below.

Example 1: Unadjusted Analysis of a Two-Stage Sampling Design where Fields are Selected with Probability Proportional to Size (PPSWR) and Points are Selected with a Simple Random Sample with Replacement (SRSWR)

Let $y_{ij}$ be the GHG emission reduction/removal at point j in field $i=1, \ldots, N$. In the first stage, $n^{plan}$ an field selections are made with PPSWR, and in the second stage an SRSWR of $m^{plan}$ points are drawn from each field selection. If field i is selected $k_i$ times in the first stage, there would be $k_i \times m^{plan}$ points from field i in the sample. If no data were missing, there would be $n^{plan} \times m^{plan}$ samples.

Let n be the observed number of field selections with partial or full sampling information; let $m_i$ be the observed number of samples in field selection i; and let $\bar{y}_i = m_i^{-1} \Sigma_{j=1}^{m_i} y_{ij}$ be the observed mean in field selection i. Also, let $A_i$ be the area of the field i, and let $A = \Sigma_{i=1}^{N} A_i$ be the total area of the project. Because the estimated total in each field is $A_i \bar{y}_i$ and at each draw field i is selected with probability $p_i = A_i/A$, the Hansen-Hurwitz estimator of the total is $$\hat{T} = \frac{1}{n} \sum_{i=1}^{n} \frac{A_i}{p_i} \bar{y}_i = \frac{A}{n} \sum_{i=1}^{n} \bar{y}_i = \sum_{i=1}^{n} \sum_{j=1}^{m_i} w_i y_{ij} \qquad (3)$$

where the weights are $w_i = A/(nm_i)$. The estimator of variance is $$\widehat{Var}(\hat{T}) = \frac{A^2}{n} s^2 \qquad (4)$$

Where $$s^2 = \frac{1}{n-1} \sum_{i=1}^{n} (\bar{y}_i - \hat{\mu})^2 \qquad (5)$$

and $\hat{\mu} = \hat{T}/A$ is the Hansen-Hurwitz estimator of the areal mean. To estimate the variance for the areal mean $\hat{\mu}$ the variance (4) would be divided by $A^2$.

Example 2: Extension of Example 1 when Sampling is Proportional to Estimated Size Building on Example 1, now suppose that in the first stage of the design, sampling was done with probability proportional to estimated areas with replacement. This situation can arise, for example, when field boundaries are corrected after randomization due to on-site observations. Let $\hat{A}_i$, $i=1, \ldots, N$ be the estimated areas of fields, i.e., the known areas of fields at the time of randomization based on their digital boundaries at the time; these $\hat{A}_i$ are estimates of the fields' final areas $A_i$ after corrections are made. Let $\hat{A} = \Sigma_{i=1}^{N} \hat{A}_i$ be the total estimated area. In this design, the sampling probabilities are $p_i = \hat{A}_i/\hat{A}$, which leads to the following estimator for the total:

$$\hat{T} = \frac{1}{n} \sum_{i=1}^{n} \frac{A_i}{p_i} \bar{y}_i = \frac{\hat{A}}{n} \sum_{i=1}^{n} \frac{A_i}{\hat{A}_i} \bar{y}_i = \sum_{i=1}^{n} \sum_{j=1}^{m_i} w_i y_{ij} \qquad (6)$$

where the weights are $w_i = (\hat{A} A_i)/(\hat{A}_i n m_i)$

The estimator of variance is $$\widehat{Var}(\hat{T}) = \frac{\hat{A}^2}{n} s^2 \qquad (7)$$

where

-continued $$s^2 = \frac{1}{n-1}\sum_{i=1}^{n}\left(\frac{A_i}{\hat{A}_i}\overline{y}_i - \hat{\mu}\right)^2 \quad (8)$$

and $\hat{\mu}=\hat{T}/A$ is the Hansen-Hurwitz estimator of the areal mean. As in Example 1, to estimate the variance for the areal mean $\hat{\mu}$, the variance (4) would be divided by $A^2$. As expected, Equations (6), (7), and (8) simplify to Equations (3), (4), and (5), respectively, when $\hat{A}_i = \hat{A}_i$ for all i=1, . . . , N.

Post-Stratification

Post-stratification uses auxiliary variables to group units (either fields or sub-field areas) into mutually exclusive strata, or cells, after the sample has been designed. For example, one post-stratum might consist of all fields in Land Resource Region 'M' that: i) are predominantly loam, and ii) changed from conventional tillage to no-till. Mean emission reductions and removals are estimated within each post-stratum separately. Each post-stratum's mean estimate is multiplied by the post-stratum's area to estimate the post-stratum total emission reductions and removals, and these post-stratum totals are then summed across all post-strata to estimate the total emission reductions for the project.

Post-stratification is closely related to nonresponse weighting. Whereas post-stratification reweights the observed soil samples to be representative of the population (here, all land in the project), nonresponse weighting reweights the observed soil samples to be representative of the planned sample. When the sample is representative of the population, these two weighting approaches will lead to nearly identical results, though the population quantities are of primary interest.

In some contexts, the term post-stratification is reserved for situations where there are no missing data and the term population-based adjustment cell weighting or population weighting adjustment is used in the presence of nonresponse. However, the calculations are the same in both situations.

Post-Stratification Variables

Appropriately selecting the post-stratification variables is critical for achieving the goals of minimizing potential nonresponse bias and reducing variance. Nonresponse bias can be removed by forming post-strata within which emission reductions/removals are independent of the propensity for soil samples to be missing. In particular, these goals can be achieved by forming post-strata within which one or both of the following hold: i) GHG emission reductions/removals are homogeneous, and/or ii) the probabilities of response are homogeneous. While both approaches control non-response bias, post-strata that are homogeneous with respect to outcomes also reduce variance, and there is concern that post-strata that are homogeneous with respect to response probabilities but not emission reductions/removals can increase variance.

This insight leads to the following key points: To minimize nonresponse bias and variance, post-stratification variables should be highly associated with GHG emission reductions/removals. If possible, the post-stratification variables should also be highly associated with response probabilities. These variables may differ across different types of emission reductions/removals due to differences in the underlying biogeochemical processes.

Based on the key points above, Table 4 provides example variables that may be important to consider for SOC emission reductions/removals. Other variables may be relevant for other types of emission reductions/removals. In practice, continuous variables such as total annual precipitation may need to be categorized before using them to form post-strata. Table 4 is not necessarily exhaustive. For any given project, the selection of the most relevant variables, as well as the most appropriate categorization of continuous variables, should be chosen through discussions with agronomists, soil scientists, and other domain experts, and the rationale may be fully documented.

TABLE 4

Examples of candidate post-stratification variables for SOC emission reductions/removals Variable
Region
Land Resource Region
Weather (e.g., from North American Land Data Assimilation System (NLDAS))
Total precipitation during reporting period
Average temperature during reporting period
Soil attributes (e.g., from SSURGO or POLARIS)
SOC concentration
Texture, particularly clay content
Change in management practice
Conventional tillage to no-till
Conventional tillage to reduced tillage
Began manure application
Began retaining residue
Corn/soy rotation to corn/wheat Post-Strata Sample Size While post-stratification can reduce variance by forming homogeneous groups, post-strata that are too small can increase variance. There are different recommendations on minimum post-strata sample size. For example, for general surveys some literature recommends more than 20 observations in each post-stratum, and for forestry studies some literature recommends at least 25 within each post-stratum to avoid bias in the standard error in proportion forestland analyses. Based on these recommendations:

Projects that employ a sampling design in which points are the primary sampling units should have at least 25 point selections in each post-stratum.

Projects that employ a sampling design in which fields are the primary sampling units and which post-stratify at the field level should have a minimum of 25 field selections in each post-stratum.

Projects that employ a sampling design in which fields are the primary sampling units and which post-stratify at the sub-field level may and sometimes must:

Have at least 25 point selections in each post-stratum, and

Have a sufficient number of fields appearing in each post-stratum so that no more than 30% of bootstrap resamples are rejected (see Examples 4 and 10).

If the above criteria are not met, then the post-strata should be changed, such as by collapsing two post-strata into one as described, as described in various embodiments herein.

Collapsing Post-Strata

When a post-stratum is deemed too small, it is common to collapse/pool the post-stratum with other post-strata. Collapsing should be done among post-strata that are as similar as possible with respect to their distributions of field attributes. All decisions and rationale to collapse post-strata may be documented.

Alternative Approaches for Forming Post-Strata

As an alternative to collapsing post-strata, it is possible to form post-strata from quantiles of the response propensity, predicted mean, or a combination of the two (as described next). The response propensity can be estimated by regressing a response indicator on the post-stratification variables, and the predicted mean can be estimated by regressing the emission reductions and removals on the post-stratification variables. When post-stratifying at the field level, the response indicator designates whether the entire field was missing. When post-stratifying at the sub-field level, the response indicator designates whether the point was missing. When post-stratifying at the field level, the emission reductions/removals are the mean for the field. When post-stratifying at the sub-field level, the emission reductions/removals are for the individual point. Post-strata can then be formed from quintiles (or other quantiles) of i) the response propensity, ii) the predicted mean, or iii) the cross-classification of quantiles of the response propensity and quantiles of the predicted mean. Forming post-strata from the response propensity controls nonresponse bias but not variance. In contrast, forming post-strata from the predicted mean controls both nonresponse bias and variance, but may require a separate model for each outcome variable (i.e., each type of emission reduction and removal).

Logistic regression can be used to estimate response propensities, though other methods such as a random forest or gradient boosted trees can also be used. Linear regression can be used to estimate the predicted mean, though modeling assumptions should be verified with common modeling diagnostics. If linear regression does not fit the data well as determined by model diagnostics, then generalized linear models may be explored as another modeling option.

If either response propensity and/or expected mean stratification is used, all decisions, modeling choices, and rationale may be documented.

While post-stratifying on the response propensity and/or predicted mean can reduce the number of post-strata, it can also make it difficult to discern which fields or sub-fields are grouped together. Therefore, if this approach is taken, descriptive summaries of the post-strata may be provided, including:

Maps showing the boundaries of all post-strata
A table showing marginal distribution of the same post-stratum attributes shown in Table 2
Potential Changes in Post-Strata Over Time This document considers the task of estimating a project's total emission reduction in one period of time. Many projects report emission reductions on some cadence, such as annually. Project-wide emission reductions are estimated separately for each time period.

In estimates for subsequent periods of time, growers may adopt new practices that further enhance their sequestration and abatement of emissions, and weather may change substantially. To accommodate these changes, the set of post-stratification variables and the assignment of land to post-strata may change from one time period to the next.

Statistical Estimators of Totals and Variances

This section covers the statistical estimators of the total GHG emission reduction and removal, as well as the variance, conditional on a selected post-stratification. The specific approach will depend on the project's sampling design and the level at which units are post-stratified. In this section, few examples are provided for common sampling schemes, though others are possible.

Example 3: Post-Stratification at the Field Level in a Two-Stage Sampling Design where Primary Units Fields) are Selected with PPSWR and Secondary Units (Points) are Selected by an SRSWR In the first stage, $n^{plan}$ field selections are made with probability proportional to size with replacement (PPSWR), and in the second stage a simple random sample with replacement (SRSWR) of $m^{plan}$ points is drawn from each field selection. If field i is selected $k_i$ times in the first stage, there would be $k_i \times m^{plan}$ selected points for soil samples from field i. If no data were missing, there would be $n^{plan} \times m^{plan}$ samples.

Suppose H post-strata are formed at the field level with areas $A_h$, $h=1, \ldots, H$. Let $n_h$ be the observed number of field selections in post-stratum h with full or partial soil samples, and let $m_{hi}$ be the observed number of sampled points in field i of post-stratum h. Note that due to nonresponse, the total observed number of soil samples may be less than originally planned, i.e., $\Sigma_{h=1}^{H} y_{ij} \Sigma_{i=1}^{n_h} m_{hi} \leq n^{plan} m^{plan}$. Let $y_{hij}$ be the GHG emission reductions/removals at point j in field i of post-stratum h, let $\bar{y}_{hi}$ be the average over the observed points in field i, and let $\hat{y}_h$ be the average over the observed field selections in post-stratum h. The post-stratified estimator of the total is $$\hat{T}_{ps} = \sum_{h=1}^{H} A_h \bar{y}_h = \sum_{h=1}^{H} \left( \frac{A_h}{n_h} \sum_{i=1}^{n_h} \bar{y}_{hi} \right) = \sum_{h=1}^{H} \sum_{i=1}^{n_h} \sum_{j=1}^{m_{hi}} w_{hi} y_{hij} \qquad (9)$$

where the weights are $w_{hi} = A_h / (n_h m_{hi})$.

To estimate the variance, it is typically recommended to condition on the sizes of the post-strata, which leads to the same calculation as when the strata are specified before sampling:

$$\widehat{\text{Var}}(\hat{T}_{ps}) = \sum_{h=1}^{H} \frac{A_h^2}{n_h} s_h^2 \qquad (10)$$

where $$s_h^2 = \frac{1}{n_h - 1} \sum_{i=1}^{n_h} (\bar{y}_{hi} - \bar{y}_h)^2. \qquad (11)$$

Example 4: Continuation of Example 3 when Post-Stratifying at the Sub-Field Level This is a continuation of Example 3, though now suppose that post-strata are formed at the sub-field level. In this case, the total could be estimated as $$\hat{T}_{ps} = \sum_{h=1}^{H} A_h \bar{y}_h \qquad (12)$$

where $\bar{y}_h$ is the unweighted mean of the $n_h$ points in post-stratum h.

The estimate of variance is not straightforward because the primary sampling units are fields, but fields can be split across different post-strata. While a closed-form variance estimator may not exist in this situation, it is possible to obtain bootstrap or jackknife estimates of the variance. When conducting bootstrap or jackknife resampling, the units for resampling should be the primary units (fields) to mimic the original sample design, as these are the largest independent units (ultimate clusters).

For example, with bootstrap resampling, for each of $b=1, \ldots, B$ resamples, a sample of n of the observed field selections would be resampled with replacement to form the $b^{th}$ bootstrap resample. For each bootstrap resample, the within-strata means would be calculated, denoted as $\bar{y}_h^{(b)}$.

In a first bootstrap estimator, let yh=$B^{-1}\Sigma_{h=1}^{H}\bar{y}_h^{(b)}$ be the mean of the bootstrap resamples in stratum h. The bootstrap estimator of the variance of the estimated areal mean within stratum h is $$v_{boot,h} = \frac{1}{1-B}\sum_{b=1}^{B}(\bar{y}_h^{(b)} - \bar{y}_h)^2 \quad (13)$$

and the variance of (12) can be estimated as $$\widehat{\text{Var}}(\hat{T}_{ps}) = \sum_{h=1}^{H} A_h^2 v_{boot,h} \quad (14)$$

Note that $v_{boot,h}$ is the estimated variance of the mean, not of the sample points (i.e. $v_{boot,h}^{1/2}$ is the standard error, not the standard deviation), so division by $n_h$ is not necessary in (14).

In a second bootstrap estimator, let $$\hat{t}_{ps}^{(b)} = \sum_{h=1}^{H} A_h \bar{y}_h^{(b)} \quad (12a)$$

be the $b^{th}$ bootstrap post-stratified estimate of the total (12a), and let $$\hat{t}_{ps,boot} = \frac{1}{B}\sum_{b=1}^{B} \hat{t}_{ps}^{(b)} \quad (13a)$$

be the bootstrap estimate of the total (13a). The bootstrap estimator of the variance (14a) is $$\mathcal{V}_{boot} = \frac{1}{1-B}\sum_{b=1}^{B}(\hat{t}_{ps}^{(b)} - \hat{t}_{ps,boot})^2 \quad (14a)$$

To estimate the variance of the areal mean $\hat{\mu}_{ps,boot}=\hat{t}_{ps,boot}/A$ where $\Sigma_{h=1}^{H}H_h$, all terms are divided by $A^2$.

The number of bootstrap resamples should be set at B≥1,000. Larger B can improve the estimates, particularly for bootstrap confidence intervals, though B=1,000 is typically sufficient for estimating bootstrap standard errors.

As a consequence of bootstrap resampling at the field level, it is possible that in any given bootstrap resample there will be no observed soil samples in a given post-stratum, making it impossible to compute $\bar{y}_h^{(b)}$. If this occurs in a few samples it may not be a concern, and the problematic bootstrap resample can be removed from the calculation of the standard deviation (13) or variance 14a. The number of resamples thrown out due to this problem should be reported for transparency, and it cannot exceed 30%×B per requirements, as described in various embodiments herein.

Example 5: Post-Stratification of Single-Stage SRSWR

For single-stage SRSWR designs, post-stratification is straightforward at both the field and sub-field level because the points are the primary sampling units. An SRSWR can be drawn, for example, by sampling points at a constant density across the entire project area. Under this design, the number of points in a given field is a Poisson random variable for sufficiently large sample sizes. Consequently, this design is also referred to as a Poisson sampling design with replacement.

Let $y_{hj}$ be the GHG emission reduction/removal at point j in post-stratum h; let $n_h$ be the observed number of sampling points in post-stratum h; and let $\bar{y}_h=n_h^{-1}\Sigma_{j=1}^{n_h}y_{hj}$ be the mean in post-stratum h. Let $A_h$ be the area of post-stratum h=1, . . . , H, and let $A=\Sigma_{h=1}^{H}A_h$ be the total area. The post-stratified estimator of the total is $$\hat{T}_{ps} = \sum_{h=1}^{H} A_h \bar{y}_h = \sum_{h=1}^{H}\left(\frac{A_h}{n_h}\sum_{j=1}^{n_h} y_{hj}\right) = \sum_{h=1}^{H}\sum_{j=1}^{n_h} w_h h_{hj} \quad (15)$$

where the weights are $w_h=A_h/n_h$. The post-stratified estimator of the variance is $$\widehat{\text{Var}}(\hat{T}_{ps}) = \sum_{h=1}^{H} \frac{A_h^2}{n_h} s_h^2 \quad (16)$$

where $$s_h^2 = \frac{1}{n_h - 1}\sum_{j=1}^{n_h}(y_{hj} - \bar{y}_h)^2. \quad (17)$$

Imputation

For the purposes of modeling % SOC, biogeochemical model inputs may be imputed in the following scenarios:

% SOC: If based on the guidance, as described in various embodiments herein, post-stratifying at the sub-field level is infeasible and post-stratifying at the field level is concerning because missingingess within fields may be related to emission reductions/removals, one may impute % SOC measurements in partially-sampled fields.

Bulk density, soil texture, and soil pH: One may impute these soil attributes wherever they are missing. If % SOC is a strong predictor for the attribute but % SOC is not sampled at the given point, then imputed % SOC may be used as input to the imputation model so long as all imputations follow the guidance, as described in various embodiments herein.

Guidelines for when % SOC can be imputed are stricter than when bulk density, soil texture, and soil pH can be imputed for two reasons. First, % SOC tends to have more spatial variability. Second, growers are rewarded for increasing % SOC. (Although bulk density is important for calculating SOC stocks, an increase in bulk density does not mean carbon was sequestered.)

The remainder of this section provides guidance on how to impute soil measurements, and how to report performance metrics to provide transparency into the imputation results.

Imputation Approach and Model Selection

Imputation at a point may be done with a single draw from a predictive distribution. Compared to conditional mean imputation, taking draws from the predictive distribution maintains similar within-field variability as would have been observed had there been no missing data (described below).

Any model type with a theoretical basis for taking draws from a predictive distribution can be used, including kriging, linear models, or generalized linear models, though other models may also be used. The predictive distribution can be based on a closed-form result, or it can use a resampling or simulation procedure. If imputing multiple soil attributes at the same point (e.g., % SOC and bulk density), one could consider using copulas to capture their correlation.

Project developers may use external datasets to train soil imputation models, including national soil surveys (e.g., SSURGO), remote sensing data (e.g., LiDAR for elevation), and soil samples collected outside of the project.

Reporting Imputation Results and Diagnostics

One may report summaries of 1) missing soil attributes, 2) variability of imputed values, 3) associations between soil attributes, and 4) performance of imputation models. The relevant summaries will depend on the sampling design.

The following summaries should be reported for a sampling design in which the plan is to measure % SOC at all randomly selected points, and to measure bulk density, soil texture, and soil pH at a random subset of selected points. The relevant summaries may be different for other sampling designs.

1. Summaries of the number of missing measurements: for each soil attribute that was imputed, report:
   (a) The number of partially sampled fields (i.e., fields with at least one point at which that attribute was imputed)
   (b) Histogram and summary statistics (including mean, median, min, max, and 10th, 25th, 75th, and 90th percentiles) of the distribution (across fields) of the proportion of points within the field at which the attribute is imputed
2. Variability of imputed values:
   (a) For % SOC: within-field variability of % SOC (i.e., within-field sample variance, averaged across fields) (i) fields with at least 1 imputed % SOC value, and (ii) in fully-sampled fields. The variability of (i) should be at least as large as the variability of (ii).
   (b) For bulk density, soil texture, and soil pH: Global variability of (i) imputed values and (ii) measured values. The variability of (i) should be at least as large as the variability of (ii).
3. Associations between soil attributes:
   (a) Spearman's correlation of % SOC and bulk density for (i) points where both are measured, (ii) points where either or both of % SOC and bulk density are imputed. The two correlations should be similar.
4. Performance of imputation model:
   (a) For all soil attributes: Performance of the imputation model's predictive draws on held-out data (bias, root mean squared error) in cross validation experiments, so that verifiers can see how close absolute bias is to zero and how large RMSE is.

Statistical Adjustment Methods Using Predictions from Bayesian Calibrated Models (160)

This section builds on the above by providing details on how to conduct statistical adjustments when using predictions from Bayesian-calibrated models. As noted above, the estimators in Examples 1 through 5 are applicable when GHG emission reductions/removals are predicted with biogeochemical models for which calibration is not necessary, but in practice biogeochemical models typically need to go through a calibration process before being used in a project. While necessary for minimizing bias, the calibration process can introduce additional uncertainty that may be accounted for.

The below discussion gives a brief overview of Bayesian calibration, and provides details on how to extend the above examples to projects using Bayesian-calibrated biogeochemical models. The statistical aspects of using Bayesian-calibrated models to estimate GHG emission reductions/removals are discussed. The guidance and requirements in the prior discussion (other than the example calculations) are followed when using the methods described below.

Overview of Bayesian Calibration of Biogeochemical Models

Biogeochemical models such as DayCent are typically deterministic functions of covariates (e.g., initial soil organic carbon concentration (% SOC), soil texture, pH, and bulk density) and parameters (e.g., maximum decomposition rates for carbon pools, and the effect of moisture and tillage on decomposition rates). There are typically many parameters that are theoretically constant, though their values are unknown.

In general, model calibration (distinct from covariate calibration) is the process of using calibration data (e.g., % SOC as measured in an experimental study, denoted as z to select parameter values that result in accurate biogeochemical model predictions. However, model calibration is an estimation process, so there is inherently uncertainty in whether the correct parameter values have been selected. Bayesian model calibration quantifies this uncertainty by selecting a distribution of parameter values (the posterior distribution from a Bayesian analysis) instead of a single value. Instead of a single prediction of GHG emission reductions/removals, Bayesian-calibrated models generate L Monte Carlo (MC) draws from a posterior predictive distribution of GHG emission reductions/removals. For one-stage sampling designs these MC draws are denoted as $\tilde{y}_{jl}$ for point j and MC draw l, which are which are realizations of the predictive random variable $\tilde{Y}_j$.

Let $\tau$ be the true population total GHG emission reductions/removals in the form of $tCO_2e$ of $CO_2$, $N_2O$, and $C_H4$ molecules that are not in the atmosphere due to the land management practice changes of growers participating in the project. The sources of uncertainty in estimating $\tau$ with Bayesian-calibrated models include:

1. Potential biogeochemical model prediction errors:
   Potential calibration errors, i.e., the posterior distribution is not concentrated on the truth
   Potential model inadequacy (see Kennedy and O'Hagan)
2. Potential measurement error in calibration data (both model inputs and measured outcomes)
3. Potential measurement error in model inputs used to make predictions outside of the calibration data
4. Sampling variability due to making model predictions at a random selection of fields/points in the project The examples in the remainder of this section describe how to estimate the variance in a way that accounts for all the sources of uncertainty noted above for a few common sampling designs. The first two sources of uncertainty (biogeochemical model prediction errors and calibration data measurement error) are accounted for by taking draws from a posterior predictive distribution that incorporates both sources of variability, and are captured by the $s_{model}^2$ term in the examples below. The third and fourth source of uncertainty (model input measurement errors and sampling variability) are accounted for through the sample variance and is captured by the $s_{sample}^2$ term in the examples below.

Estimation of Total and Variance Using Bayesian-Calibrated Model Predictions (162)

Unadjusted Analyses

As described above, an unadjusted analysis may always be required for comparison to adjusted analyses. An unadjusted analysis may also be provided as the sole analysis if there is no concern over potential nonresponse bias as discussed above.

In an unadjusted analysis, the observed data are analyzed as though there were no missing data.

The exact calculations will depend on the sampling design, though examples are provided below.

Example 6: Unadjusted Analysis of a One-Stage Sampling Design with Bayesian-Calibrated Model Predictions where Points are Selected with a Simple Random Sample with Replacement (SRSWR)

Let $\tilde{Y}_j$ be the predictive random variable for the GHG emission reductions/removals for observed points $j=1, \ldots, n$. Also, let $\tilde{y}_{jl}$, $l=1, \ldots, L$ be MC draws from the posterior predictive distribution of $\tilde{Y}_j$ conditional on the calibration data $z=(z_1, \ldots, z_{n_{cal}})$, and let A be the total area of the project. All $j=1, \ldots, n$ sampled points are outside of the calibration data set.

One can construct a posterior predictive random variable of the population total as $$\tilde{T} = \frac{A}{n}\sum_{j=1}^{n} \tilde{Y}_j. \quad (18)$$

One can estimate the total conditional on the calibration data as $$\hat{T} = \hat{E}[\tilde{T}|z] = \frac{A}{n}\sum_{j=1}^{n} \bar{y}_j \quad (19)$$

where $\bar{y}_j = L^{-1}\sum_{\ell=1}^{L} \tilde{y}_{j\ell}$. Let $$\hat{T}_\ell = \frac{A}{n}\sum_{j=1}^{n} y_{j\ell} \quad (20)$$

be the $l^{th}$ draw from the posterior predictive distribution of the population total. The estimator variance is $$\widehat{Var}(\tilde{T}|z) = \frac{A^2}{n}s_{sample}^2 + s_{model}^2 \quad (21)$$

where $$s_{sample}^2 = \frac{1}{n-1}\sum_{j=1}^{n}(\bar{y}_j - \hat{\mu})^2 \quad (22)$$

$$s_{model}^2 = \frac{1}{L-1}\sum_{\ell=1}^{L}(\hat{T}_\ell - \hat{T})^2 \quad (23)$$

and $\hat{\mu}=\hat{T}/A$ and $\hat{T}=L^{-1}\sum_{l=1}^{L}\hat{T}_l=(A/n)\sum_{j=1}^{n}\bar{y}_j$. To obtain the variance for the areal mean $\mu$, both terms in (21) are divided by $A^2$.

Example 7: Unadjusted Analysis of a Two-Stage Sampling Design with Bayesian-Calibrated Model Predictions where Fields are Selected with Probability Proportional to Size (PPSWR) and Points are Selected with a Simple Random Sample with Replacement (SRSWR)

This is the same as Example 1 but where outcomes are predicted with a Bayesian calibrated model. Let $\tilde{Y}_{ij}$ be the predictive random variable for the GHG emission reductions/removals for field selection $i=1, \ldots, n$ and observed point $j=1, \ldots, m_i$, and let $\tilde{y}_{ijl}$, $l=1, \ldots, L$ be MC draws from the posterior predictive distribution of $\tilde{Y}_{ij}$ conditional of the calibration data $z=(z_1, \ldots, z_{n_{cal}})$. All $i=1, \ldots, n$ sampled fields are outside of the calibration data set. The probability of selecting field i in each draw is $p_i=A_i/A$ where $A=\Sigma_{i=1}^{N}A_i$. One can construct a Hansen-Hurwitz type posterior predictive random variable of the population total as $$\tilde{T} = \frac{1}{n}\sum_{i=1}^{n}\frac{A_i}{p_i}\bar{\tilde{Y}}_i = \frac{A}{n}\sum_{i=1}^{n}\bar{\tilde{Y}}_i \quad (24)$$

where $\bar{\tilde{Y}}_i = m_i^{-1}\Sigma_{j=1}^{m_i}\tilde{Y}_{ij}$.

As described in Appendix D, we can estimate the total conditional on the calibration date as $$\hat{T} = \frac{1}{n}\sum_{i=1}^{n}\frac{A_i}{p_i}\bar{y}_i = \frac{A}{n}\sum_{i=1}^{n}\bar{y}_i \quad (25)$$

where $\bar{y}_i = m_i^{-1}\sum_{j=1}^{m_i} \bar{y}_{ij}$, and $\bar{y}_{ij} = L^{-1}\sum_{\ell=1}^{L} \tilde{y}_{ij\ell}$. Let $$\hat{T}_\ell = \frac{A}{n}\sum_{i=1}^{n}\left(\frac{1}{m_i}\sum_{j=1}^{m_i} y_{ij\ell}\right) \quad (26)$$

be the $l^{th}$ draw from the posterior predictive distribution of the population total. The estimator variance is $$\widehat{Var}(\tilde{T}|z) = \frac{A^2}{n}s_{sample}^2 + s_{model}^2 \quad (27)$$

where $$s_{sample}^2 = \frac{1}{n-1}\sum_{i=1}^{n}(\bar{y}_i - \hat{\mu})^2 \quad (28)$$

$$s_{model}^2 = \frac{1}{L-1}\sum_{\ell=1}^{L}(\hat{T}_\ell - \hat{T})^2 \quad (29)$$

and $\hat{\mu}=\hat{T}/A$ and $\hat{T}=L^{-1}\Sigma_{l=1}^{L}\hat{T}_l=(A/n)\Sigma_{i=1}^{n}\bar{y}$. To obtain the variance for the areal mean $\hat{\mu}$, both terms in (27) are divided by $A^2$.

Example 8: Continuation of Example 7 but where Fields are Selected with Probability Proportional to Estimated Size This is the same as Example 7 but where fields in the first stage are selected with probability proportional to estimated size $\hat{A}_i$, $i=1, \ldots, N$. The probability of selecting field i in each draw is $p_i=\hat{A}_i/\hat{A}$ where $\hat{A}=\Sigma_{i=1}^{N}\hat{A}_i$. Similar to Example 2, one can construct a Hansen-Hurwitz type posterior predictive random variable of the population total as $$\tilde{T} = \frac{1}{n}\sum_{i=1}^{n}\frac{A_i}{p_i}\bar{\tilde{Y}}_i = \frac{\hat{A}}{n}\sum_{i=1}^{n}\frac{A_i}{\hat{A}_i}\bar{\tilde{Y}}_i \quad (30)$$

where $\bar{\tilde{Y}}_i = m_i^{-1}\sum_{j=1}^{m_i} \tilde{Y}_{ij}$.

One can estimate the total conditional on the calibration data as z as $$\hat{T} = \hat{\mathbb{E}}[\tilde{T}|z] = \frac{\hat{A}}{n}\sum_{i=1}^{n}\frac{A_i}{\hat{A}_i}\bar{\tilde{y}}_i \quad (31)$$

where $\bar{\tilde{y}}_i = m_i^{-1}\sum_{j=1}^{m_i}\bar{\tilde{y}}_{ij}$, and $\bar{\tilde{y}}_{ij} = L^{-1}\sum_{\ell=1}^{L}\tilde{y}_{ij\ell}$. Let $$\tilde{T}_\ell = \frac{\hat{A}}{n}\sum_{i=1}^{n}\left(\frac{A_i}{\hat{A}_i m_i}\sum_{j=1}^{m_i} y_{ij\ell}\right) \quad (32)$$

be the $l^{th}$ draw from the posterior predictive distribution of the population total. The estimator variance is $$\widehat{\text{Var}}(\hat{T}|z) = \frac{\hat{A}^2}{n}s^2_{sample} + s^2_{model} \quad (33)$$

where $$s^2_{sample} = \frac{1}{n-1}\sum_{i=1}^{n}\left(\frac{A_i}{\hat{A}_i}\bar{\tilde{y}}_i - \hat{\mu}\right)^2 \quad (34)$$

$$s^2_{model} = \frac{1}{L-1}\sum_{\ell=1}^{L}(\tilde{T}_\ell - \hat{T})^2 \quad (35)$$

and $\hat{\mu} = \hat{T}/A$ and $\hat{T} = L^{-1}\Sigma_{\ell=1}^{L}\tilde{T}_\ell = (\hat{A}/n)\Sigma_{i=1}^{n}(A_i/\hat{A}_i)\bar{\tilde{y}}_i$. To obtain the variance for the areal mean $\hat{\mu}$, both terms in (33) are divided by $A^2$.

Adjusted Analyses

This section covers the statistical estimators of the total GHG emission reduction and removal, as well as the variance, conditional on a selected post-stratification. The specific approach will depend on the project's sampling design and the level at which units are post-stratified. In this section, few examples are provided for common sampling schemes, though others are possible.

Example 9: Post-Stratification at the Field Level with Bayesian-Calibrated Predictions in a Two-Stage Sampling Design where Primary Units (Fields) are Selected with PPSWR and Secondary Units (Points) are Selected by a SRSWR This is the same as Example 3 but where outcomes are predicted with a Bayesian-calibrated model. Let $\tilde{Y}_{ij}$ be the predictive random variable for the GHG emission reductions/removals at observed point $j=1, \ldots, m_i$ in field selection $i=1, \ldots, n_h$ of post-stratum $h=1, \ldots, H$ and let $\tilde{y}_{ij\ell}$, $l=1, \ldots, L$, be an MC draw from posterior predictive distribution of $\tilde{Y}_{ij}$.

Applying the results of Example 6 within each stratum, where fields are the primary sampling units instead of points, one can construct a posterior predictive random variable for the population total in post-stratum h as $$\tilde{T}_h = \frac{A_h}{n_h}\sum_{i=1}^{n_h}\bar{\tilde{y}}_{hi} \quad (36)$$

Where $\bar{\tilde{Y}}_{hi} = m_i^{-1}\Sigma_{i=1}^{m_i}\tilde{Y}_{hij}$. Also, let $\tilde{T}_{ps} = \Sigma_{h=1}^{H}\tilde{T}_h$ be the predictive random variable of the post-stratified population total.

One can estimate the population total in stratum h conditional on the calibration data as $$\hat{T}_h = \hat{\mathbb{E}}[\tilde{T}_h|z] = \frac{A_h}{n_h}\sum_{i=1}^{n_h}\bar{\tilde{y}}_{hi} \quad (37)$$

where $\bar{\tilde{y}}_{hi} = m_i^{-1}\sum_{j=1}^{m_i}\bar{\tilde{y}}_{hij}$ and $\bar{\tilde{y}}_{hij} = L^{-1}\sum_{\ell=1}^{L}\tilde{y}_{hij\ell}$. Let $$\tilde{T}_{h\ell} = \frac{A_h}{n_h m_i}\sum_{i=1}^{n_h}\sum_{j=1}^{m_i}\tilde{y}_{hij\ell} \quad (38)$$

be the $l^{th}$ MC draw of the population total in post-straum h. To estimate the variance, it is typically recommended to condition on the size of the post-strata, which gives $$\widehat{\text{Var}}(\tilde{T}_h|z) = \frac{A_h^2}{n_h}s^2_{sample,h} + s^2_{model,h} \quad (39)$$

where $$s^2_{sample,h} = \frac{1}{n_h-1}\sum_{i=1}^{n_h}(\bar{\tilde{y}}_{hi} - \hat{\mu}_h)^2 \quad (40)$$

$$s^2_{model,h} = \frac{1}{L-1}\sum_{\ell=1}^{L}(\tilde{T}_{h\ell} - \hat{T}_h)^2 \quad (41)$$

and $\hat{\mu}_h = \hat{T}_h/A_h$ and $\hat{T}_h = L^{-1}\Sigma_{\ell=1}^{L}\tilde{T}_{h\ell} = (A_h/n_h)\Sigma_{i=1}^{n_h}\bar{\tilde{y}}_{hi}$. The post-stratified estimator of the total is $$\hat{T}_{ps} = \sum_{h=1}^{H}\hat{T}_h = \sum_{h=1}^{H}\left(\frac{A_h}{n_h}\sum_{i=1}^{n_h}\bar{\tilde{y}}_{hi}\right) \quad (42)$$

and the post-stratified estimator of the variance is $$\widehat{\text{Var}}(\hat{T}_{ps}|z) = \sum_{h=1}^{H}\widehat{\text{Var}}(\tilde{T}_h|z) = \sum_{h=1}^{H}\left\{\frac{A_h^2}{n_h}s^2_{sample,h} + s^2_{model,h}\right\}. \quad (43)$$

To obtain the variance for the areal mean $\hat{\mu}_{ps} = \hat{T}_{ps}/A$, for each post-stratum $h=1, \ldots, H$ the corresponding terms in (43) are divided by $A_h^2$.

Example 10: Continuation of Example 9 when Post-Stratifying at the Subfield Level This is a continuation of Example 9, though now suppose that post-strata are formed at the sub-field level. Because primary sampling units (fields) can be split across multiple post-strata, the subscript i is dropped for fields and re-index observed points in stratum h as $j=1, \ldots, n_h$.

As in Example 4, the estimate of variance is not straightforward because the primary sampling units can be split across different post-strata. In particular, one can no longer estimate $s_{sample}^2$ within the post-strata. However, on can still estimate $s_{model}^2$ and then obtain sampling variability through a bootstrap or jackknife procedure. When conducting bootstrap or jackknife resampling, the units for resampling should be the primary units (fields) to mimic the original sample design, as these are the largest independent units (ultimate clusters).

For example, with bootstrap resampling, for each of b=1, ..., B resamples, a sample of n of the observed field selections would be resampled with replacement to form the $b^{th}$ bootstrap resample.

With regard to the first bootstrap estimator of Example 4, the population total can be estimated as $$\hat{T}_{ps} = \sum_{h=1}^{H} A_h \bar{\bar{y}}_h \quad (44)$$

where $\bar{\bar{y}}_h = n_h^{-1} \sum_{j=1}^{n_h} \bar{y}_{hj}$ and $\bar{y}_{hj} = L^{-1} \sum_{\ell=1}^{L} y_{hj\ell}$.

For each bootstrap resample, the within-strata totals would be calculated as $$\hat{T}_h^{(b)} = \frac{A_h}{n_h^{(b)}} \sum_{j=1}^{n_h^{(b)}} \bar{y}_{hj}^{(b)} \quad (45)$$

where $\bar{y}_{hj}^{(b)} = L^{-1} \sum_{\ell=1}^{L} \tilde{y}_{hj\ell}^{(b)}$. Also, let $$\tilde{T}_{h\ell}^{(b)} = \frac{A_h}{n_h^{(b)}} \sum_{j=1}^{n_h^{(b)}} y_{hj\ell}^{(b)} \quad (46)$$

be the $l^{th}$ draw from the posterior predictive distribution of the population total in post-stratum h. The estimator of model variance for the bill bootstrap resample is $$v_{model,h}^{(b)} = \frac{1}{L-1} \sum_{\ell=1}^{L} \left( \tilde{T}_{h\ell}^{(b)} - \hat{T}_h^{(b)} \right)^2 \quad (47)$$

where $\hat{T}_h^{(b)} = L^{-1} \sum_{\ell=1}^{L} \tilde{T}_{h\ell}^{(b)} = (A_h/n_h^{(b)}) \sum_{j=1}^{n_h^{(b)}} \bar{y}_{hj}^{(b)}$.

Let $\hat{T}_{boot,h} = B^{-1} \sum_{b=1}^{B} \tilde{T}_h^{(b)}$ be the mean of the bootstrap totals. The variance of $\hat{T}_{boot,h}$ can be decomposed into between- and within-bootstrap variance components (i.e., sampling and model variance, respectively) as $$\text{Var}(\hat{T}_{boot,h} | z) = \text{Var}(\mathbb{E}[\hat{T}_{boot,h} | b, z] | z) + \mathbb{E}[\text{Var}(\hat{T}_{boot,h} | b, z) z] \quad (48)$$

which can be estimated as $$\sum_{\ell=1}^{L} (\hat{T}_{boot,h} | z) = v_{sample,h} + v_{model,h} \quad (49)$$

where $$v_{sample,h} = \frac{1}{B-1} \sum_{b=1}^{B} \left( \hat{T}_h^{(b)} - \hat{T}_{boot,h} \right)^2 \quad (50)$$

$$v_{model,h} = \frac{1}{B} \sum_{b=1}^{B} v_{model,h}^{(b)} \quad (51)$$

The bootstrap estimator of the population total is $$\hat{T}_{boot} = \sum_{h=1}^{H} \hat{T}_{boot,h} = \frac{1}{B} \sum_{h=1}^{H} \sum_{b=1}^{B} \hat{T}_h^{(b)} \quad (52)$$

and the bootstrap estimator of variance of the population total is $$\widehat{\text{Var}}(\hat{T}_{boot} | z) = \sum_{h=1}^{H} \widehat{\text{Var}}(\hat{T}_{boot,h} | z) \quad (53)$$

$$= \sum_{h=1}^{H} \{v_{sample,h} + v_{model,h}\}$$

Note that in (53) the sampling variance $v_{sample,h}$ is not multiplied by $A_h^2/n_h$ as in other examples. Similar to Example 4, one does not divide by $n_h$ because (53) is the variance for the total, not the points (standard error versus standard deviation). Unlike Example 4, one does not multiply by $A_h^2$ because $A_h$ is already included in the calculation of $\hat{T}_h^{(b)}$.

To obtain the variance for the areal mean $\hat{u}_{boot} = \hat{T}_{boot}/A$, for each post-stratum h=1, ..., H the corresponding terms in (53) are divided by $A_h^2$.

With regard to the second bootstrap estimator of Example 4, for each bootstrap resample, let $$\tilde{T}_{ps,\ell}^{(b)} = \sum_{h=1}^{H} \frac{A_h}{n_h^{(b)}} \sum_{j=1}^{n_h^{(b)}} \tilde{y}_{hj\ell}^{(b)}$$

be the $l^{th}$ draw from the posterior predictive distribution of the population total. The $b^{th}$ bootstrap post-stratified estimate of the total is $$\hat{T}_{ps}^{(b)} = \frac{1}{L} \sum_{\ell=1}^{L} \tilde{T}_{ps,\ell}^{(b)}$$

$$= \sum_{h=1}^{H} \frac{A_h}{n_h^{(b)}} \sum_{j=1}^{n_h^{(b)}} \tilde{\bar{y}}_{hj}^{(b)}$$

where $\tilde{\bar{y}}_{hj}^{(b)} = L^{-1} \sum_{\ell=1}^{L} \tilde{y}_{hj\ell}^{(b)}$.

The variance estimator for the $b^{th}$ bootstrap resample is $$v^{(b)} = \frac{1}{L-1} \sum_{\ell=1}^{L} \left( \tilde{T}_{ps,\ell}^{(b)} - \hat{T}_{ps}^{(b)} \right)^2$$

Let $$\hat{T}_{ps,boot} = \frac{1}{B} \sum_{b=1}^{B} \hat{T}_{ps}^{(b)}$$

be the mean of the bootstrap totals.

The variance of $\hat{\tau}_{ps,boot}$ can be estimated as $$\widehat{\text{Var}}(\hat{T}_{ps,boot} | z) = v_{sample} + v_{model}$$

Where $$v_{sample} = \frac{1}{B-1} \sum_{b=1}^{B} \left( \hat{T}_{ps}^{(b)} - \hat{T}_{ps,boot} \right)^2$$

-continued $$v_{model} = \frac{1}{B}\sum_{b=1}^{B} v^{(b)}.$$

To estimate the variance of the areal mean $\hat{\mu}_{ps,boot} = \hat{\tau}_{ps,boot}/A$, all terms in the expression for $\widehat{Var}(\hat{\tau}_{ps}|z)$ are divided by $A^2$.

The number of bootstrap resamples should be set at $B \geq 1,000$. Larger B can improve the estimates, particularly for bootstrap confidence intervals, though B=1,000 is typically sufficient for estimating bootstrap standard errors.

As a consequence of resampling at the field level, it is possible that in any given bootstrap resample there will be no observed soil samples in a given post-stratum, making it impossible to compute the total and variance for that stratum. If this occurs in a few bootstrap samples it may not be a concern, and the problematic bootstrap resample can be removed from the calculation of the variance (49) or $\widehat{Var}(\hat{\tau}_{ps}|z)$ (the number B in the denominator should be equal to the number of bootstrap samples that were not thrown out, and $\hat{T}_{boot,h}$ should be taken as the mean over the bootstrap samples that were not thrown out). The number of resamples thrown out due to this problem should be reported for transparency, and it cannot exceed 30%×B per requirements discussed above.

Example 11: Post-Stratification of Single-Stage SRSWR with Bayesian-Calibrated Model Predictions This example is the same as Example 5 but with Bayesian-calibrated model predictions. Let $\tilde{Y}_{hj}$ be the predictive random variable for the GHG emission reductions/removals at observed point $j=1, \ldots, n_h$ in post-stratum $h=1, \ldots, H$. Also, let $\tilde{y}_{hjl}$, $l=1, \ldots, L$ be MC draws from the posterior predictive distribution of $\tilde{Y}_{hj}$ conditional on the calibration data $z=(z_1, \ldots, z_{n_{cal}})$, and let $A_h$ be the total area of post-stratum h. All $j=1, \ldots, n$ sampled points are outside of the calibration data set.

One can construct a posterior predictive random variable of the total in stratum h as $$\tilde{T}_h = \frac{A_h}{n_h}\sum_{j=1}^{n} \tilde{Y}_{hj}. \tag{54}$$

Also, let $\tilde{T}_{ps} = \sum_{h=1}^{H} \tilde{T}_h$ be the post-stratified predictive random variable of the population total. One can estimate the total conditional on the calibration data as $$\hat{T}_h = \hat{\mathbb{E}}[\tilde{T}_h|z] = \frac{A_h}{n_h}\sum_{j=1}^{n_h} \bar{\tilde{y}}_{hj} \tag{55}$$

where $\bar{\tilde{y}}_{hj} = L^{-1}\sum_{\ell=1}^{L} \tilde{y}_{hj\ell}$.

Let $\hat{T}_{h\ell} = \frac{A_h}{n_h}\sum_{j=1}^{n_h} y_{hj\ell}. \tag{56}$ be the $l^{th}$ draw from the posterior predictive distribution of the population total in post-stratum h. The estimator of variance in post-stratum h is $$\widehat{Var}(\tilde{T}_h|z) = \frac{A_h^2}{n_h}s^2_{sample,h} + s^2_{model,h} \tag{57}$$

where $$s^2_{sample,h} = \frac{1}{n_h - 1}\sum_{j=1}^{n_h}(\bar{\tilde{y}}_{hj} - \hat{\mu}_h)^2 \tag{58}$$

$$s^2_{model,h} = \frac{1}{L-1}\sum_{\ell=1}^{L}(\hat{T}_{h\ell} - \hat{T}_h)^2 \tag{59}$$

and $\hat{\mu}_h = \hat{T}_h/A_h$ and $\hat{T}_h = L^{-1}\sum_{\ell=1}^{L}\hat{T}_{h\ell} = (A_h/n_h)\sum_{j=1}^{n_h}\bar{\tilde{y}}_{hj}$. The post-stratified estimator of the population total is $$\hat{T}_{ps} = \sum_{h=1}^{H}\hat{T}_h = \sum_{h=1}^{H}\left(\frac{A_h}{n_h}\sum_{j=1}^{n_h}\bar{\tilde{y}}_{hj}\right) \tag{60}$$

and the post-stratified estimator of variance of the population total is $$\widehat{Var}(\tilde{T}_{ps}|z) = \sum_{h=1}^{H}\widehat{Var}(\tilde{T}_h|z) = \sum_{h=1}^{H}\left\{\frac{A_h^2}{n_h}s^2_{sample,h} + s^2_{model,h}\right\} \tag{61}$$

To obtain the variance for the areal mean $\hat{\mu}_{ps} = \hat{T}_{ps}/A$, for each post-stratum $h=1, \ldots, H$ the corresponding terms in (61) are divided by $A_h^2$.

Combining Estimates Across Pre-Strata

Projects may pre-stratify the population, meaning that they partition the population into non-overlapping subsets and select sample points within each pre-stratum, independently of the other pre-strata. The sample design may vary from one pre-stratum to another, and there may be post-strata within each pre-stratum. Pre-stratification can reduce uncertainty without increasing the sample size by allocating more sampling to more heterogeneous pre-strata. The following example shows how to combine the estimates from the pre-strata.

Example 12: Pre-Stratification

The project's spatial boundary is partitioned into G non-overlapping pre-strata, indexed by $g=1, \ldots, G$. Within each pre-stratum, sample points are selected independently of the other pre-strata. Let $A_g$ be the area of pre-stratum g. (In previous examples, the index g was suppressed for pre-strata because all calculations were specific to a single pre-stratum. If post-stratification is done within pre-stratum g, then the total area in pre-stratum g is equal to the sum of the post-strata areas within pre-stratum g, i.e., $A_g = \sum_h A_{gh}$ where $A_{gh}$ is the area of post-stratum h within pre-stratum g.) Because pre-strata do not spatially overlap, the total area of the project, A, equals the sum $\sum_{g=1}^{G} A_g$.

A posterior predictive random variable of the population total can be constructed as the sum of the total in each pre-stratum:

$$\tilde{T} = \sum_{g=1}^{G}\tilde{T}_g$$

where $\tilde{\tau}_g$ is the posterior predictive random variable of the population total in pre-stratum g, constructed using the example above that is appropriate for the sample design deployed in pre-stratum g. Similar to the area $A_g$, if post-stratification is used within pre-stratum g, then $\tilde{\tau}_g = \Sigma_h \tilde{\tau}_{hg}$ where $\tilde{\tau}_{hg}$ is the total within post-stratum h of pre-stratum g. The total conditional on the calibration data can be estimated as the sum $$\hat{T} = \hat{\mathbb{E}}[\hat{T}|z] = \sum_{g=1}^{G} \hat{\tau}_g$$

where $\hat{\tau}_g$ is the estimate appropriate for the sample design in pre-stratum g (summed over any post-strata within pre-stratum g, if applicable).

Let $\tilde{\tau}_{gl}$ be the $l^{th}$ draw from the posterior predictive distribution of the total in pre-stratum g, and let $\tilde{\tau}_l$ be the $l^{th}$ draw from the posterior predictive distribution of the population total.

Let $v_{sample,g}$ be the estimated sampling variance for stratum g. $v_{sample,g}$ can be retrieved from the example above that was deployed in pre-stratum g; for example, for the unadjusted SRSWR (Example 6), $v_{sample,g}$ is the first term on the right-hand of Eq. (21) with the pre-stratum label g attached to all the variables: $(A_g^2/n_g)s_{sample,g}^2$ The estimator of variance is $$\widetilde{Var}(\hat{T}|z) = v_{sample} + s_{model}^2$$

where $$v_{sample} = \sum_{g=1}^{G} s_{model,g}^2$$

$$v_{model} = \frac{1}{L-1} \sum_{\ell=1}^{L} (\tilde{T}_\ell - \hat{T})^2$$

and the estimated areal mean is $\hat{\mu} = \hat{\tau}/A$. To estimate the variance for the areal mean $\hat{\mu}$, both terms in) $\widetilde{Var}(\tilde{\tau}|z)$ are divided by $A^2$.

In the expression for $v_{sample}$, the sampling variance of the total is the sum of the sampling variances in the individual pre-strata. The reason is that the sample locations are chosen independently across pre-strata.

Figure 3A:
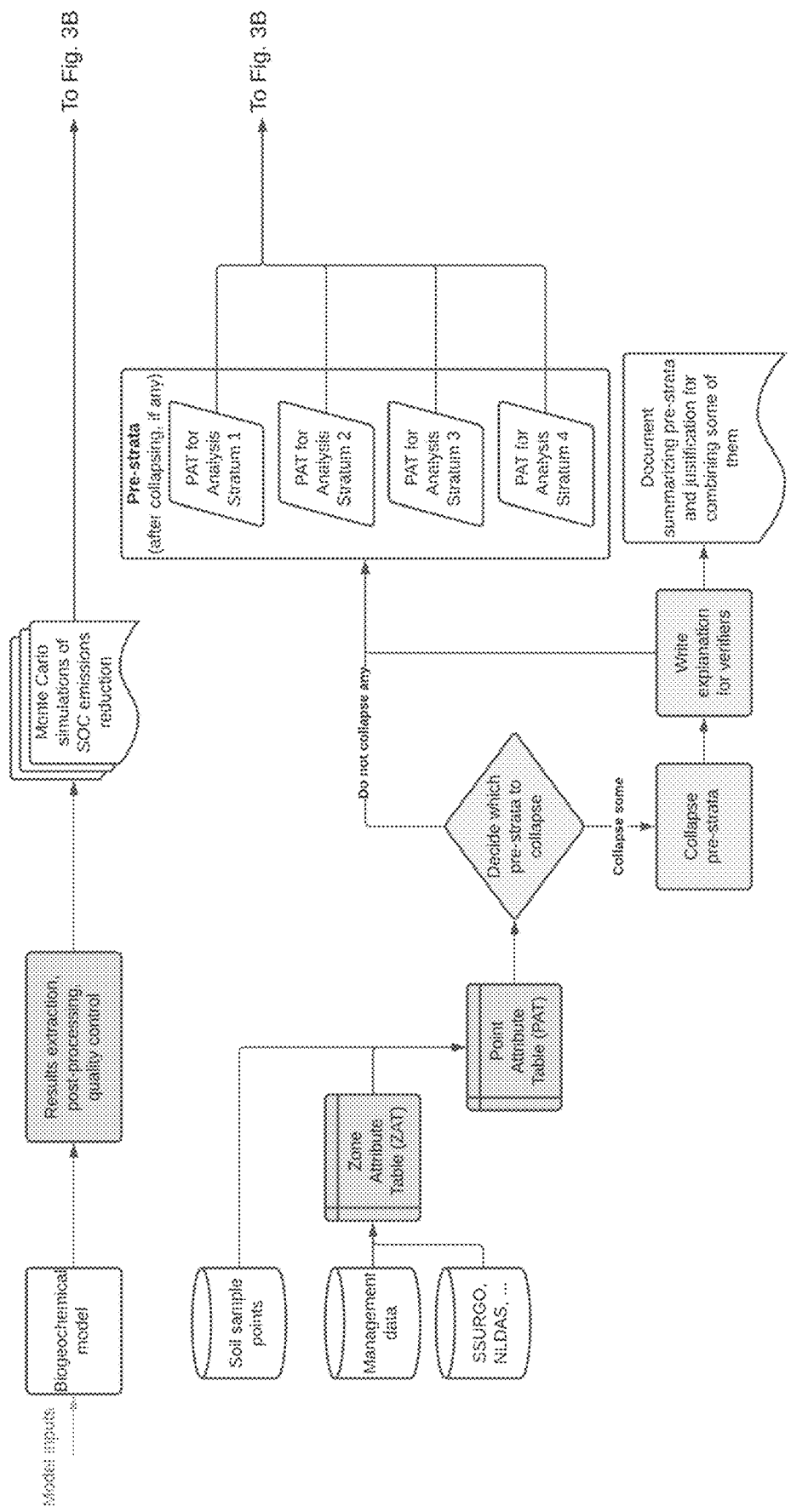
Figure 3B:
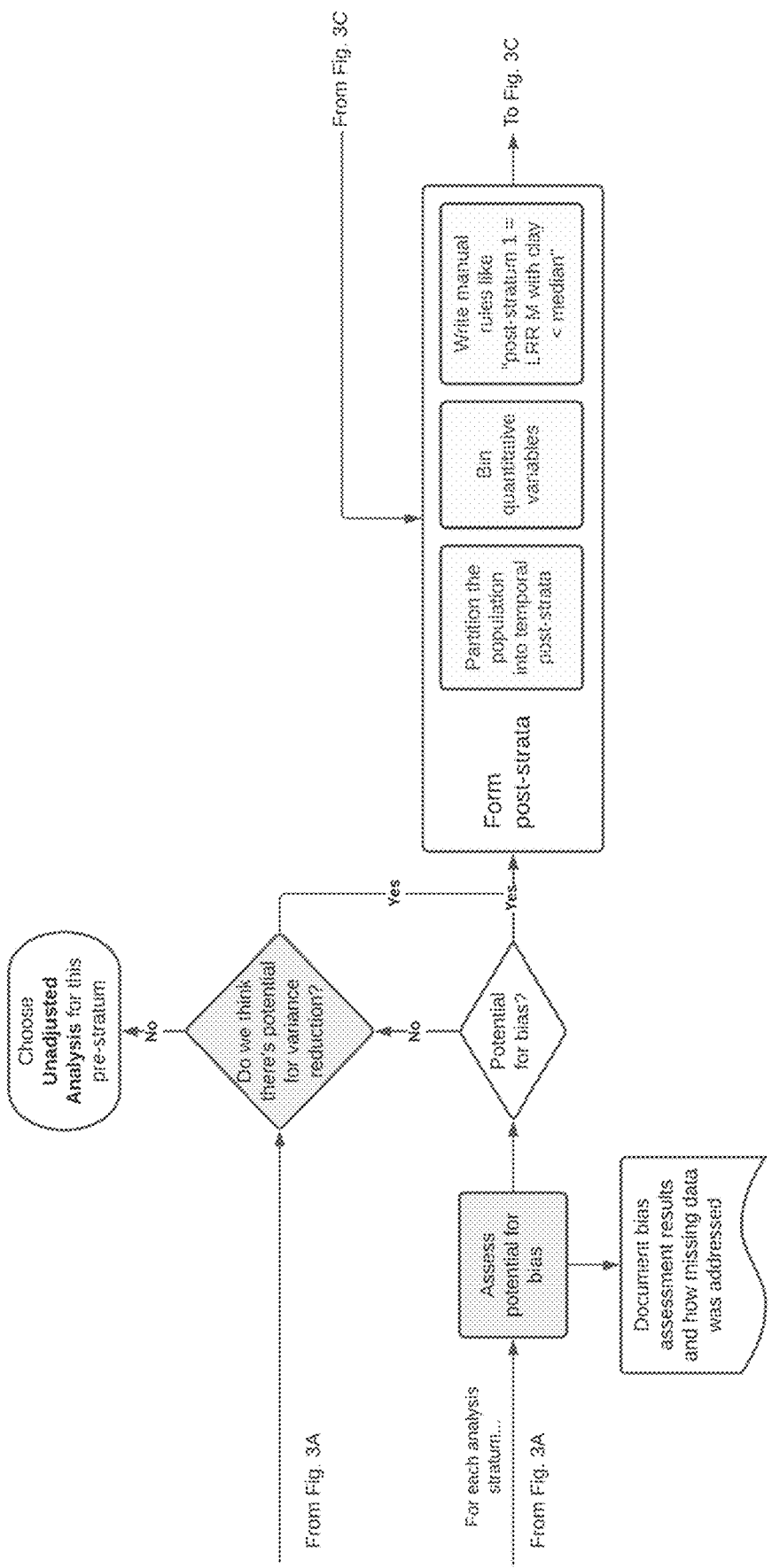
Figure 3C:
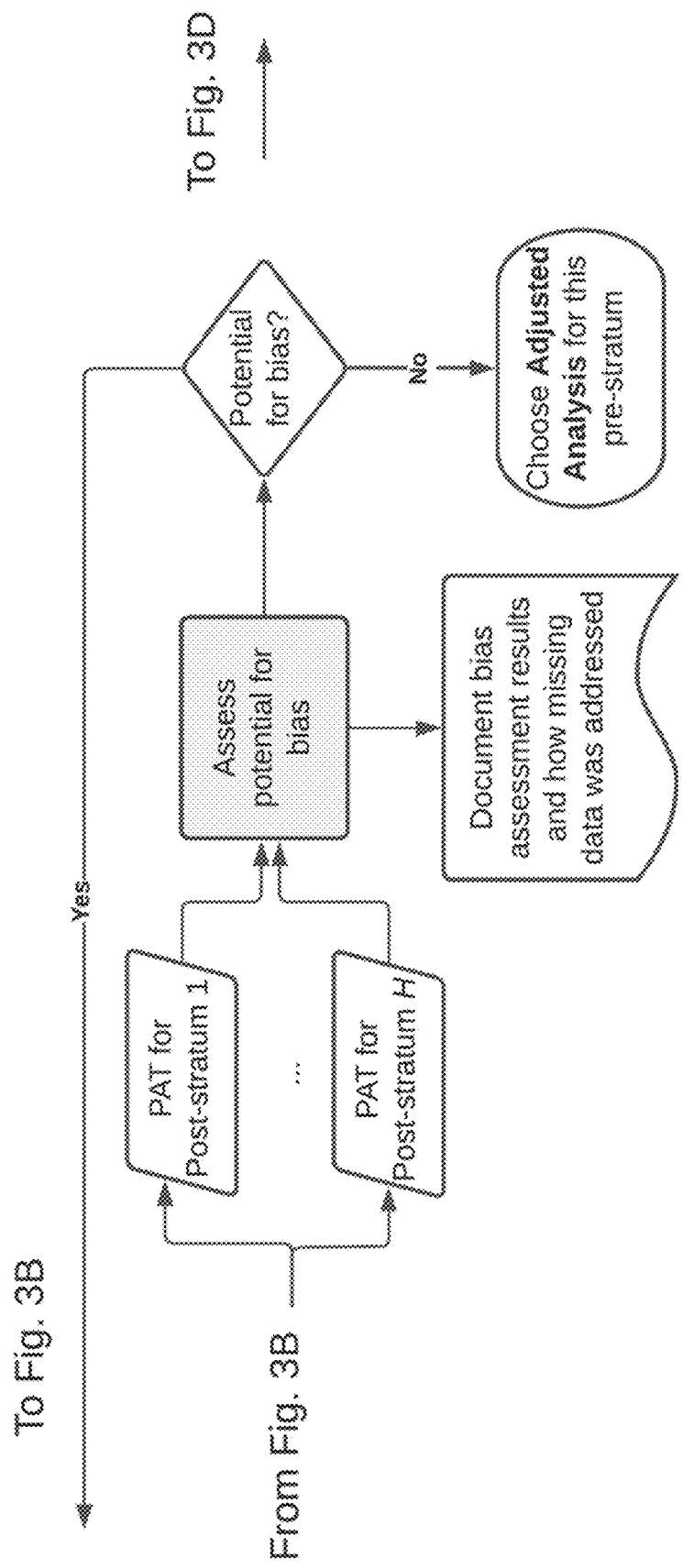
Figure 3E:
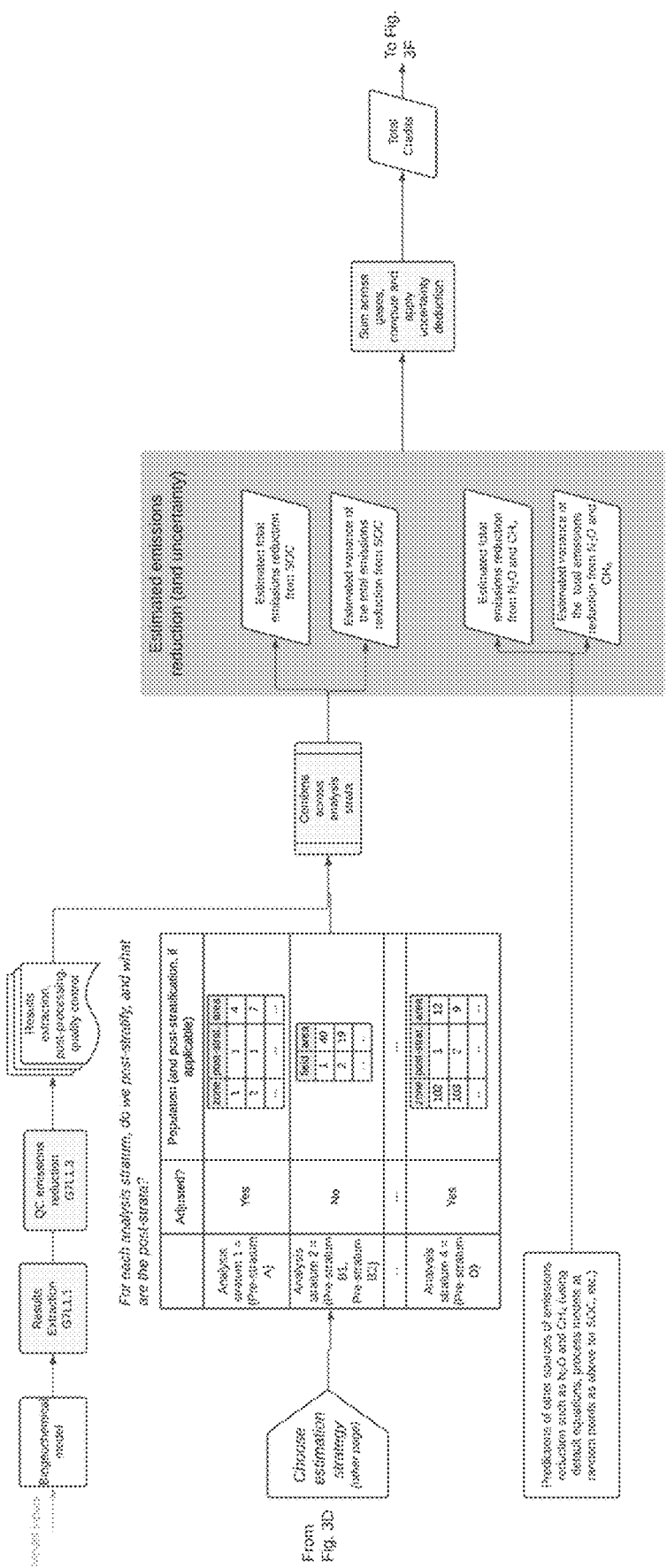
Figure 3F:
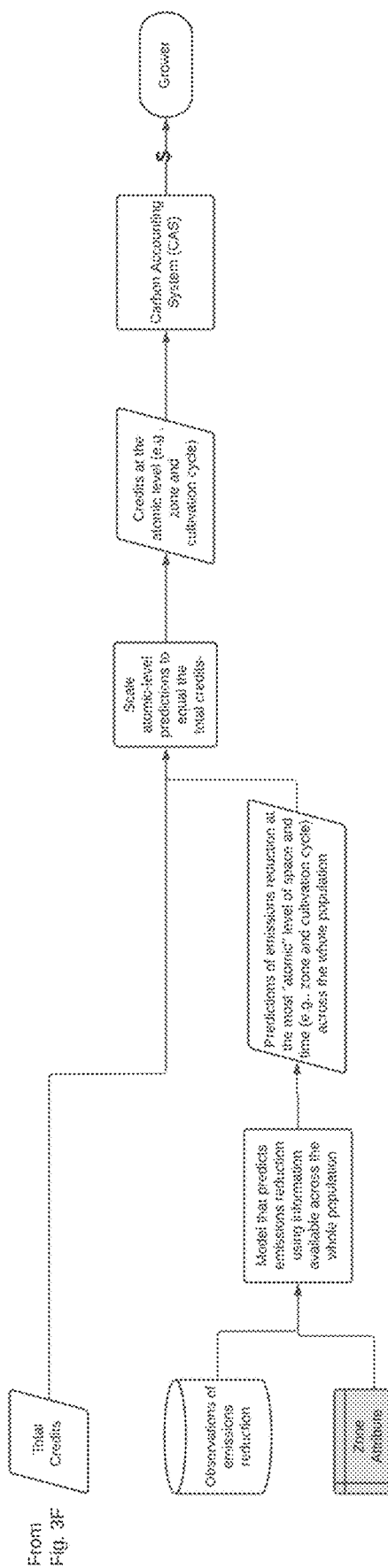

FIGS. 3A-3F illustrate a flow diagram for estimating greenhouse gas emissions reduction. In particular, FIGS. 3A-3D illustrate a flow diagram for determining pre-strata, determining if a potential for bias exists in each pre-strata, and determining post-strata for each pre-stratum when a potential for bias exists. FIGS. 3E-3F illustrate a flow diagram for estimating total greenhouse gas emissions reduction based on the pre-strata or post-strata. Additionally, FIG. 3F illustrates how the greenhouse gas emissions reduction may be estimated at fine spatial and temporal scales by making predictions of emissions reduction using what data may be available at all the small spatiotemporal units. In various embodiments, the small spatio-temporal units may be the pairs of management zone and cultivation cycle. The example technique depicted in FIG. 3F is to scale the small-area estimates so that they sum to the "design-based" estimate of the total that was obtained using the estimates made where soil samples were taken. For example, if the small-area estimates are 10, 30, and 40 tonnes while the design-based estimate of the total is 100 tonnes, the small-area estimates are each scaled by 100/(10+30+40)=1.25, so that the small-area estimates sum to the design-based estimate of the total of 100 tonnes.

In various embodiments, the system may receive as input soil attributes from a soil attribute database. In various embodiments, the soil attributes may include attributes of soil sample locations within a land area. In various embodiments, the soil attributes may include: % SOC, soil pH, soil texture, and/or soil bulk density. Soil attributes may be defined as attributes of the soil, such as SOC concentration, bulk density, pH, and/or soil texture (% clay, % sand, % silt). In various embodiments, the soil attributes may be used to estimate soil organic carbon (SOC) emissions reduction. In various embodiments, estimating the SOC emission reduction may be performed by generating a plurality of simulations. In various embodiments, the simulations may be Monte Carlo simulations using random number sampling of one or more variables.

In various embodiments, the system may receive as input soil data from one or more soil data databases. In various embodiments, the soil data may include soil sample points/locations from a soil sample point database. In various embodiments, the soil sample locations may be specific locations where soil samples are taken or to be taken. In various embodiments, the soil data may include land management data. In various embodiments, land management data may include land management practices over time for regions of land. In various embodiments, the land management data may include an indicator that the land management practice has changed to a different land management practice. For example, a certain land region may have adopted cover crop, changed from conventional tillage to no tillage, and/or changed from conventional tillage to reduced tillage. In various embodiments, the soil data may include soil properties/characteristics from a soil database, such as a national database (e.g., SSURGO, NLDAS, etc.). In various embodiments, the soil data may be received by a table of attributes describing management zones (regions within agricultural that are managed differently), referred to as a zone attribute table (ZAT). In various embodiments, the ZAT is a table in a database (e.g., a cloud data warehouse). In various embodiments, each row corresponds to a unique pair of management zone and period of time (such as a growing season or cultivation cycle). In various embodiments, the columns correspond to different soil attributes, weather history, and land management data. In various embodiments, the soil attributes may be determined from a regional soil database, e.g., gSSURGO. Exemplary attributes may include SOC, bulk density, pH, texture from gSSURGO, weather history from NLDAS (e.g., precipitation, max average daily temperature, etc.), and management data collected from growers (e.g., fertilizer application, practice changes, crops, etc.).

In various embodiments, a point attribute table (PAT) may receive the soil sample locations and the other soil data. In various embodiments, the PAT is a table in a database (e.g., a cloud data warehouse). In various embodiments, the PAT may be determined as a spatial join between 1) the ZAT and 2) a table containing one row per sample point, with laboratory results for SOC, and where applicable, bulk density, pH, and texture. In various embodiments, the PAT may include a unique row for each pair of sample point and time period (such as growing season or cultivation cycle).

In various embodiments, a plurality of pre-strata may be determined based on the data related to emissions reduction (e.g., management data, and/or soil properties). In various embodiments, sample locations are planned a in pre-stratum using a randomization scheme such as simple random sampling, grid sampling, multi-stage sampling, cluster sampling, etc.

In various embodiments, two or more pre-strata may be combined into a single stratum for analysis of the measurements. Such strata, which may be the result of combining one or more strata for the purposes of analysis, may be referred to as "analysis strata," as depicted in FIGS. 3D and 3E. In various embodiments, the decision to combine pre-strata may be based on how similar they are (e.g., if the frequency of practice changes are similar, the soil attributes are similar, other attributes related to emissions reduction are similar; if the measurement methods used in the pre-strata are similar; if the measurement was performed by the same people). In various embodiments, the analysis strata that results from combining multiple pre-strata may then be divided into post-strata. In various embodiments, combining pre-strata into a single analysis stratum can avoid standardized differences that are spuriously high due to small sample sizes. In various embodiments, combining pre-strata can enable formation of more post-strata that better reduce standardized differences and variance. As shown in FIG. 3A, analysis strata 1, 2, 3, and 4 have been generated based on the soil data.

In various embodiments, for each pre-strata, the potential for bias may be determined. In various embodiments, if the potential for bias is above a predetermined threshold for a particular pre-stratum, the system may generate one or more post-strata for that particular pre-stratum. In various embodiments, the predetermined threshold may be expressed as a probability. For example, the predetermined threshold may be 50%, 60%, 70%, 75%, 80%, 85%, 90%, 95%, 98%, 99%, 100%, 125%, 150%, 200%, 300%, 400%, 500%, etc. In various embodiments, potential for bias may be determined using the standardized mean difference (SMD), and the predetermined threshold may be 10% or 25%. In various embodiments, the SMD is not constrained to be <100%. In various embodiments, the potential for bias may be determined based on correlation between the target variable of interest (e.g., emission reduction) and the value of an attribute on (e.g., mean annual precipitation, organic matter content in gSSURGO, etc.) on a piece of land and segment of time (e.g., sub-field zone and cultivation cycle), and the SMD for that attribute. For example, if the SMD is large (e.g., SMD=50%) but the correlation with the target variable is small (e.g., 0.03), then the large SMD for that attribute is unlikely to create bias. In various embodiments, the correlation between target variable and attribute may be a Pearson correlation coefficient, a Spearman correlation coefficient, or a Kendall rank correlation coefficient. In various embodiments, if there is little (e.g., no) potential for bias (for all attributes, SMD is 10% or (SMD is <25% and correlation <10%)), but there is a potential for variance reduction, the system may choose an adjusted analysis, such as using post-stratification as described above, for that particular pre-stratum. In various embodiments, the rule for assessing potential for bias may be based on standardized differences alone (e.g., all SMD values are <10%). In various embodiments, the rule for assessing potential for bias may be based on standardized differences and on correlations with the target variable (e.g., for all strata for all attributes: SMD <10% or (SMD <25% and correlation <10%)).

In various embodiments, if there is a potential for bias in the particular pre-stratum, post-strata may be generated by partitioning the land region represented by the pre-strata into post-strata. In various embodiments, the plurality of post-strata may be disjoint subsets of the particular pre-stratum. As described above, post-stratification uses auxiliary variables to group units (either fields or sub-field areas) into mutually exclusive strata, or cells, after the sample has been designed. In various embodiments, the units may be binned based on one or more of the auxiliary variables. In various embodiments, unsupervised learning may be applied to determine bins. In various embodiments, clustering may be used to determine a plurality of bins (e.g., groups of fields or subfields). In various embodiments, the clustering may include spectral clustering. In various embodiments, the clustering may include density-based spatial clustering of applications with noise (DBSCAN). In various embodiments, k-means clustering may be used to determine the plurality of bins. In various embodiments, one or more rules may be applied to the groups. In various embodiments, for k-means clustering, the number of bins (k) and the variables to use for clustering may be determined manually. In various embodiments, the k-means algorithm may partition the management zones so that each zone is in one and only one cluster. In various embodiments, a rule may employ a partition of space into geographic regions (e.g., states, counties, agricultural regions). In various embodiments, a rule may require a year to be before or after a specific year (e.g., <2020 or >=2020). In various embodiments, a rule may require a soil carbon percent to be above, equal to, or lower than a specific value (e.g., <1.7 or >=1.7). Various embodiments described herein may refer to techniques of determining a post-stratum that includes partitioning one or more lands or fields, and binning the one or more lands or fields. Such techniques, however, may equally or more generally be applicable to partitioning space and time into one or more spacetime units and binning the one or more spacetime units without departing from the scope or spirit of what is described herein. In some examples, spacetime units may include spatial units, which may include, for example, fields, sub-field zones, pixels, and/or the like. These fields, sub-fields, and/or pixels may each contain zero or more soil sample locations of one or more soil sample locations. In some examples, spacetime units may include time units, which may include, for example, growing seasons, cultivation cycles, calendar years, and/or the like. In various embodiments describe herein, a goal of the use of spacetime units may be to quantify emissions reduction on these spatial units and their associated time periods. Binning the one or more spacetime units may include, for example, binning the units into pairs of pixels and years, pairs of sub-field zone and cultivation cycle, a combination of spatial unit and time unit, and/or the like. In various embodiments described herein, a ZAT may include attributes of all spacetime for emissions reduction is sought and a PAT may include all attributes of all planned sample locations.

In various embodiments, the decision to post-stratify may be determined based on variance of emissions reduction. In various embodiments, a variance of emissions reduction using pre-strata may be determined, and a variance of emissions reduction using post-strata may be determined. In various embodiments, the difference between the estimated variance using pre-strata and post-strata may be determined. In various embodiments, when the difference is above a predetermined threshold, the system may choose the post-stratified estimate of emissions reduction.

In various embodiments, a PAT may be generated for each post-stratum. In various embodiments, the PAT generated for each post-stratum may be a subset of rows in the PAT representing the post-stratum. In various embodiments, each post-stratum may be assessed for potential bias. In various embodiments, if one or more post-stratum have a potential for bias above a predetermined threshold, the system may re-generate post-strata. In various embodiments, one or more rules may be applied to form the post-strata. For example, two post-strata may be formed as follows: 1) cultivation cycles that end on or before Dec. 31, 2020 and 2) those ending after Dec. 31, 2020. In this example, new rules may be defined that further split each of the post-strata into fields in land resource region M vs land resource region F. In various embodiments, the rules may be determined and applied manually. In various embodiments, once the one or more rules are set, the rules may be automatically applied to determine post-strata. In various embodiments, if there is low (e.g., no) potential for bias from each post-stratum, the process may terminate and produce a post-stratification that satisfactorily reduces potential for bias (and/or variance).

In various embodiments, multiple candidate post-stratifications may be selected from depending on how much the post-stratification reduces variance. For example, one or more post-stratification that reduces variance the most among multiple candidate post-stratifications may be selected.

In various embodiments, based on the pre-strata and/or post-strata, estimated emissions reduction and uncertainty (e.g., variance) may be determined. In various embodiments, land management data may be used with default equations (e.g., provided by regulatory bodies) to determine an estimated total emissions reduction.

In various embodiments, in determining the estimated deductions, the estimated reduction in emissions may be summed across all relevant greenhouse gases and an uncertainty deduction may be determined. In various embodiments, a leakage deduction may be applied. In various embodiments, a registry buffer pool contribution may be applied based on regulatory standards. In various embodiments, an internal buffer pool contribution may be applied. In various embodiments, the total deductions may be applied and credits may be determined. In various embodiments, credits at fine scale (e.g., field, sub-field, etc.) may be determined in part based on predictions from statistical or process models run on all land and all reporting periods (e.g., on all rows in the Zone Attribute Table described above). In various embodiments, those predictions may be scaled to equal the total emissions reduction obtained from the pre-stratified or post-stratified estimates. In various embodiments, certain credits may be attributed to fields. In various embodiments, certain credits may be attributed to time (e.g., years). In various embodiments, certain credits may be attributed to pairs of spatial units (e.g., fields, sub-field zones, pixels, etc.) and temporal units (e.g., years, growing seasons, cultivation cycles). In various embodiments, the results may be submitted to a carbon accounting system (CAS) and money may be transferred to the grower(s) who operate the land based on the determined carbon credits. In various embodiments, each post-stratum variance may be summed. In various embodiments, if Monte Carlo samples of post-stratum totals are available, post-stratum totals within each Monte Carlo draw may be summed and the variance of those Monte Carlo samples of the population total may be estimated.

Figure 4A:
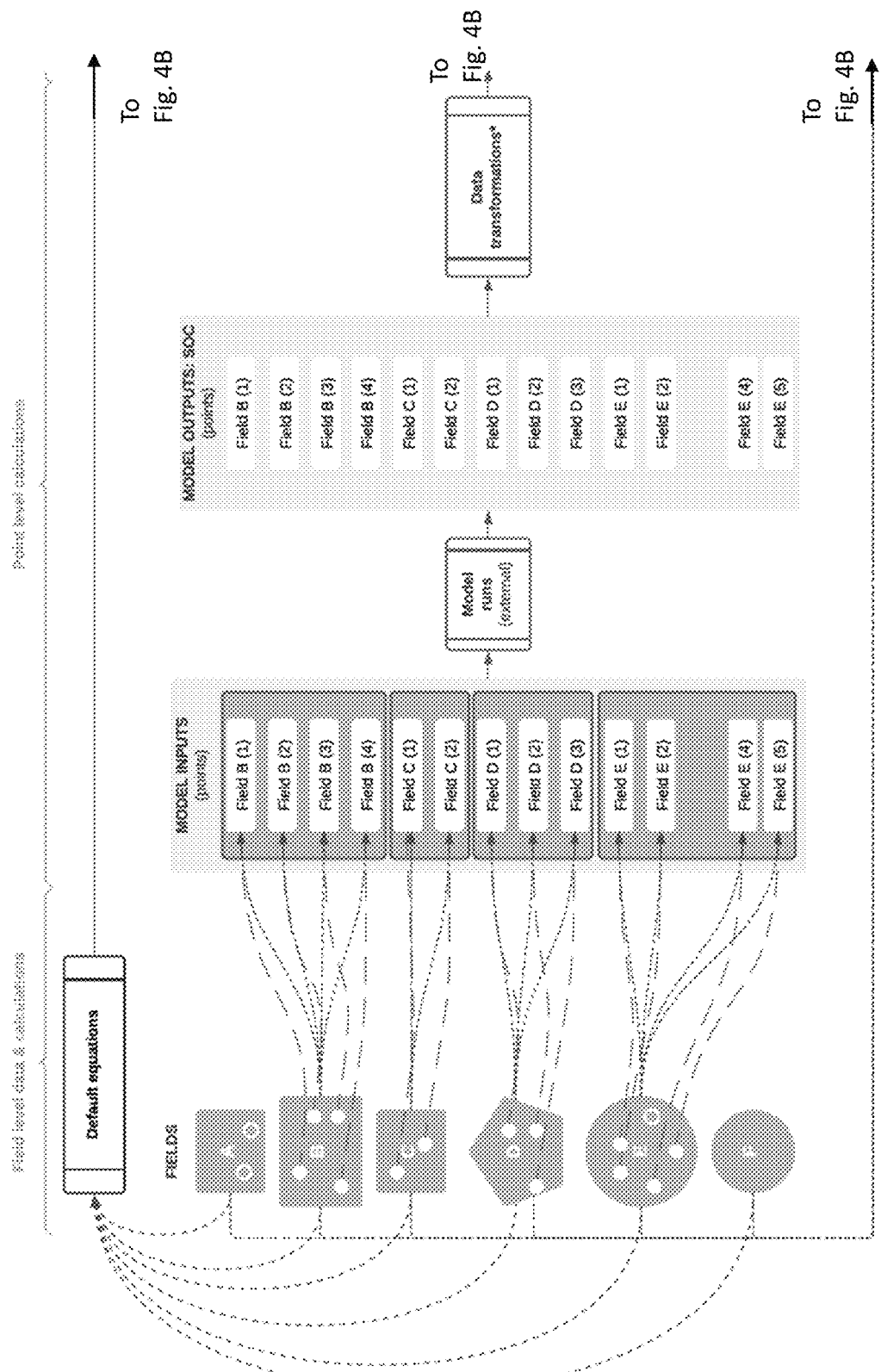
FIGS. 4A-4C illustrate a data flow diagram for estimating greenhouse gas emissions reduction according to embodiments of the present disclosure.
Figure 4B:
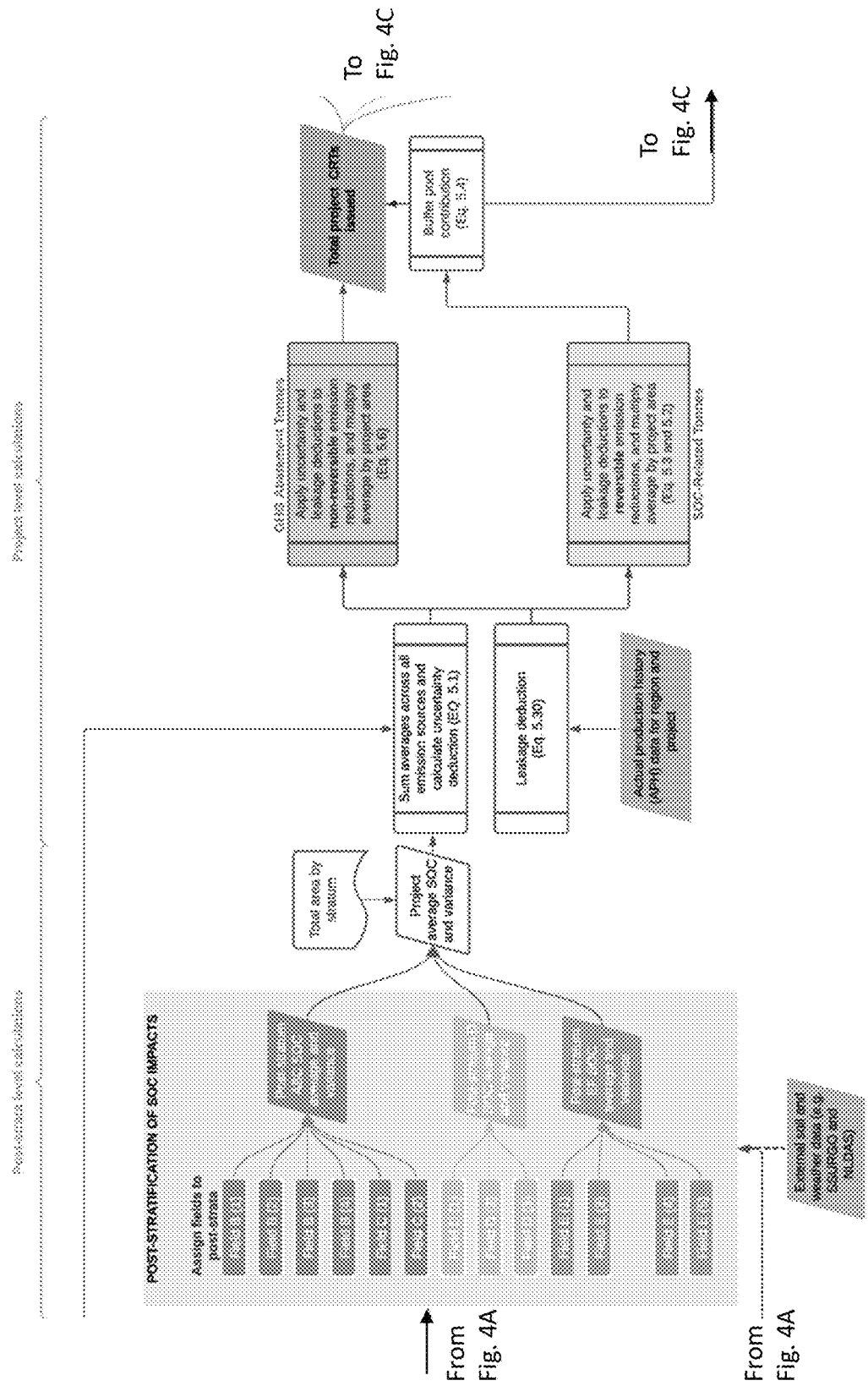
Figure 4C:
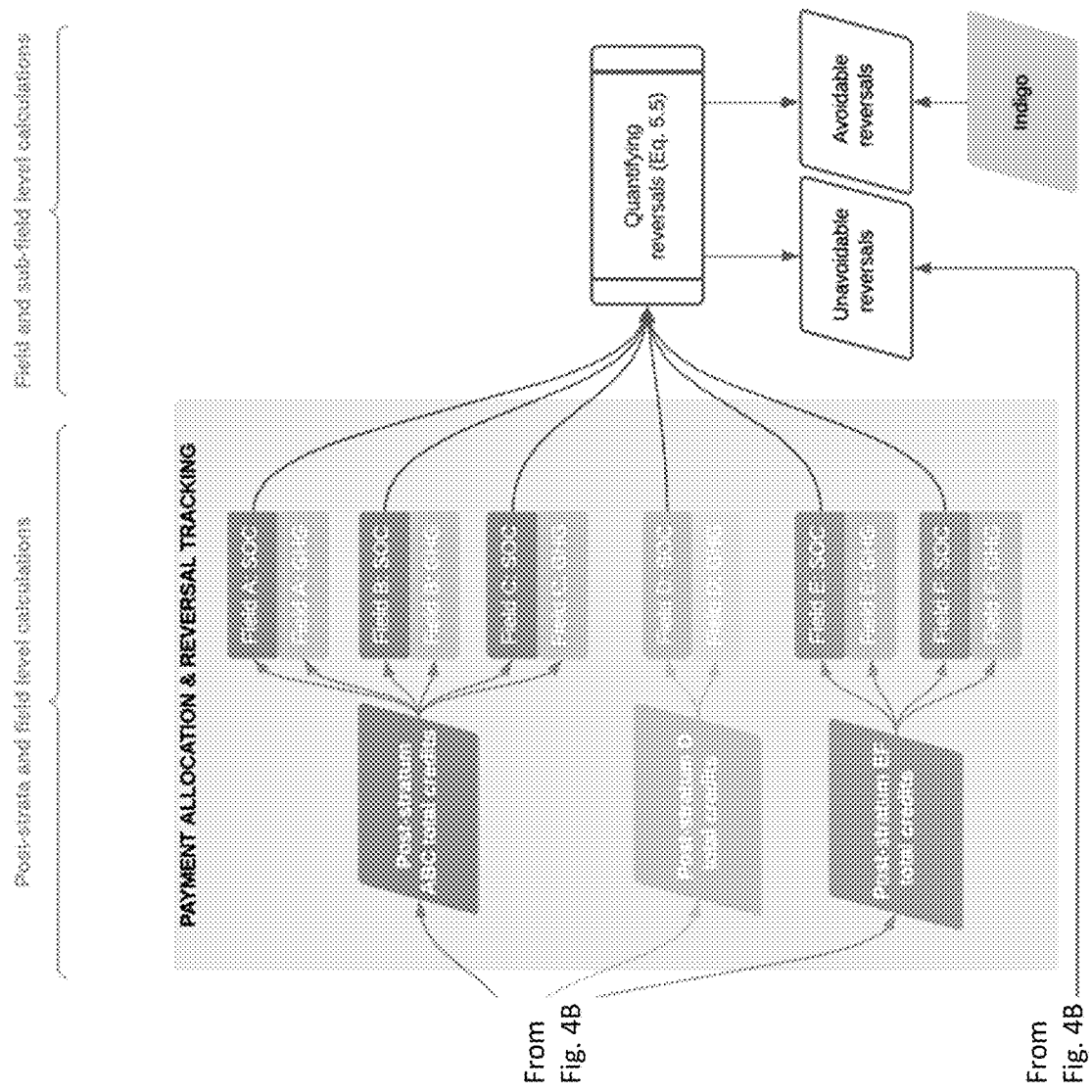

FIGS. 4A-4C illustrate a data flow diagram for estimating greenhouse gas emissions reduction. As shown in FIG. 4A, fields A-F are provided as field-level data. In various embodiments, the fields may include observed soil sample data points and/or missing soil sample data points. For example, field A is missing two soil sample data points, field B includes four observed soil sample data points, field C includes two observed soil sample data points, field D includes three observed soil sample data points, field E includes four observed soil sample data points and one missing soil sample data point, and field F includes no soil sample data points. In various embodiments, the observed soil sample data points are used as model inputs. In various embodiments, the fields may be grouped based on one or more variables. For example, as shown in FIG. 4B, fields B and C (and the associated observed soil sample data points) may be grouped into a post-stratum, field D may be grouped by itself as a post-stratum, and field E may be grouped by itself as a post-stratum. In various embodiments, the post-stratum including the observed data from a subset of fields may be used to represent other fields that are similar. For example, the post-stratum including fields B and C may be used to estimate emission reduction in fields A, B, and C. In another example, the post-stratum including field E may be used to estimate emission reduction in fields E and F.

In various embodiments, an average SOC may be determined from the observed soil sample data points and the average SOC may be applied to the total land area of all fields.

In various embodiments, total project credits may be determined as described above. In various embodiments, after total credits are applied to each post-stratum, the number of credits for each individual field may be determined. In various embodiments, the total credits may be split evenly among the fields. In various embodiments, the total credits may be split among the fields based on land area of each field. In various embodiments, the total credits may be split among fields based on weights equal to the predictions of emissions reduction on small spatial scales (e.g., field, sub-field zone).

Figure 5:
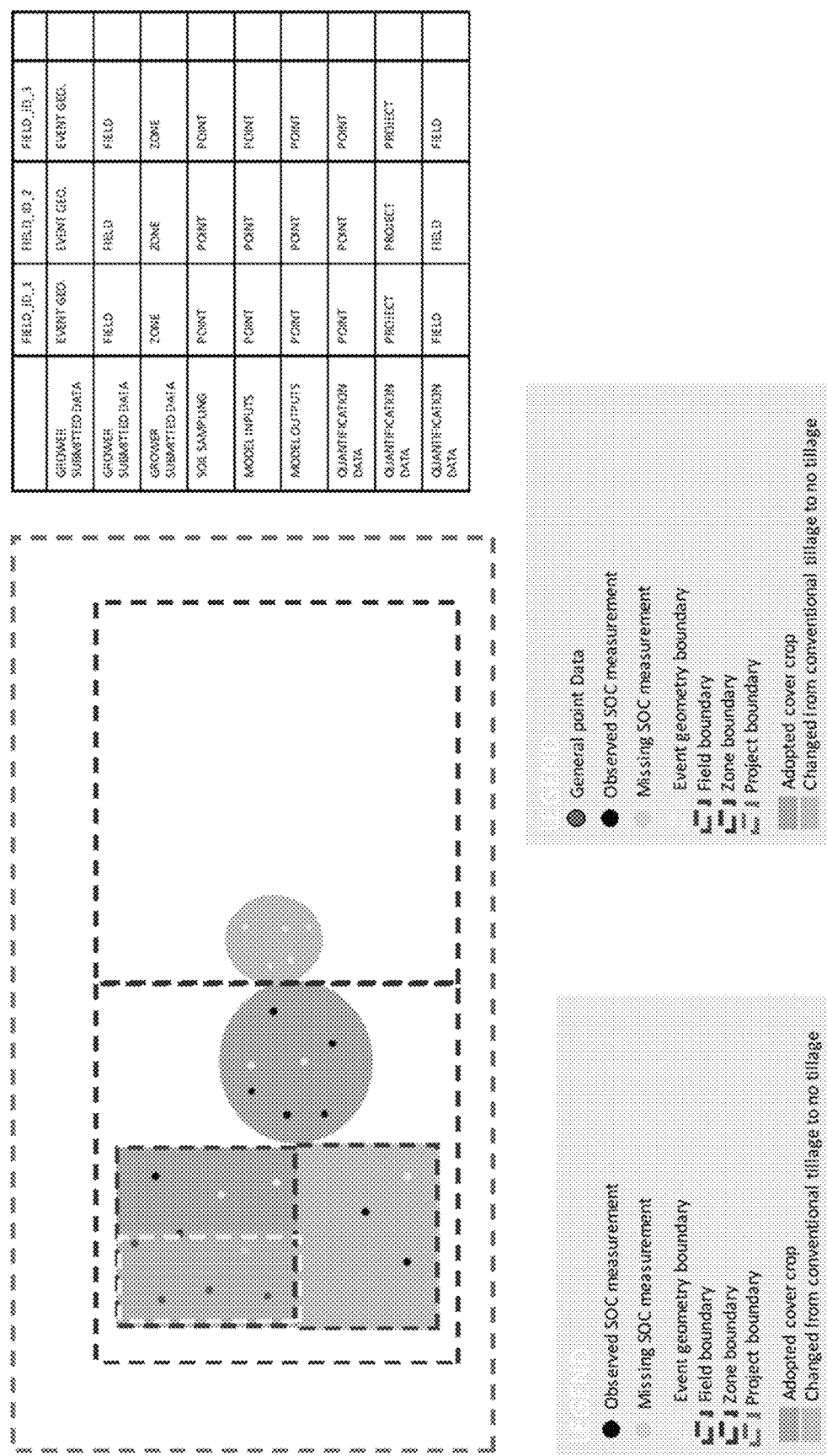
FIG. 5 illustrates an exemplary partition of a project into zones, fields, and events according to embodiments of the present disclosure.

FIG. 5 illustrates an exemplary partition of a project into zones, fields, and events. In various embodiments, zone boundaries may be defined by the intersection of all event geometries. In various embodiments, the boundaries (e.g., all boundaries) may be defined by the grower. In various embodiments, the grower may draw boundaries on a map (e.g., through an app or desktop web application) to designate the edge of their fields. In various embodiments, the grower may draw boundaries on the map to indicate event geometries, for example, where they planted certain crops, applied fertilizer, etc. In various embodiments, by intersecting the event geometries, land may be identified on which the expected SOC change would likely be similar. For example, a farmer may have planted soy on the western side of the field and wheat on the eastern side. In this example, the soy and wheat crops may be represented as two different event geometries, which would partition the field into two zones. In forming post-strata, zones may be used as the basic units, i.e., each zone may be assigned to one and only one post-stratum. In various embodiments, zones may be further split into smaller units by doing a spatial join with other datasets (e.g., weather data, regional soil database, topographic data).

Figure 6:
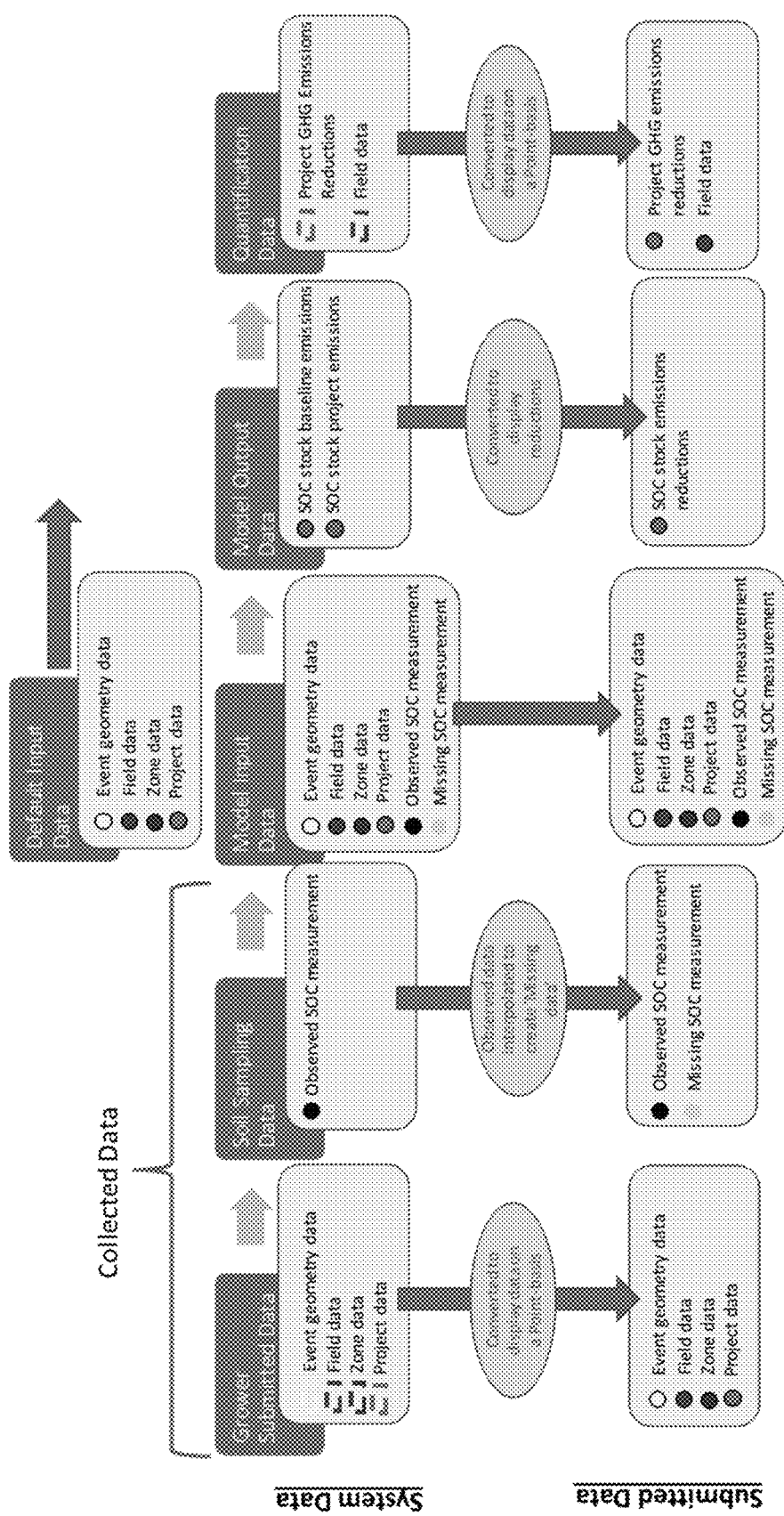
FIG. 6 illustrates a flow diagram of collected data, modelling, and quantification according to embodiments of the present disclosure.

FIG. 6 illustrates a flow diagram of collected data, modelling, and quantification.

Figure 7A:
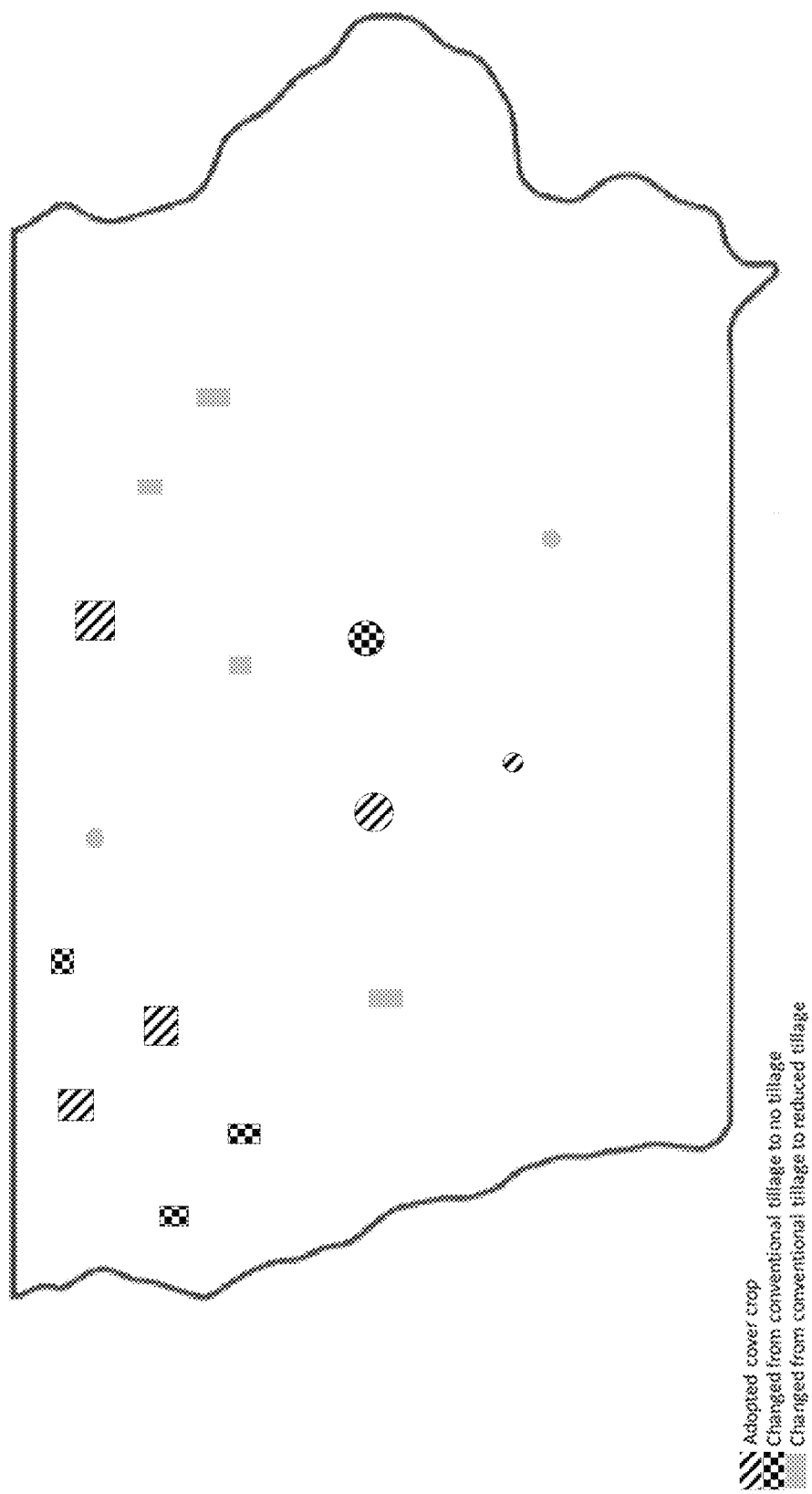
Figure 7B:
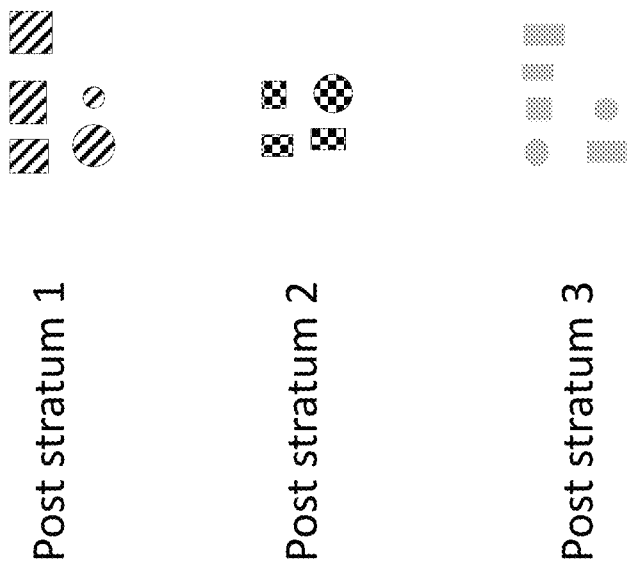
Figure 7C:
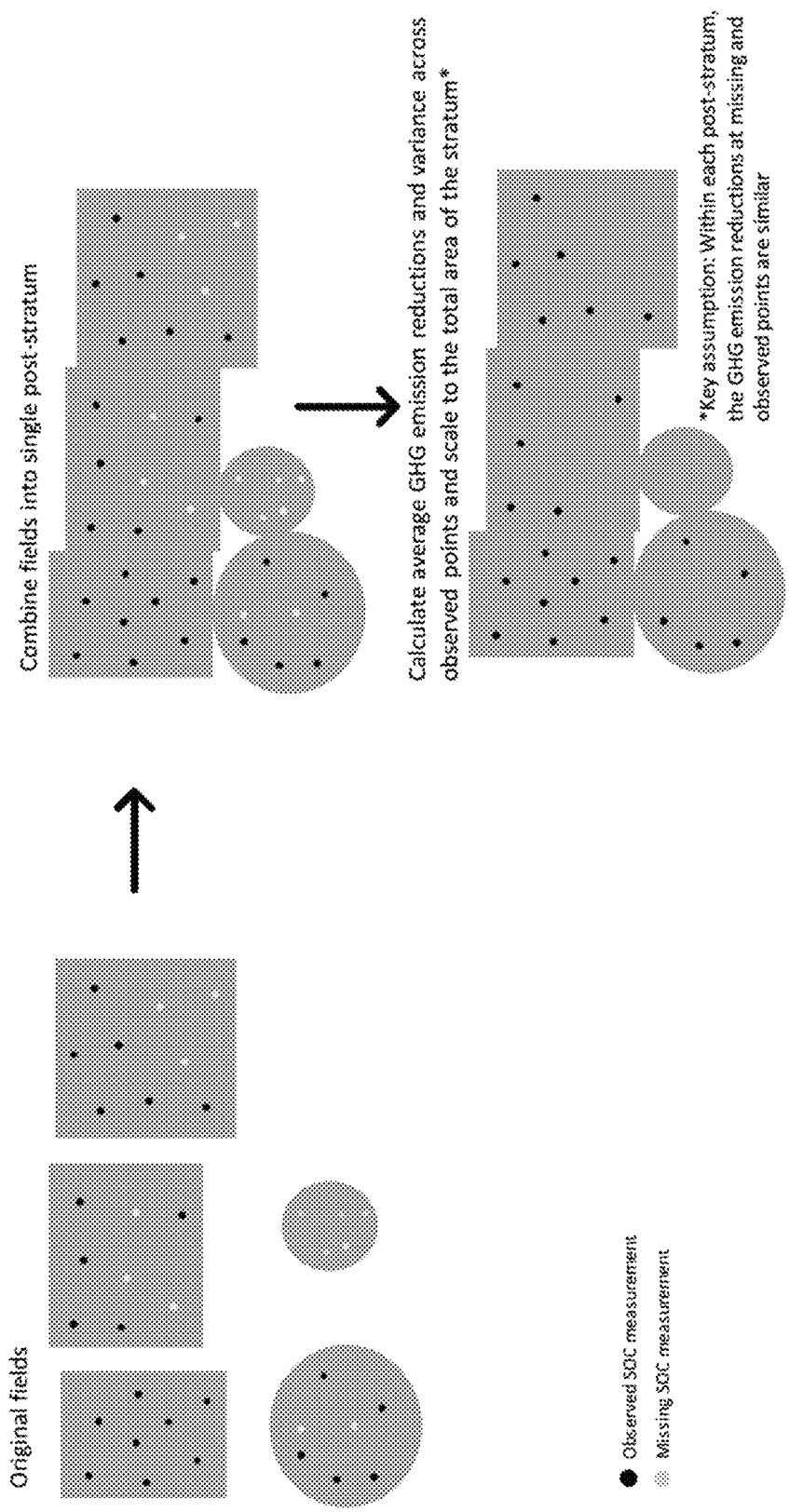

FIGS. 7A-7D illustrate exemplary post-strata grouping and total greenhouse gas emissions reduction. In particular, FIG. 7A illustrates various hypothetical fields in a particular land region (e.g., Iowa) where some fields adopted cover crop land management practices, some fields changed from conventional tillage to no tillage, and some fields changed from conventional tillage to reduced tillage. As shown in FIG. 7B, the regions are grouped into three post-strata based on land management practices, even though in some cases the fields within the same post-stratum may be distant from one another. FIG. 7C illustrates the process of combining the original fields into a single post-stratum, determining an average greenhouse gas emissions reduction and variance across areas with observed values within the post-stratum, and applying the average across the entire post-stratum (including in areas with missing or incomplete data) to thereby estimate GHG emissions reduction and variance for the entire post-stratum. FIG. 7D illustrates the calculation of total GHG emissions reduction and variance for each of the three post-strata as well as the total GHG emissions reduction and variance for the entire project.

In various embodiments, post-stratification may reduce bias and variance. In various embodiments, if GHG emission reductions at missing and observed points are similar within post-strata, then post-stratification may reduce bias because emission reductions at observed points can stand in for emissions reduction at missing points, and may reduce variance because emission reductions within a stratum do not vary as much as across an entire project (e.g., an entire land region).

Figure 8A:
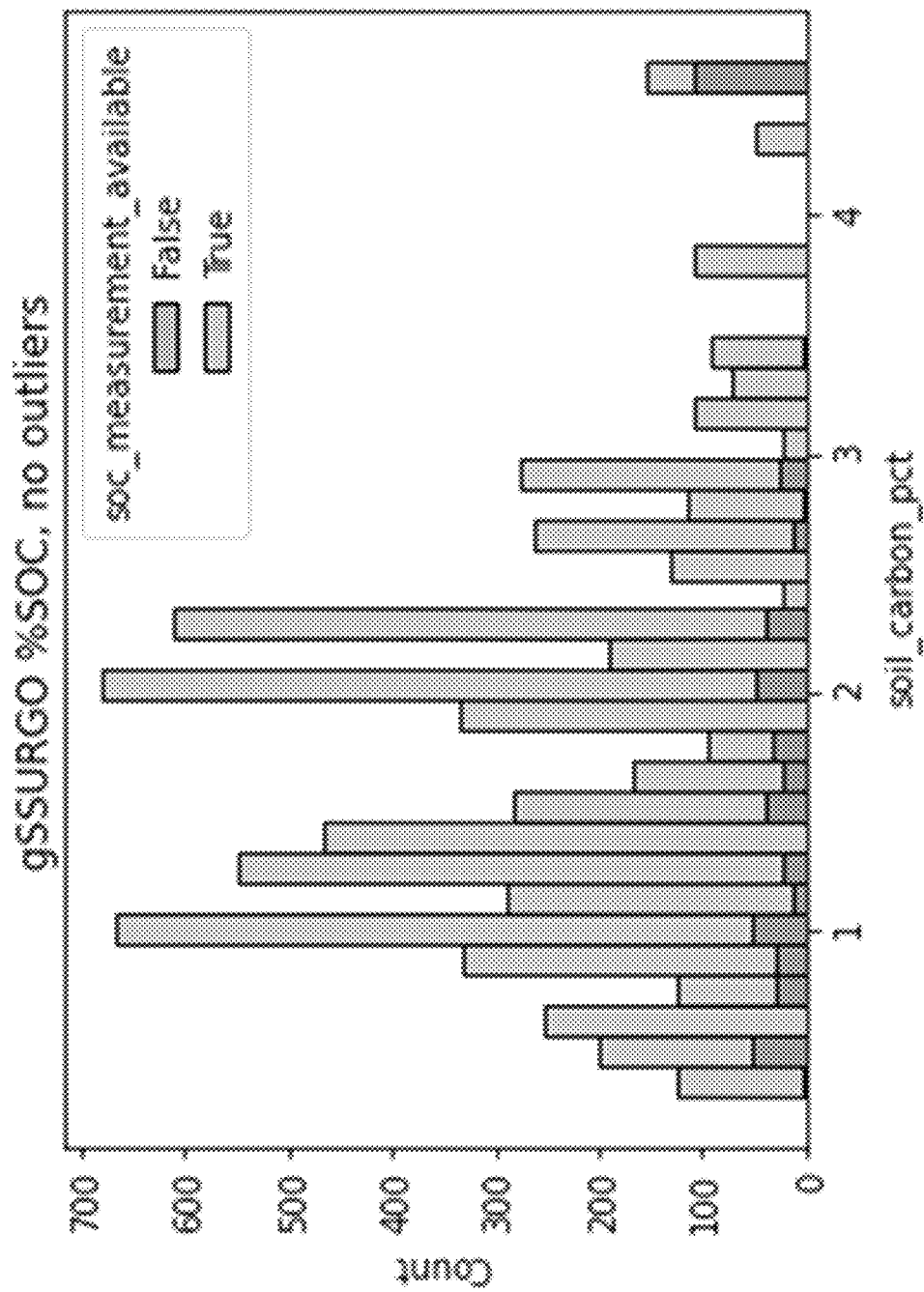
FIGS. 8A-8B illustrate graphs of soil organic carbon from soil databases according to embodiments of the present disclosure.
Figure 8B:
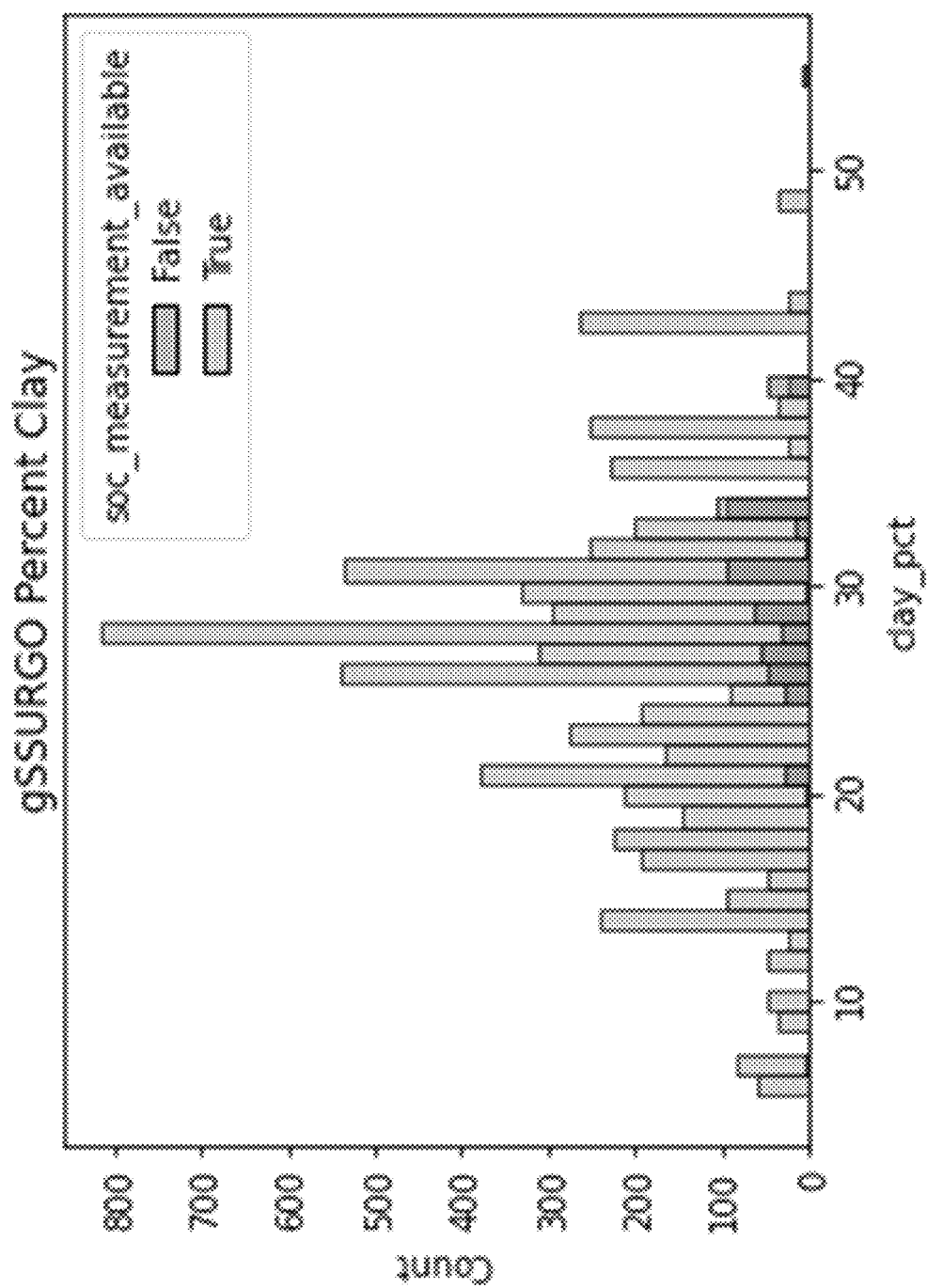

FIGS. 8A-8B illustrate graphs of soil organic carbon from soil databases. In various embodiments, survey response may be a common problem. In various embodiments, in a first step to determine non-response/missingness, a percent missing may be determined. In various embodiments, in a second step to determine non-response/missingness, reasons for missing soil samples may be collected and counted. In various embodiments, in a third step, a standardized mean difference (SMD) may be determined for characteristics that might impact emissions reductions. In various embodiments, the SMD may be determined as a difference between an average for points with observed % SOC and an average for all points all divided by a pooled standard deviation. In various embodiments, the absolute SMD may be compared against a predetermined threshold, such as 10%, 25%, or another suitable percentage for a project. As shown in FIG. 8A, the strata B1 has a small absolute SMD and overlapping distributions. As shown in FIG. 8B, the strata B2 has a moderate absolute SMD and less overlap in the distribution.

In various embodiments, response propensity may be used to define post-strata. In various embodiments, a predictive model (e.g., logistic regression) may be fit to the response data (e.g., % SOC observed (Yes/no)~LRR+{gSSURGO % soc}+ ... ). In various embodiments, predicted probabilities may be computed for all points in the PAT. In various embodiments, a predictive model (e.g., linear regression, regression trees, gradient boosting, etc.) may be fit to the emissions reduction data (e.g., emissions reduction~LRR+{gSSURGO % soc}+ ... ). In various embodiments, the emissions reduction in the regression is obtained from measurements of emissions. In various embodiments, the emissions reduction in the regression is obtained from a model (such as a biogeochemical model or a statistical model). In various embodiments, post-strata may be implemented based on response probability. For example, post-strata may be defined by response probability less than 0.8, response probability between 0.8 and 0.9, and response probability above 0.9. In various embodiments, post-strata may be formed based on the predicted means of the regression model for emissions reduction (e.g., land and time with predicted mean <0 are one post-stratum; land and time with predicted mean >0 are another post-stratum). In various embodiments, post-strata may be formed from a cross-tabulation of the response probabilities and the predicted means of the emissions reduction model (e.g., one post-stratum is all land and time with response probability <80% and predicted mean >1).

Figure 9A:
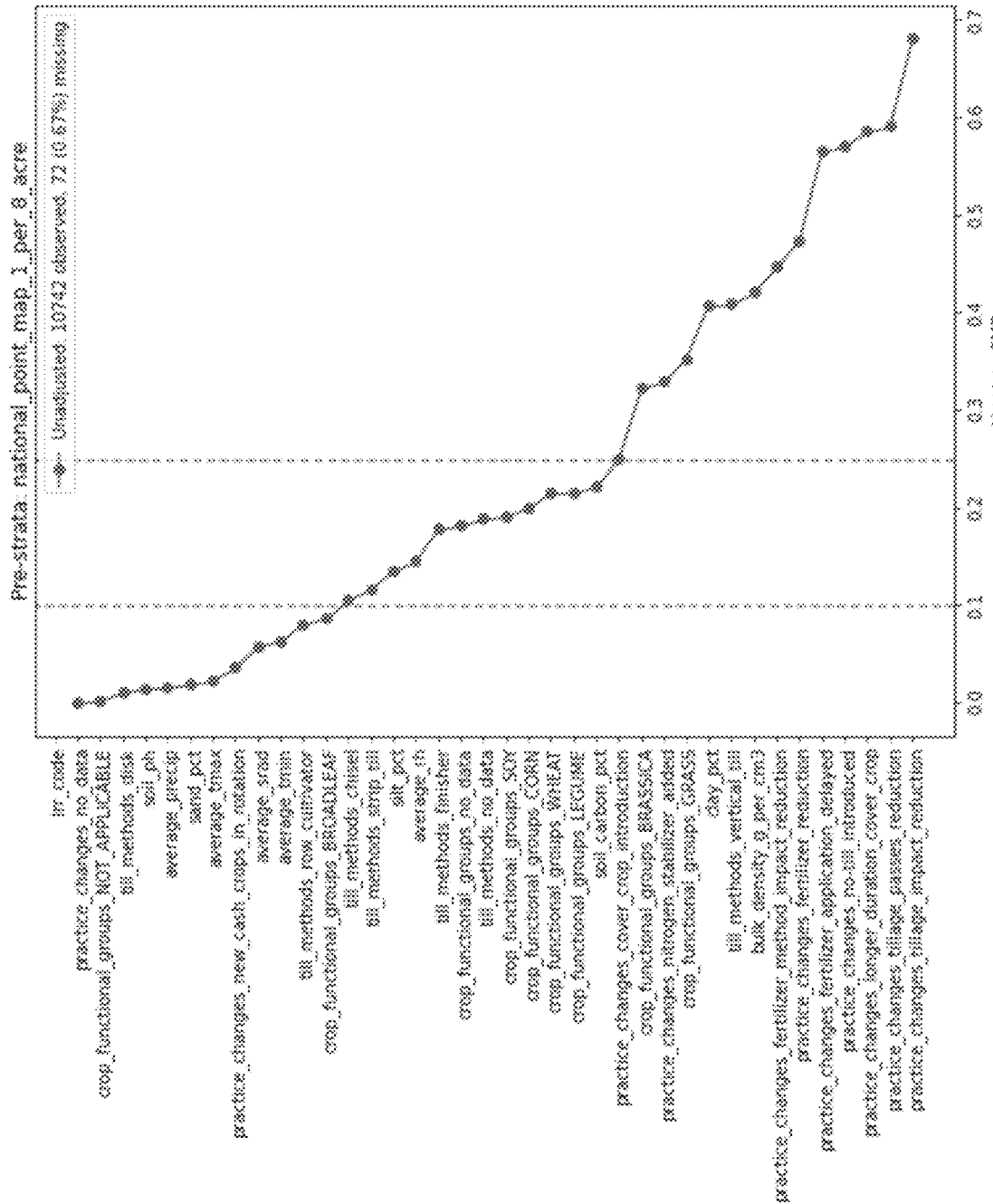
FIGS. 9A-9B illustrate Love plots with various characteristics for strata A and B according to embodiments of the present disclosure.
Figure 9B:
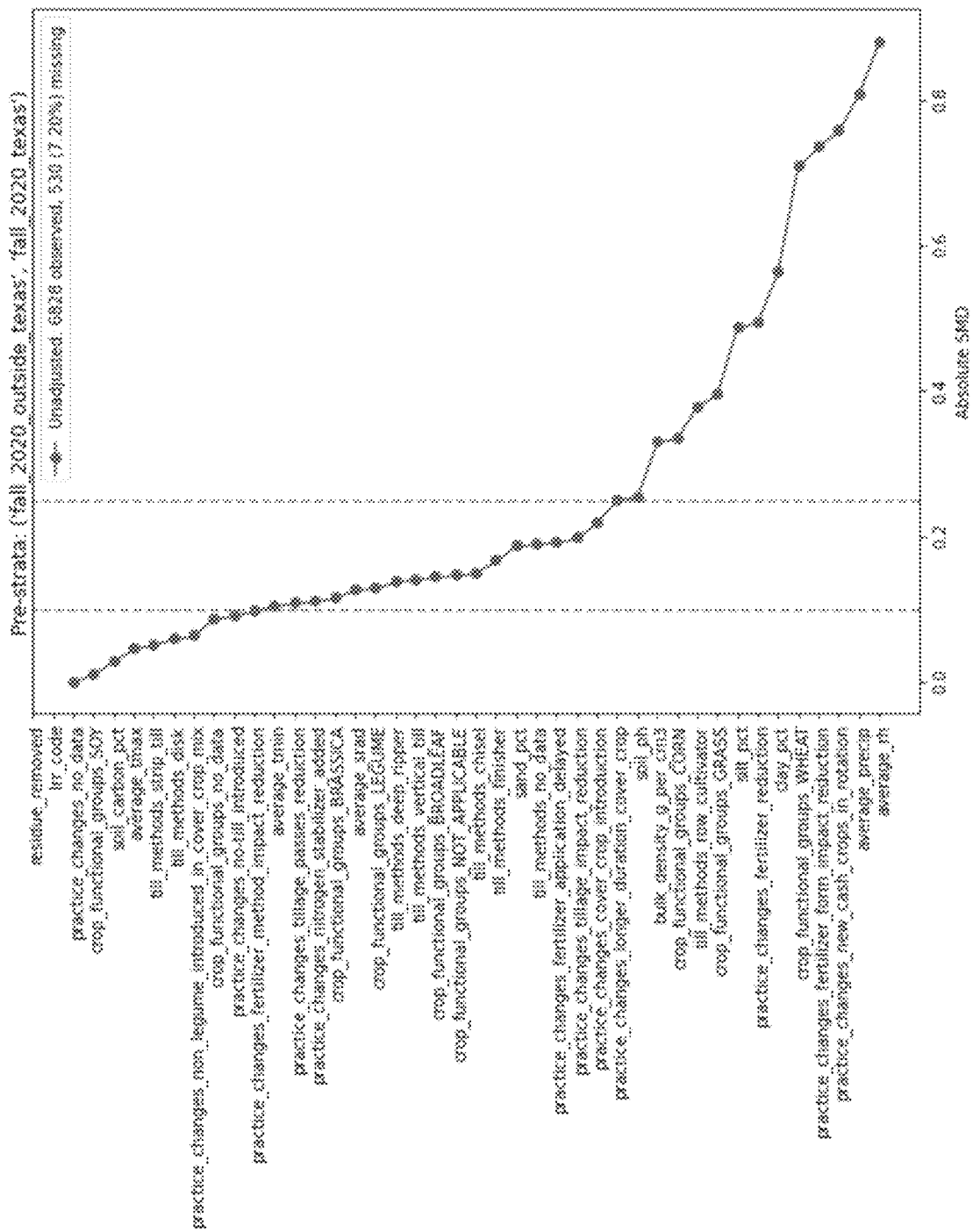
Figure 9C:
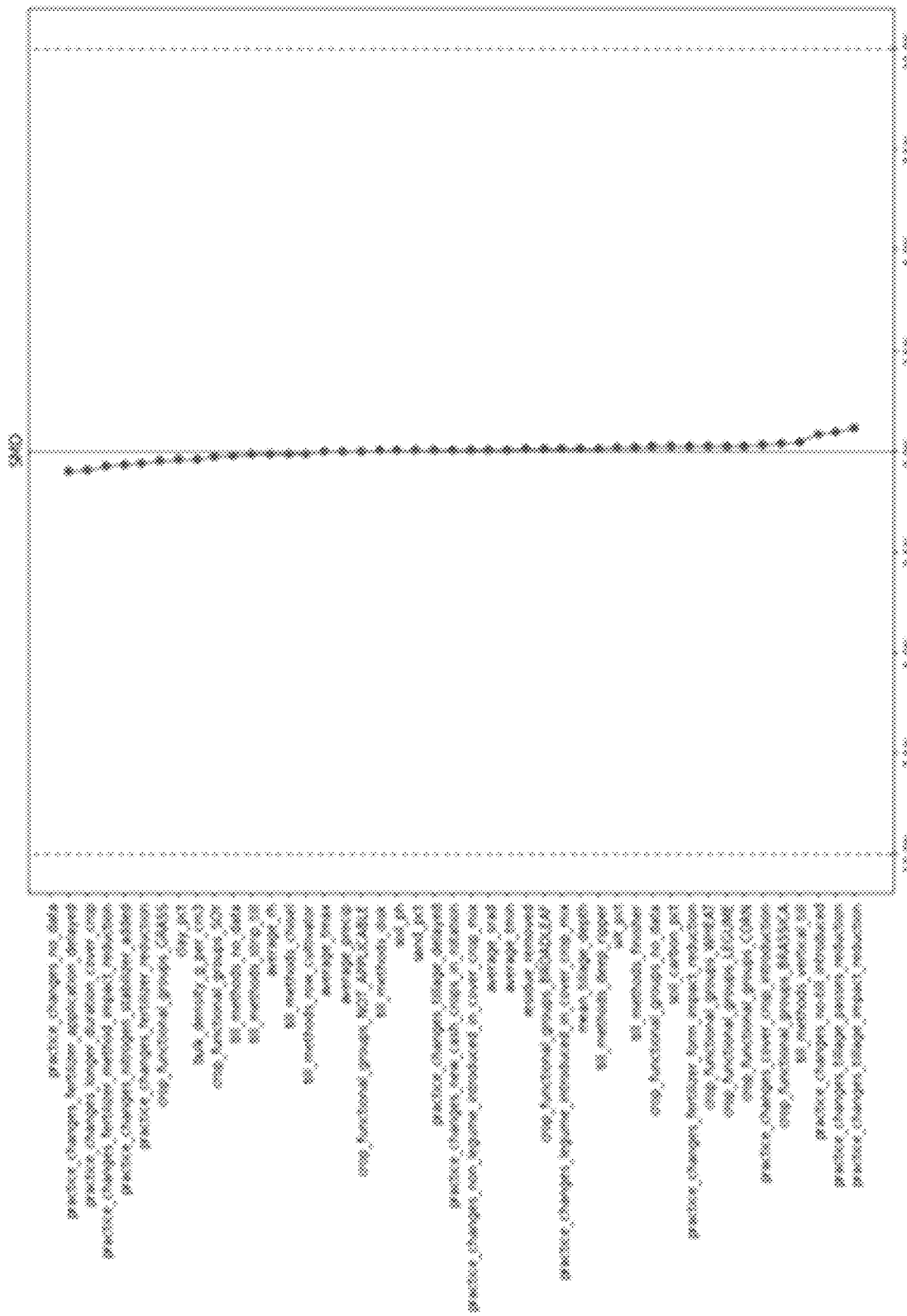
FIG. 9C illustrates standardized mean differences (SMD) in a pre-stratum using a new formula according to embodiments of the present disclosure.

FIGS. 9A-9B illustrate Love plots with various characteristics for strata A and B. Each row in FIGS. 9A-9B correspond to an attribute that is potentially associated with emission reductions, and the x-axis shows the standardized mean difference (SMD). In various embodiments, the attributes on the y-axis may be restricted to variables that are known for all fields in the project (e.g., soil attributes from gSSURGO may be listed on the y-axis, whereas laboratory measurements of % SOC may not be listed on the y-axis). In various embodiments, the SMD may compare the distribution of each attribute among all points vs points at which % SOC is observed. As shown in FIGS. 9A-9B, the vertical dashed lines indicate commonly used thresholds for assessing covariate balance; points to the left of the lines are acceptable, whereas points to the right of the lines may indicate potential bias. FIG. 9C illustrates SMDs in pre-stratum A using the new formula as described above.

Figure 10:
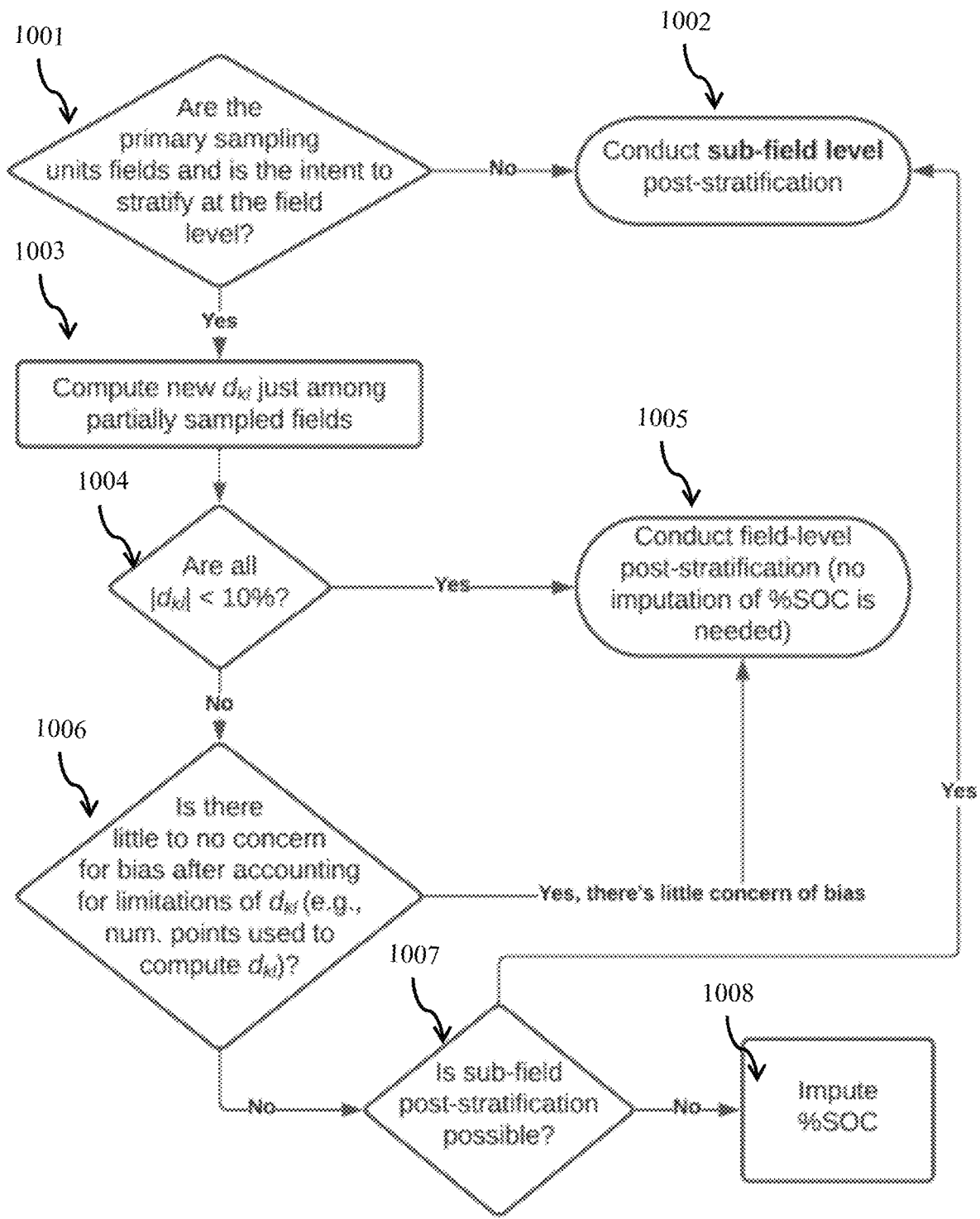
FIG. 10 is a flowchart illustrating an exemplary process for determining whether imputation of the concentration of soil organic carbon (% SOC) is necessary according to embodiments of the present disclosure.

Referring to FIG. 10, a flowchart is provided illustrating an exemplary process for determining whether imputation of % SOC is necessary. At 1001, it is determined whether the primary sampling units fields and whether the intent is to stratify at the field level. If not, sub-field level post-stratification is conducted at 1002. If so, an new $d_{kl}$ is computed among partially sampled fields at 1003. If all $|d_{kl}|<10\%$ (1004) then field-level post stratification is conducted at 1005 (without the need for imputation of % SOC). If not, and if there is little concern for bias after accounting for limitations of $d_{kl}$ (1006), then field-level post stratification is conducted at 1005 (without the need for imputation of % SOC). If there is concern for bias, it is checked whether post-stratification is possible at 1007. If so, then sub-field level post-stratification is conducted at 1002. If not, then % SOC is imputed at 1008.

Figure 11A:
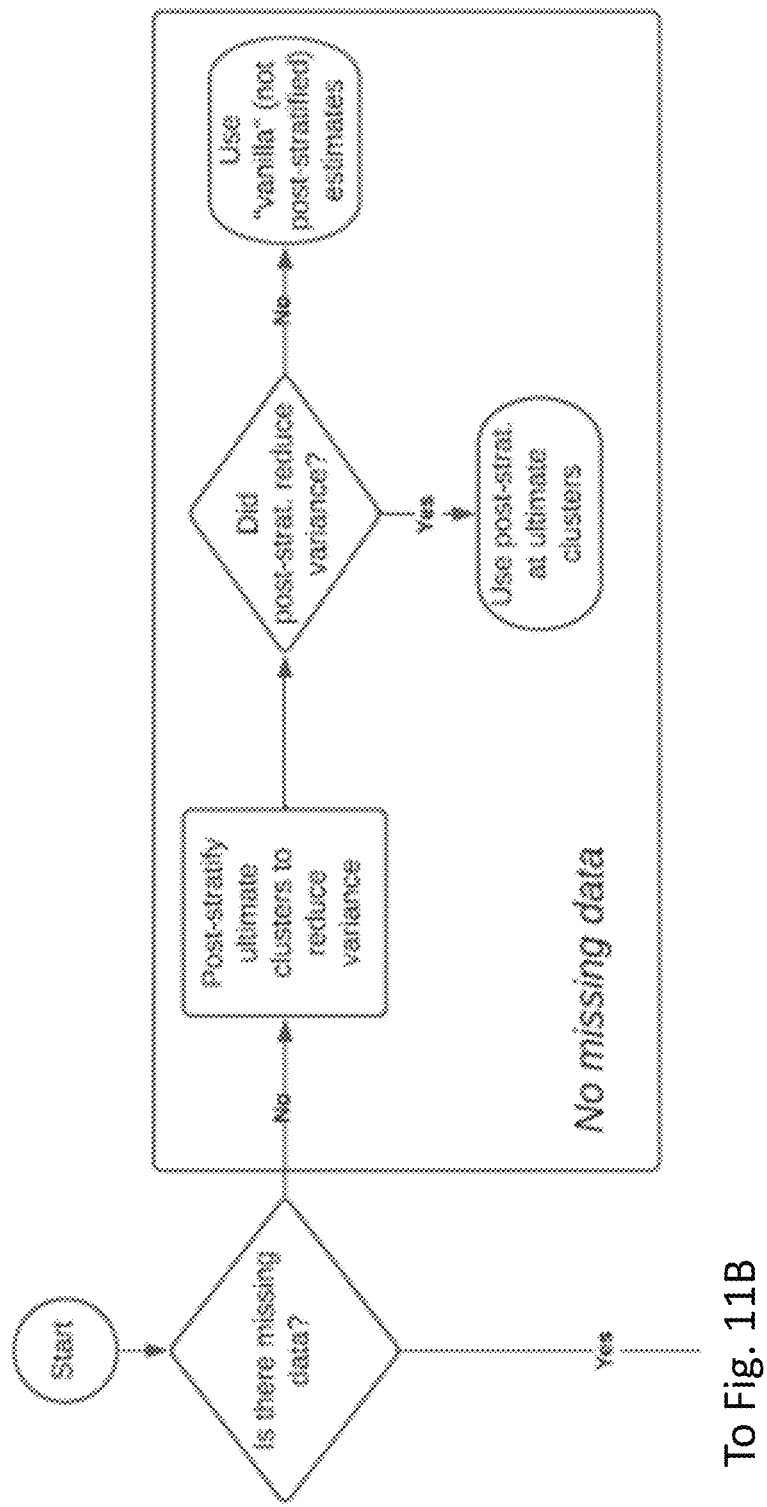
FIGS. 11A-E is a decision flow with regard to estimation strategy according to embodiments of the present disclosure.
Figure 11B:
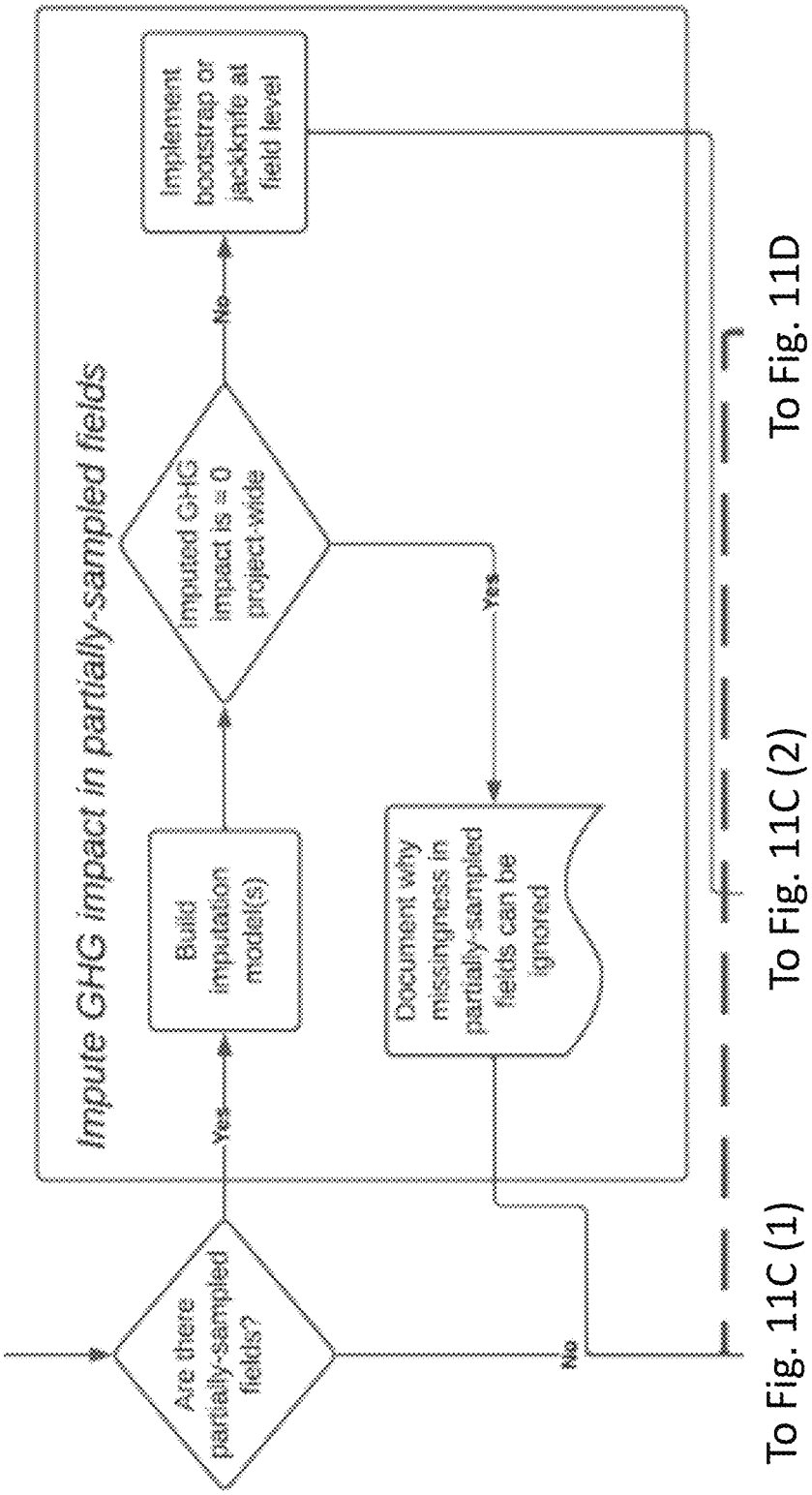

Referring to FIGS. 11A-E, a decision flow with regard to estimation strategy is illustrated. Referring to FIG. 11A, where no data are missing, post-stratification estimates are generated ad then used if it results in a reduction in variance. Referring to FIG. 11B, GHG impact is imputed if there are partially-samples fields. An imputation is model is built, and then bootstrap or jackknife methods as set out above are implemented at the field level if the imputed impact is not zero. This approach may be preferred over post-stratifying points if the missing points tend to be unlike those in their stratum.

Figure 11C:
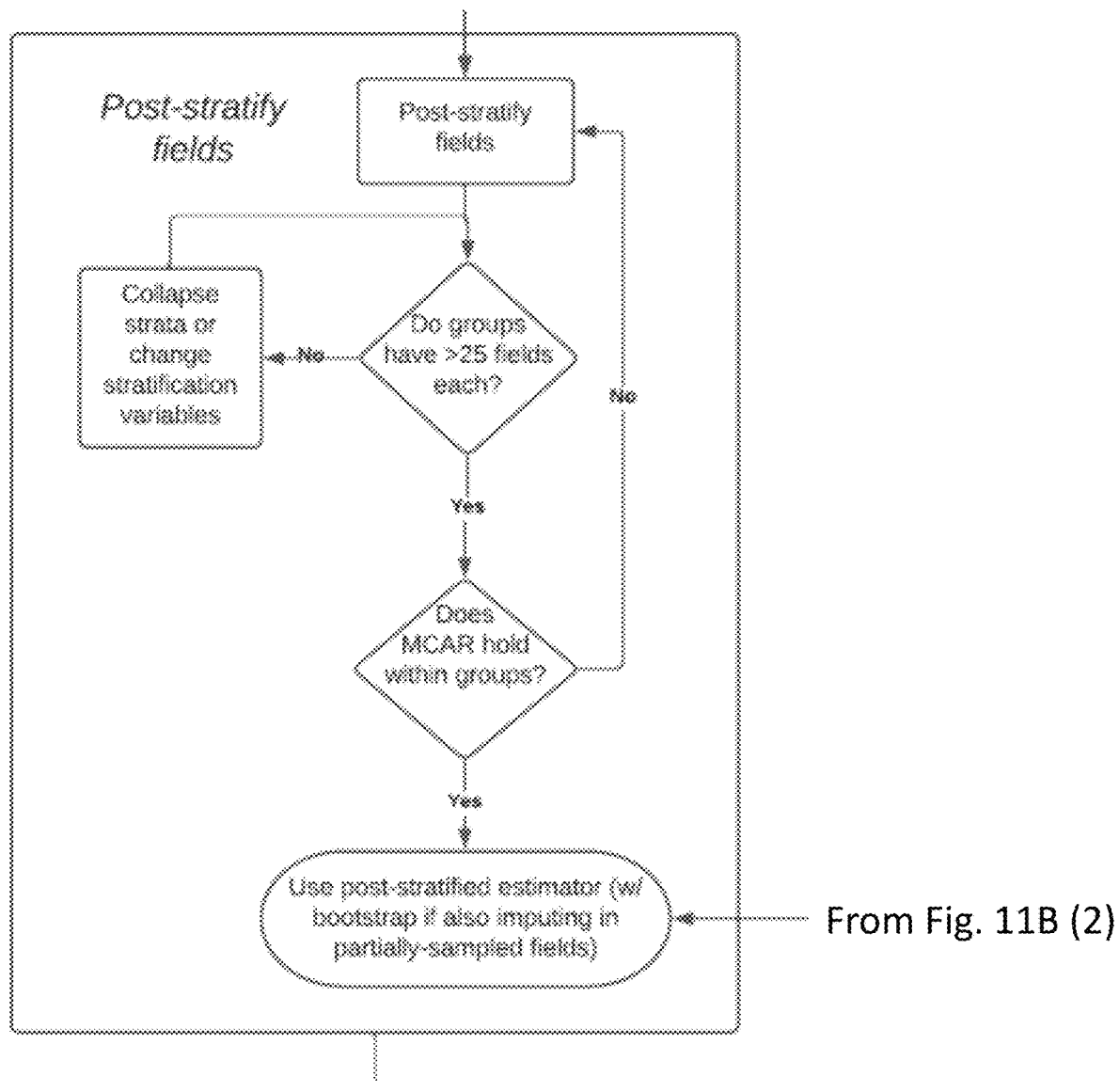
Figure 11D:
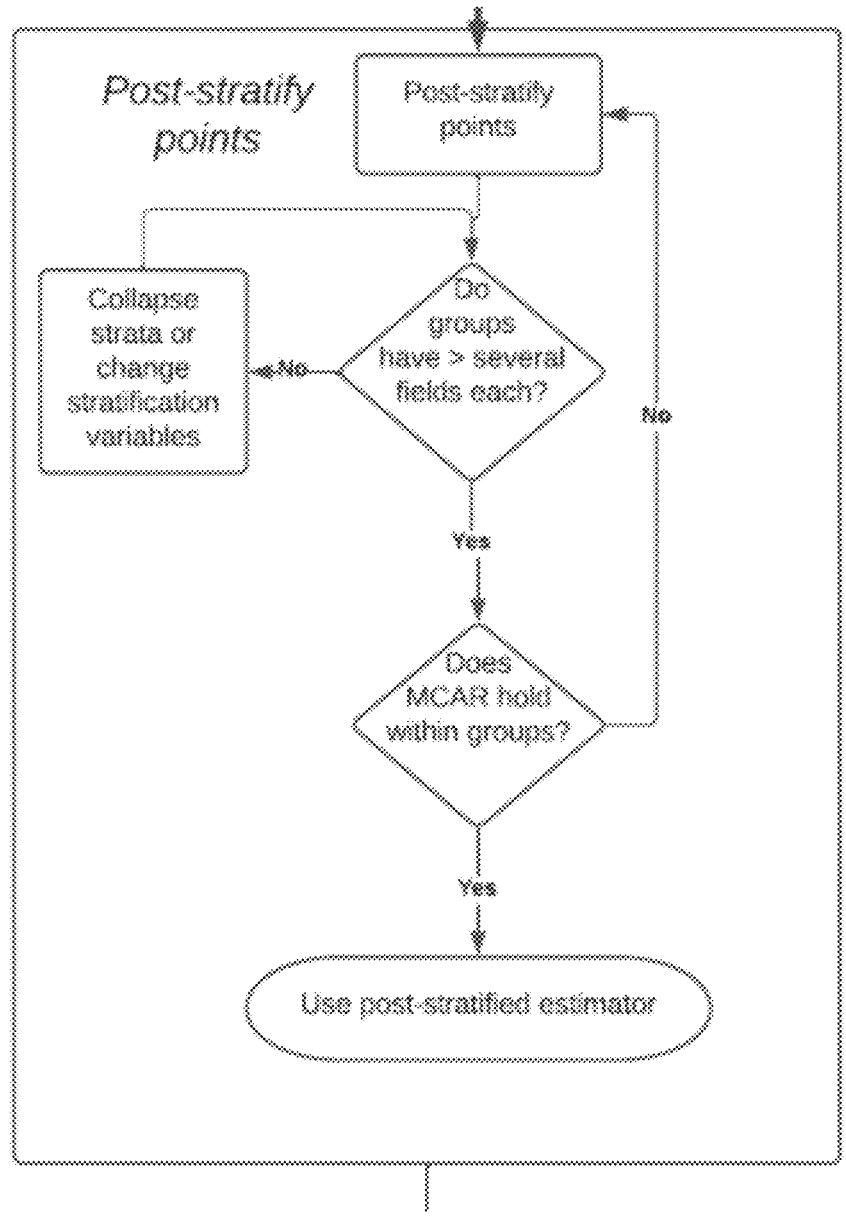
Figure 11E:
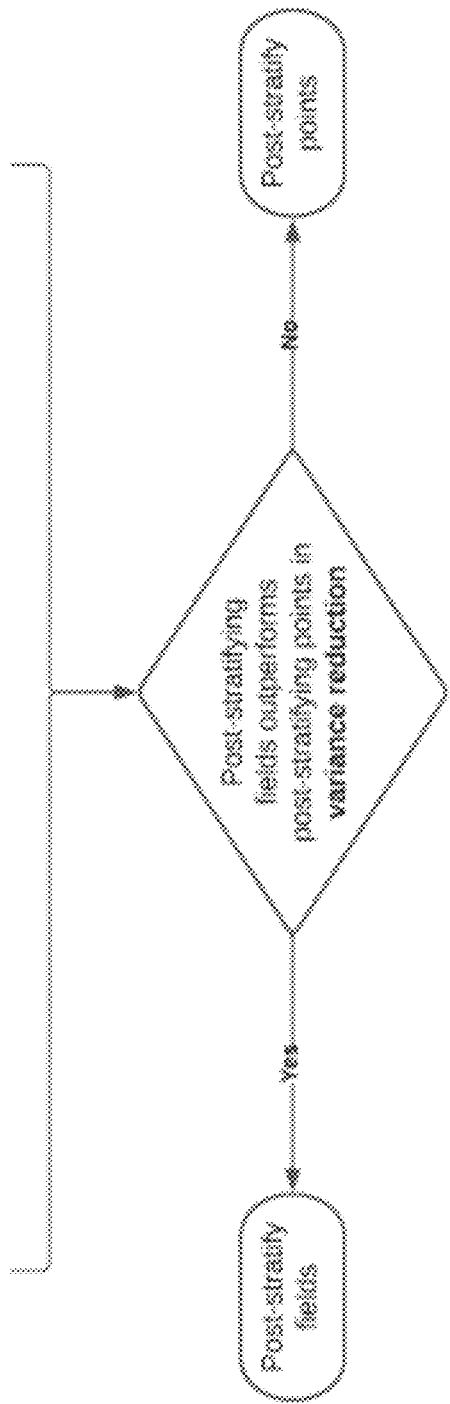

Referring to FIGS. 11C-D, where data are missing and there are not partially-sampled fields, post stratification of fields (FIG. 11C) and of points (FIG. 11D) is performed as set forth above. Post-stratifying fields has simpler requirements for sub-field data, but may need imputation for partially-sampled fields. Post-stratifying points yields potentially better results, but quality sub-field event data is important. Referring to FIG. 11E, the method yielding the best performance in terms of variance reduction is selected.

In various embodiments, cultivation cycles may be defined as the periods over which field-level emissions are estimated in the project scenario. In various embodiments, a field's earliest cultivation cycle begins on the field's start date. In various embodiments, crop growing seasons may be used as building blocks to construct cultivation cycles. In various embodiments, the initial reporting period may comprise either one or more cultivation cycles. In various embodiments, a cultivation cycle for a field may generally be defined as the period between the first day after harvest of the last crop on a field in the previous reporting period and the last day of harvest of the last crop on a field during the current reporting period. In various embodiments, the first cultivation cycle for each field is the cultivation cycle in which additionality is met. In various embodiments, a field's first cultivation cycle may start after the end of the last completed crop growing season. In various embodiments, in subsequent reporting periods, if a field has already been included in a prior reporting period then a field's cultivation cycle will start after the end of the last cultivation cycle included in the previous reporting period. In various embodiments, the length of the cultivation cycle may vary from year to year, depending on weather and the overall crop and management rotation schedule. In various embodiments, a cultivation cycle may be greater or less than a calendar year, and may include multiple crop growing seasons, including cash crops crowing seasons, cover crop growing seasons, perennial crop growing seasons, and fallow period crop growing seasons. In various embodiments, although reporting periods may typically comprise only one cultivation cycle, the initial reporting period may comprise multiple cultivation cycles. In the initial reporting period, a field's cultivation cycles may include all crop growing seasons after the cultivation cycle start.

In various embodiments, crop growing seasons may be the building blocks of cultivation cycles and of baseline threads. In various embodiments, the purposes of crop growing seasons include: discretize continuous management in a field into logical time periods with clear start and end dates; create discrete, continuous, and non-overlapping periods of time over which emissions can be estimated; and enable the construction of clear and logical cultivation cycles and baseline threads. In various embodiments, guiding principles used to define crop growing seasons include: crop growing seasons should be defined by management events, specifically harvest events when possible; crop growing seasons should partition every field's entire reporting history, without gaps; crop growing seasons should create periods of time less 12 months, even for perennial crops; and crop growing seasons may include all of the required definitions for cultivation cycles and baseline threads. In various embodiments, determining the start date of each crop growing season is sufficient to define all crop growing seasons in a field's management history. In various embodiments, since crop growing seasons are continuous across a field's reported management history, the end date of a crop season is simply the day before the start date of the subsequent crop growing season.

Figure 12:
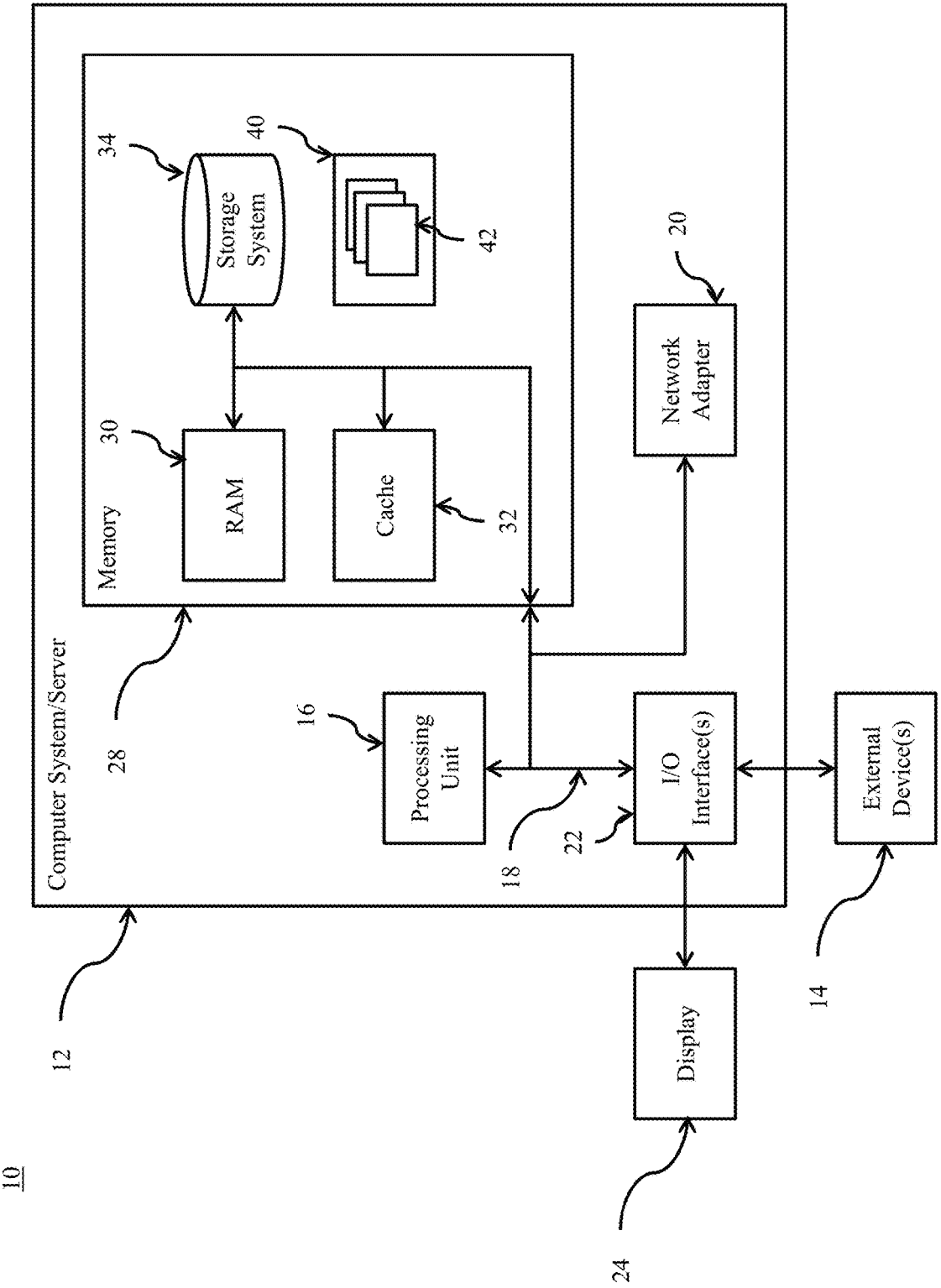
FIG. 12 depicts an exemplary computing node according to embodiments of the present disclosure.

Referring now to FIG. 12, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 12, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In various embodiments, methods, systems, and computer program products described herein may apply to estimates of global quantities in space, time, or spacetime. For example, such a quantity could be emissions reduction or emissions, stock(s) of carbon, stock(s) of woody biomass, and/or the like. More generally, such a quantity may be any quantity X that may answer the questions "how much of X is in this land?" or "what's the average of X across this line and this range of time?" Although various embodiments herein refer to The SOC and soil measurement, the measurements may also be applied more broadly without departing from the scope and spirit of what is described herein. For example, within the GHG emission context, the various embodiments may be applied to measurements of N2O and CH4, including via eddy-covariance stations (which may also be referred to as eddy-covariance flux towers), via static chambers, and/or the like. The methods, systems, and computer program products described herein may be operate on or in conjunction with one or more computing nodes. The methods, systems, and computer program products described herein may operate faster, more efficiently, and be more robust than conventional systems and techniques. Thus, the methods, systems, and computer program products that operate on or in conjunction with one or more computing nodes may allow for the faster, more efficient, and more robust operation of the one or more computing nodes. In various embodiments, methods, systems, and computer program products described herein may make use of a computing node because the number of potential permutations and/or combinations of data during data processing and/or analysis may grow extremely large. For example, a computing node may have to be used when combining pre-strata. In some large projects with multiple strata, for example, any data processing or data analysis will have to be done using a computing node. In various embodiments, for a typical project, the monitoring of soil carbon stocks may require hundreds or thousands, if not more, of samples, due to the large spatial variability of soil carbon and the measurement errors involved. For example, gathering the data on all sample locations for SMD formula analysis may require the use of a computing node. To compute such SMDs, information that is known about all the planned sample points may have to be collected. Such information may include data regarding the weather, soil properties, management, and the like. Even for collection of samples and information from a few eddy covariance towers, for example, the data retrieval task, without the use of a computing node would be infeasible and would be tedious and error-prone. In addition, because of the size of this data/information and access to the data/information in various databases, performing the SMD formula analysis would require a computing node.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

APPENDIX A

Appendix A: Abstract

This Appendix provides examples how various embodiments of the present disclosure were used to impute bulk density, soil pH, and texture at sample points.

In some examples, because of the costs and lower variability of the bulk density, pH, and texture soil attributes, these attributes were measured at a random subset of points (and, in the case of pH and texture, using composite samples). Geostatistical techniques were used to estimate those measurements at sample points. This Appendix provides detailed examples of how this imputation satisfied the at least some of the requirements for imputing soil measurements as described with respect to various embodiments above.

Appendix A: 1 Introduction

As described above, the soil measurements may and sometimes must be taken at randomly selected locations (points) according to a sample design with the aim of collecting a representative sample of soils. The biogeochemical models estimated emissions reduction at each sampled point. In accordance with various embodiments described herein, bulk density, pH, and texture may be measured at a random subset of points where % SOC is measured because these attributes may be expensive to take, may lead to more injuries to soil samplers (in the case of bulk density), and/or may vary less within fields than % SOC does. At points where these measurements may be missing—either deliberately so (e.g., to reduce costs) or due to unforeseen challenges (e.g., a sample was lost in shipment and/or apart of a field was flooded)—the measurements may be imputed using models, subject to the requirements, as described in various embodiments herein.

Appendix A: Table 1 shows how samples were assigned to sample points. The parts in bold font were where imputation was needed to make predictions because a sample was not collected.

APPENDIX A: TABLE 1

How samples were randomly assigned to points. Changes in the way bulk density, pH, and texture samples were assigned to points are highlighted in bold font.

| Timeframe | Sample design | How samples are randomly assigned to points | | |
|---|---|---|---|---|
| | | SOC | Bulk density | pH/Texture |
| Oct. 1, 2019 to Mar. 16, 2020 | POISSWR (national point map) | All points | 1 in 5 points | Not collected |
| Mar. 16, 2020 to Aug. 31, 2020 | POISSWR (national point map) | All points | 1 in 3 points | Composite sample at bulk density points |
| Sep. 13, 2020 onward | Two-stage design | All points | 1 in 3 points | points |

This Appendix provides an example approach to imputation for these soil properties that are sampled less densely than soil organic carbon concentration is sampled.

To develop the imputation models for bulk density, pH, and texture, the criteria laid out in various embodiments as described herein were followed for handling missing samples. Among the developed imputation models that meet these criteria, the highest performing model for each soil property was selected as determined through the root mean squared error (RMSE) of cross-validation experiments using available soil measurements and other potential predictors of these properties.

For predicting bulk density, a regression kriging model that uses all available bulk density measurements was fit. For each texture property and for soil pH, linear regression models was trained using:

(a) point-level soil measurements taken outside of the Indigo™ Carbon program and (b) digital soil survey data.

These soil properties were imputed at every sample location with a soil organic carbon measurement but missing any of the other soil properties. Predictions of each soil property are made using a random draw from the model's predictive distribution at that sample location. By using a draw from the predictive distribution (rather than using the mean prediction at each point), the uncertainty about imputed values was reflected and that uncertainty was propagated through the biogeochemical model. Those draws from predictive distributions were also required in various examples and embodiments, and they enabled the introductions of variability into the predictions so that they matched that of measured properties.

The remainder of this Appendix A is structured as follows. In Appendix A: Section 2, an assessment of the imputation models for each of the soil properties, bulk density, soil pH, clay percent, and sand percent (silt percent is calculated as 100 less the clay percent less than sand percent) are presented in accordance with Section 3.5. In Appendix A: Section 3, the imputation of bulk density, beginning with the results of the imputation model in Appendix A: Section 3.1 followed by a summary of that imputation model in Appendix A: Section 3.1.1, is discussed.

Appendix A: 2. Assessment of Imputation Models

The various embodiments described herein allow bulk density, soil texture, and soil pH to be imputed wherever they are missing. A summary of the provided guidance for these imputation models is presented below:

Point-level imputations may be done with a single draw from a predictive distribution to maintain similar within-field variability as would be observed with no missing data. Predictive distributions may be constructed analytically, or with a resampling or simulation method, so long as the method has a theoretical basis.

External datasets may be used to train imputation models, including national soil surveys, remote sensing data, and soil samples collected outside of the sample project For each imputation model, report summaries of the imputed values may have to be provided. These report summaries may include:

Summaries of the number of missing measurements

Variability of imputed values

Associations between soil attributes

Performance of the imputation model

This guidance and criteria are discussed in the context of each imputation model below.

Appendix A: 3. Imputation of Bulk Density

In Appendix A: Section 3.1 the performance of the chosen imputation model for bulk density is described. The choice of this model among many alternatives is described later in Appendix A: Sections 3.2 and 3.3.

Appendix A: 3.1 Summary of the Performance of the Bulk Density Imputation Model

Appendix A: 3.1.1 Bulk Density Imputation Model

For bulk density imputation, a regression kriging model was used.

Regression step The first step of the model was a linear regression:

$$\text{bulk\_density} = 1.314 + 0.040 \times \text{soil\_carbon\_concentration} \quad (62)$$

The negative correlation between bulk density and the concentration of SOC, captured by the negative coefficient −0.040 in Equation (62), may be known in literature. The linear regression model (62) has a coefficient of determination $R2=0.225$.

APPENDIX A: TABLE 2

Summary of the kriging step of the bulk density imputation model. The final model had ID 492079575, which is a hash of the data used to fit the model and the hyperparameters. The model was fit on Nov. 17, 2021.

| | |
|---|---|
| maximum lag (meters) | 6,000 |
| number of lags (i.e., bins) | 60 |
| variogram model | spherical |
| range of the variogram (meters) | 2327.244 |
| sill $(g/cm^3)^2$ | 0.004 |
| nugget $(g/cm^3)^2$ | |

Kriging step The second step of the bulk density imputation model was kriging of the residuals of the linear regression model (62). The crux of this kriging step was the variogram, which captures the tendency for these residuals to be similar at nearby locations (i.e., the spatial autocorrelation). Appendix A: Table 2 shows the parameters of this kriging model. Collectively, the linear regression and kriging model have coefficient of determination $R2=0.809$. (Note that this model may explain 0.225 of the variance, draws from the predictive distribution in Appendix A: Section 3.1.2 ensured that uncertainty was not under-estimated.)

The variogram of the kriging model included a "maximum lag" parameter set to 6000 meters (see Appendix A: Table 2). For points with no bulk density measurement within 6000 meters, the kriging model used the sill as the estimate of the variance, and a warning was given by the *SciKit-GStat* (2021) Python package used in various models described herein for kriging. This situation occurred for 25 points, in fields that are small and far from other fields.

Appendix A: 3.1.2 Predictive Distribution

As described herein, draws from a predictive distribution may be and sometimes must be used to capture the uncertainty about imputed values. For each imputed bulk density sample point, the predictive distribution was centered at the mean bulk density prediction calculated from the fit regression kriging model, with standard deviation equal to the square root of the kriging error variance at that location. (For documentation of the kriging variance, see *SciKit-GStat* (2021), a Python package used in various models described herein for kriging.) In various models described herein, in the event a prediction was less than or equal to zero after a draw from the predictive distribution, that prediction was replaced by the minimum positive prediction in the dataset (see the row labeled "minimum" and column labeled "BD is imputed" in Appendix A: Table 6 in Appendix A: Section 3.1.5). This replacement occurred for 1 point.

Appendix A: Table 3 summarizes the predictive distribution. The average kriging error used for the predictions was 0.088 $g/cm^3$, or 7.0% of the mean bulk density prediction of 1.253 $g/cm^3$. Taking draws from this predictive distribution increased the overall variability of the predictions over mean predictions: overall standard deviation increased by 24% and average within-field standard deviation increased by 5%.

Appendix A: 3.1.2 Correlation with Other Soil Properties

For bulk density, the correlation between bulk density and soil carbon concentration were captured through the regression component of the regression kriging algorithm. As a result, the Spearman correlations (Appendix A: Table 4) are fairly similar, as required in various embodiments as described herein.

APPENDIX A: TABLE 3

Summary of the predictive distribution of the bulk density imputation. All units are $g/cm^3$.

| Quantity | Summary statistic | Value |
|---|---|---|
| mean prediction | average across points | 1.25 |
| | SD across points | 0.13 |
| | average of within-field SDs | 0.13 |
| SD of the predictive distribution | averaged across points | 0.09 |
| | SD across points | 0.00 |
| single draw from the predictive distribution | average across points | 1.25 |
| | SD across points | 0.15 |
| | average of within-field SDs | 0.15 |

Abbreviation: SD = standard deviation.

APPENDIX A: TABLE 4

The Spearman correlation between bulk density and soil organic carbon concentration is similar for points where bulk density is measured and for points where bulk density is imputed.

| | Spearman correlation of BD and % SOC |
|---|---|
| Points with measured bulk density | −0.456 |
| Points with imputed bulk density | −0.374 |

Appendix A: 3.1.4 Number of Points and Fields at which Bulk Density is Imputed For bulk density imputation, measurements were taken in the Indigo™ Carbon program. No measurements in other programs were used.

The number of such measurements is listed in Appendix A: Table 5. The number of fields with soil samples was larger than the number of fields on which credits were being issued, because some fields dropped out of the program after they were soil sampled. Those fields were still useful in the kriging model because they helped to better identify the statistical relationships between soil organic carbon concentration and bulk density (in the regression step of the imputation model) and in the spatial autocorrelation of the residuals of that linear regression (in the kriging step of the imputation model).

APPENDIX A: TABLE 5

Summary of the number of bulk density measurements that were imputed.

| | |
|---|---|
| Sample points with imputed bulk density | 33128 of 48851 (67.8%) |
| Fields with ≥1 imputed bulk density | 3955 of 4431 (89.3%) |

Appendix A: 3.1.5 Variability of Imputed and Measured Bulk Density Values

Appendix A: Table 6 summarizes the variability of the measured and imputed values of bulk density. Here, the imputed values were the (single) draws from the predictive distribution, the same values provided to the biogeochemical model. The distributions were similar in terms of their quartiles, average, and standard deviation. The typical variability within fields ("average of the within-field SDs") were also similar. This table shows that the imputations were accurately capturing the variability in the ground-truth measurements, as required in various embodiments as described herein.

APPENDIX A: TABLE 6

Summary of the variability of bulk density measurements and imputed values. All units are $g/cm^3$.

| Points where bulk density is . . . | imputed | measured |
|---|---|---|
| minimum | 0.08 | 0.20 |
| $25^{th}$ percentile | 1.16 | 1.17 |
| $50^{th}$ percentile | 1.26 | 1.25 |
| Average | 1.125 | 1.25 |
| $75^{th}$ percentile | 1.35 | 1.35 |
| maximum | 1.90 | 1.92 |
| SD | 0.15 | 0.15 |
| average of the within-field SDs | 0.09 | 0.09 |

Abbreviation: SD = standard deviation; BD = bulk density.

Appendix A: 3.1.6 Bias and Accuracy in Cross Validation

To assess the ability of the imputation model to predict accurately and precisely out-of-sample, k-fold cross validation was conducted with k=10 splits (as explained in Appendix A: Section 3.1.6). The accuracy and bias on held-out data is shown in Appendix A: Table 7. Importantly, the bias of the predictions was negligible.

APPENDIX A: TABLE 7

Summary of the performance of the bulk density imputation model on held-out data in cross validation. Shown is the average of the metric, plus or minus the standard deviation, across the k = 10 folds.

| | |
|---|---|
| RMSE | 0.095 ± 0.002 $g/cm^3$ |
| Bias | −0.000 ± 0.093 $g/cm^3$ |

Abbreviation: RMSE = root mean squared error.

Appendix A: 3.2 Methodology for Selecting a Model to Predict Bulk Density

Available soil measurements from Indigo™ Carbon within a cross validation framework were used to test a suite of bulk density prediction models. These models were evaluated for bias and performance before the final model was selected. For use in Indigo™ Carbon, this final model was trained on all available bulk density samples taken in Indigo™ Carbon and was used to make bulk density predictions at all sample locations without bulk density measurements. This practice—of doing (1) cross-validation for model selection and assessment and (2) fitting the model on all available training data (rather than a random sample of, say, 80% of the training data)—may be common outside of "Big Data" contexts. Because there were preciously few samples, all available measurements were used for training the model that served predictions in production. Because the cross-validation framework used almost as many training data points as this production model, the estimated precision and accuracy on held-out data (see Appendix A: Tables 9 and 7) gave reliable estimates of the out-of-sample performance of the production model. In this section the analysis datasets, cross validation framework, considered models, and considered predictors are provided. Results of this model selection process are presented in Appendix A: Section 3.3.

Appendix A: 3.2.1 Analysis Dataset

A subset of all soil sample locations for model selection were used. Appendix A: Table 8 provides a summary of this subset and our justification for each limitation

APPENDIX A: TABLE 8

Exclusion criteria for the cross-validation of the bulk density imputation model

| Exclusion criteria | Justification | Points |
|---|---|---|
| All points | N/A | 48851 |
| All points with a bulk density measurement | Model and cross validation can only be fit and evaluated with measured values | 15723 |
| All points in fields with ≥2 bulk density measurements | See Cross validation framework (Section 3.2.2) for explanation of the need for 2 + measurements per field | 14724 |

Appendix A: 3.2.2 Cross Validation Framework

Bulk density measurements within each field (and nearby fields) was used to predict at SOC sample points in the field. A cross validation framework was used to simulate and test this approach of predicting using nearby points.

Figure 13:
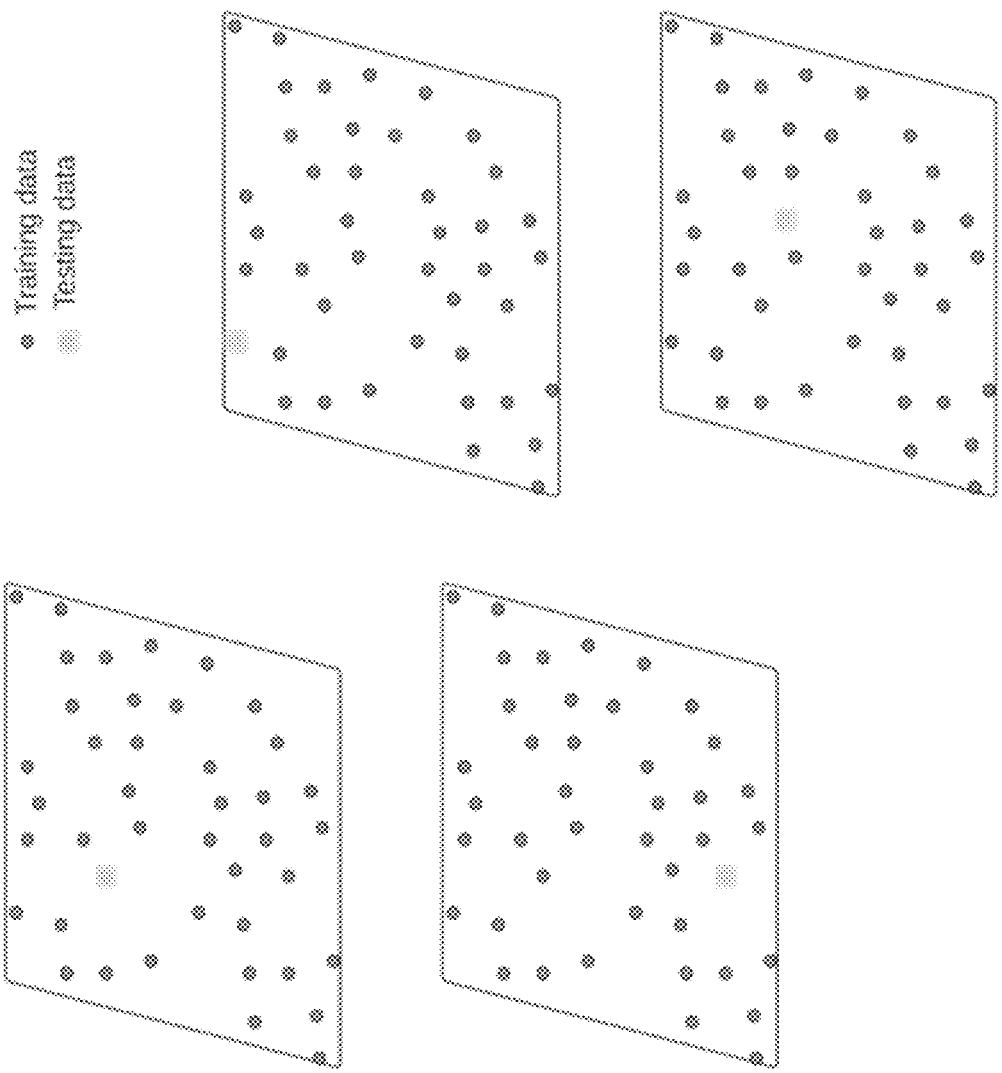
FIG. 13 illustrates a hold-out scheme for cross validation of the bulk density imputation model according to embodiments of the present disclosure.

For cross validation, a modification on shuffle-split cross validation was used in which one sample point from every field was withheld to use as the test dataset. All other points were used in the train dataset. This splitting method may be called GroupShuffleSplit. Such a splitting approach simulates a world in which at least one bulk density sample point in each field is included. This may be a property of the actual sampling scheme. FIG. 13 visually depicts this hold-out scheme. In FIG. 13, because imputation was performed in fields where bulk density measurements were taken elsewhere in the field, such prediction tasks were simulated by holding out one random point per field.

Two metrics were used to evaluate and compare the performance of the models considered for predicting bulk density. Appendix A: Table 9 describes the scoring in more detail.

Appendix A: 3.2.3 Models Considered

All models considered for predicting bulk density were compared to each other and to the baseline scenarios of using the simple global average of bulk density and using the simple field-level averages of bulk density. The models that were considered for interpolation ranged from distance-weighting approaches to linear regression analysis, machine learning algorithms, and kriging approaches. Many of these models also used hyperparameters, or configurations of the model whose values could not be estimated from data. These hyperparameters can further be used to optimize model performance. Appendix A: Table 10 summarizes the models that were considered as well as their hyperparameters.

APPENDIX A: TABLE 9

Scoring metrics

| Metric | Definition |
| --- | --- |
| Bias | The average of the errors. Used to determine systematic difference between toe prediction and the true value. |
| RMSE | Root Mean Squared Error (RMSE) is the square root of the average squared error. RMSE gives more weight to larger errors (compared to other common metrics like mean absolute error) |

APPENDIX A: TABLE 10

Models considered for the bulk density imputation.

| Model | Hyperparameters | About/why considered |
| --- | --- | --- |
| Global mean | | Simplest interpolation approach serving as baseline |
| Field-level mean | | Simple interpolation approach serving as baseline |
| gSSURGO | | values of bulk density from gSSURGO (2020) (a gridded version of SSURGO) at each sample location serving as baseline |
| K-nearest neighbors | Number of neighbors Weighting approach Power parameter for weighting | Intuitive and effcient approach using proximal measurements data |
| Linear regression | | Straightforward, easy to interpret global estimator with interpretable estimates of error |
| Decision Tree regression | Maximum tree depth Minimum samples at a leaf Maximum number of leaf nodes | Simple machine learning algorithm |
| AdaBoost | Estimator Loss function for updating weights Learning rate contribution of each estimator | Complex meta-estimator of a machine learning algorithm that fits multiple copies of the same estimator, tuning in each repitition |
| Ordinary kriging | Variogram model Kriging specifications | Common geospatial technique that imputes values using a stastical model that describes covariability over space |
| Regression kriging | Ordinary kriging hyperparameters Regression model used prior to kriging of errors | This procedure was suggested by Ahmed and De Marsily (1987) and Odeh, McBratney, and Chittleborough (1995) where the drift and residuals can be estimated separately and then summed |

Appendix A: 3.2.4 Predictors Considered

In the evaluation of models to predict bulk density, several categories of predictors were considered. New predictors may be considered in future iterations of the bulk density predictions. Appendix A: Table 11 below describes these considered predictors.

APPENDIX A: TABLE 11

Predictors considered for the bulk density imputation model

| Predictor category | Predictor | About/why considered |
| --- | --- | --- |
| Location | Latitude and longitude | Used for geographic trends and models that use proximal points for predictions |
| | Location x and y coordinates in Albers projection | Same reasons as above, but locations are transformed to an equal-area projection (in meters) |

APPENDIX A: TABLE 11-continued

Predictors considered for the bulk density imputation model

| Predictor category | Predictor | About/why considered |
| --- | --- | --- |
| Soil measurements | Soil organic carbon | Measured SOC at each point, correlated with bulk density and available at every bulk density measured and non-measured location |
| gSSURGO | Bulk density Soil organic mattter | Bulk density from gSSURGO survey SOM from gSSURGO survey |

APPENDIX A: TABLE 11-continued

Predictors considered for the bulk density imputation model

| Predictor category | Predictor | About/why considered |
| --- | --- | --- |
| | Texture | Sand, Clay, and Silt percentages from gSSURGO survey |
| | Soil pH | Soil pH from gSSURGO |

Appendix A: 3.3 Results of Model Selection for Predicting Bulk Density

Appendix A: 3.3.1 Selected Approach

In various embodiments, regression kriging led to the best estimations of bulk density. In cross validation experiments, regression kriging with a simple linear regression of bulk density on soil carbon concentration produced the lowest root mean squared error of predicted values. Appendix A: Table 12 summarizes the performance of the considered models.

While including gSSURGO predictors improved predictions in linear regression and machine learning algorithms, this same improvement was not observed with regression kriging and selected a regression kriging approach whose regression was only a linear regression on measured SOC.

APPENDIX A: TABLE 12

Results of cross validation experiments for predicting bulk density. The chosen model, highlighted below, achieves the lowest RMSE. Abbreviations: RMSE = root mean squared error; SOC = soil organic carbon concentration. Units of the bias and RMSE columns are both g/cm$^3$. The approaches marked with * above used nested cross-validation: the model itself does its own cross-validation on the training set to choose optimal hyperparameters. Thus, the optimal hyperparameters vary from one fold to another (of the outer k-fold cross validation).

| Interpolation approach | Bias | RMSE |
|---|---|---|
| AdaBoost (SOC, location, & gSSURGO soil properties)* | −0.0005 | 0.0885 |
| AdaBoost (SOC, location)* | 0.0004 | 0.0908 |
| K-Nearest Neighbors* | −0.001 | 0.0921 |
| Decision Tree Regressor (SOC, location)* | 0.0021 | 0.0983 |
| Decision Tree Regressor (SOC, location, & gSSURGO soil properties)* | 0.0026 | 0.099 |
| Field-level mean | −0.0003 | 0.1025 |
| Linear regression (SOC, location, & gSSURGO soil properties)* | 0.0043 | 0.106 |
| Linear regression (SOC, location) | 0.0048 | 0.1164 |
| Linear regression (SOC) | −0.0059 | 0.1183 |
| Global average | −0.0082 | 0.1416 |
| Regression kriging (SOC)* | 0.0008 | 0.0857 |
| Regression kriging (SOC, location, all gSSURGO soil variables)* | 0.0003 | 0.0873 |
| Ordinary kriging* | −0.0004 | 0.0919 |
| gSSURGO | 0.121 | 0.178 |

Appendix A: 3.3.2 Validating Assumptions of Our Variogram

In various embodiments, the experimental variogram used in regression kriging should be computed and used out to a spatial distance that is logical for the spatial property being interpolated. This is, for example, described at p. 37 of "Basic Steps in Geostatistics: The Variogram and Kriging" by Oliver and Webster, published in 2015. A maximum lag over which to fit the variogram was selected so that the fitted model was accurate over the distance kriged. In some examples, distances between 2000-7000 meters, which is approximately the diameter of 4 to 14 adjacent 80-acre fields, were tested. The lag determined in the variogram computing step is described in Appendix A: Table 2 above. What occurred over distances larger than 2000-7000 meters across the maximum lag was of little consequence for the predictions (i.e., a point 12 80-acre fields away should have little correlation with the point to be predicted).

When the variogram for the regression kriging model, above, was constructed many of the major variogram assumptions were considered:
1. No skewness was found in the data, so no transformation was needed to ensure normality and adjust for outliers.
2. No major trends were observed in the data across space, nor were differences between the x (longitude) direction and y (latitude) direction observed, therefore no adjustment for anisotropy was made and the assumption about weak stationarity held.

When a point to be interpolated was further than the maximum lag from any other bulk density measurement, the algorithm presented herein used the average error of the upstream linear model instead of the kriging estimate of the nearby errors that would otherwise be used in regression kriging.

Such a scenario, as described above, may occur on fields where there are no bulk density measurements (and no bulk density measurements in nearby fields). The number of such cases was 25, as mentioned in Appendix A: Section 3.1 above. The kriging error at these sample locations was undefined. As a conservative estimate, the predictive distribution in these scenarios was set to the sum of the nugget and the sill of the variogram used in the kriging step. This sum reflected the co-variability of points beyond the distance at which the points were expected to be spatially dependent. This is, for example, described at p. 31 of "Basic Steps in Geostatistics: The Variogram and Kriging" by Oliver and Webster, published in 2015.

Appendix A: 4. Imputation of Soil pH and Texture

Appendix A: 4.1 Assessment of Soil pH Imputation Model

For pH imputation, a linear regression model was used. This is described in greater detail below. This linear regression model was trained on an external dataset of point-level soil pH measurements, synthetically constructed field-level composite soil pH measurements, and point-level gSSURGO values.

Appendix A: 4.1.1. Imputation Model

For soil pH, a linear regression model was used with two predictors:
1. the soil pH according to gSSURGO (denoted soil_pH_SSURGO) and
2. the composite measurement of soil pH taken by Indigo™ (denoted soil_pH_composite_sample).

The fitted regression model was:

$$pH = 0.185 + 0.801 \times soil\_pH\_composite\_sample + 0.197 \times soil\_pH\_SSURGO \quad (63)$$

In Equation (63), more weight was assigned to the ground-truth measurement in the field than to the prediction from SSURGO, indicating that even a single composite sample of pH that represents the field adds a lot of predictive value over using SSURGO alone. The coefficient of determination of the model (63) is R2=0.403. The model had ID 509161250 (this is a hash of the data used to fit the model and of the hyperparameters), and it was fit on Nov. 17, 2021.

Appendix A: 4.1.2 Predictive Distribution

For each imputed sample point, the predictive distribution was normally distributed with mean equal to the soil pH prediction from the linear regression model and with standard deviation equal to the square root of the calculated prediction variance for the predicted point.

Appendix A: Table 13 summarizes the predictive distribution. The standard deviation of the predictive distribution is typically 0.62. To put that uncertainty of each imputation in perspective, that is 9% of the average imputed value of pH, 6.85.

APPENDIX A: TABLE 13

Summary of the predictive distribution of the soil pH imputation.

| Quantity | Summary statistic | Value |
|---|---|---|
| Mean prediction | average across points | 6.88 |
| | SD across points | 0.71 |
| | average of within-field SDs | 0.06 |
| SD of the predictive distribution | averaged across points | 0.62 |
| | SD across points | 0.00 |
| Single draw from the predictive distribution | average across points | 6.85 |
| | SD across points | 0.82 |
| | average of within-field SDs | 0.56 |

Abbreviation: SD = standard deviation.

In rare cases, this normal distribution produced pH values that were outside the typical range found in cropland, due to the tails on normal distributions. The USDA NRCS reported in "Soil Quality Indicators: pH" published in 1998 that soil pH below 5.6 is considered low for most crops, and pH above 8.0 is considered high for most crops. In the training dataset (discussed in Appendix A: Section 4.1.4. below), 14% of pH measurements are below 5.6, and 2.6% of pH measurements are greater than 8.

Thus, in some examples described herein, to make a range of agronomically plausible pH values, the range [5, 8.5] was chosen for North American cropland; in the training dataset, these values are the 1.7% percentile and 99.6% percentile. To avoid providing implausible values of pH to the biogeochemical model, the imputations fell within this agronomically plausible range by conditioning the predictive distribution on falling in the range [5, 8.5] (i.e., draws from the predictive distribution that fell outside that range were rejected).

Appendix A: 4.1.3 Correlation with Other Imputed Soil Properties

For soil pH imputation, the pH was predicted using the composite measurement of pH and gSSRUGO's prediction of pH at the point. In this case, the model did not explicitly capture correlation with other soil properties.

Appendix A: 4.1.4 Datasets Used

For soil pH imputation, the model was trained with a static dataset of point-level soil pH measurements. This dataset was collected by Indigo™ in 2018 for business purposes outside of Indigo™ Carbon, and the dataset was referred to as Indigo Research Partners. A 1-acre grid sampling of soil pH was conducted in commercial fields undergoing field trials. See Appendix A: Section 4.3 for an overview of the overlap in state coverage and soil property values between Indigo™ Research Partners and Indigo™ Carbon.

With the point-level soil pH measurements from Indigo™ Research Partners, field-level composite measurements were constructed from a random subsample of measurements in each field. This composite measurement was used as a predictor variable; it served as a proxy for the composite samples in Indigo™ Carbon.

In addition to the point and field-level soil pH measurements, point-level gSSURGO estimates for soil pH were used. These estimates were the weighted average gSSURGO major component values down to 30 centimeter depths. gSSURGO values were imputed from layers above or below layers with missing gSSURGO values.

gSSURGO values were missing for a relatively small number of points in both the training dataset in Indigo™ Research Partners and in the prediction dataset in the Indigo™ project (Appendix A: Table 14). These points were dropped from the analysis: points in Indigo™ Research Partners that were missing gSSURGO were not used to fit the imputation models, and points in the project that were missing gSSURGO were not sent to the biogeochemical model (but were captured in downstream analyses of bias in various embodiments described herein). An example situation that lead to gSSURGO values being missing was when the map unit is a "borrow pit": the land may have been scraped away many years ago (e.g., to build a highway overpass), and it was recently replanted. Soil databases like gSSURGO cannot reliably predict the soil profiles in land with such disruptions.

APPENDIX A: TABLE 14

The number of points in the training dataset and prediction dataset where gSSURGO was missing.

| | |
|---|---|
| IRP (training dataset) | 20 of 49592 (0.04%) |
| Indigo Carbon (prediction dataset) | 124 of 53484 (0.2%) |

If an Indigo™ Carbon field does not have a recorded pH or texture composite sample, then the composite measurement value that we would have obtained had we pulled a composite sample from the field by averaging gSSURGO values at all locations where SOC concentration was measured on the field was guessed.

Appendix A: 4.1.5 Number of Points and Fields at which Soil pH is Imputed

Appendix A: Table 15 lists the number of fields in which imputations of soil pH were made. Note that this number of fields was larger than the number of fields in the issuance because more fields were soil sampled than ended up in the issuance (due to attrition), as mentioned in Appendix A: Section 3.1.4. Because those sampled fields were still useful for the kriging step in the bulk density model in Appendix A: Section 3, pH in those fields was imputed, as well, even though this model did not improve as the size of the Indigo™ Carbon program grew. Instead, the pH imputation model improved with the size of its training dataset, which is Indigo™ Research Partners and gSSURGO predictions on those fields (as described in Appendix A: Section 4.1.4).

APPENDIX A: TABLE 15

Summary of the number of soil pH measurements that were imputed.

| | |
|---|---|
| Fields | 4732 |
| Carbon points per field (mean ± SD) | 11.3 ± 8.7 |
| Fields with composite samples | 4120 (87.1%) |

Abbreviation: SD = standard deviation.

Appendix A: 4.1.6 Variability of Imputed and Measured Soil pH Values

Appendix A: Table 16 summarizes the variability of the measured and imputed values of soil pH in the training dataset (Indigo™ Research Partners) and in the imputations made in Indigo™ Carbon.

As required by various embodiments as described herein, the imputed values were the (single) draws from the predictive distribution, so that uncertainty about imputed values is propagated to the biogeochemical model. The distributions were fairly similar. (They were not as similar as they were for bulk density (Appendix A: Table 6) because here the model generalized from one dataset (Indigo™ Research Partners) to another (Indigo™ Carbon) and had only composite-level measurements, whereas the bulk density model could exploit measurements at individual points in Indigo™ Carbon.) Importantly, the typical variability within fields ("average of the within-field SDs") were similar, and the imputed values were typically more variable within fields, indicating that uncertainty is being estimated conservatively.

APPENDIX A: TABLE 16

Summary of the variability of soil pH measurements and imputed values.

| Soil pH measured in ... | Indigo Carbon | Indigo Partners |
|---|---|---|
| minimum | 5.000 | 1.000 |
| $25^{th}$ percentile | 6.233 | 5.800 |
| $50^{th}$ percentile | 6.840 | 6.400 |
| average | 6.845 | 6.410 |
| $75^{th}$ percentile | 7.470 | 6.900 |
| maximum | 8.500 | 13.000 |
| SD | 0.822 | 0.796 |
| average of the within-field SDs | 0.562 | 0.540 |

Abbreviation: SD = standard deviation.

Appendix A: 4.1.7 Bias and Accuracy in Cross Validation

To assess the ability of the imputation model to generalize outside the Indigo™ Research Partners training dataset accurately and precisely, a k-fold cross validation with k=10 splits was conducted (as explained in Appendix A: Section 4.3.2). The accuracy and bias on held-out data is shown in Appendix A: Table 17. The bias of the predictions is negligible.

APPENDIX A: TABLE 17

Summary of the performance of the soil pH imputation model on held-out data in cross validation. Shown is the average of the metric, plus or minus the standard deviation, across the k = 10 folds.

| RMSE | $0.613 \pm 0.002$ |
|---|---|
| Bias | $-0.000 \pm 0.005$ |

Abbreviation: RMSE = root mean squared error.

Appendix A: 4.2 Assessment of Soil Texture Imputation Model

Appendix A: 4.2.1 Imputation Model

For imputation of soil texture, two separate linear regressions were fit with logit-transformed outcomes, one for sand percent and one for clay percent, described in more detail in Appendix A: Section 3. Imputed silt values were estimated as 100% less the sum of sand and clay percentages. Clay and sand were modeled, and silt was set to 100% minus their sum, because clay and sand were the most important agronomically.

Because sand and clay values were imputed with separate regressions, their sum occasionally added to more than 100%. In those cases, each property was scaled relatively so that their sum adds to 100%, leaving silt in these fields at zero.

The sand and clay models were trained on an external dataset of point-level sand and clay measurements, synthetically constructed field-level composite sand and clay measurements, and point-level gSSURGO values for sand and clay.

The fitted linear regressions was:

$$\text{logit(clay)} = -2.923 + 0.017 \times \text{clay ssurgo} + 0.080 \times \text{clay composite} \quad (64a)$$

$$\text{logit(sand)} = -2.278 + 0.009 \times \text{sand ssurgo} + 0.040 \times \text{sand composite} \quad (64b)$$

Both models (64a) and (64b) put more "weight" on the composite sample taken in the field (0.80 and 0.40, respectively) than on the SSURGO prediction of texture at that point in the field. This greater weight confirmed the value of taking ground-truth samples, even just one composite sample per field, rather than relying only on SSURGO. In Equation (64), the target variables—clay and sand content—were transformed with the logit function $$logit(x) \equiv \log\left(\frac{x}{1-x}\right),$$

which is commonly applied to outcome variables that are constrained to be between zero and one (so that the predictions on the right-hand side can be any real number).

Appendix A: Table 18 shows that the coefficient of determination (R2) value is large, so a lot of the variance was explained by this model. Because the same dataset was used to train both the clay and sand models, the model ID is identical.

APPENDIX A: TABLE 18

Summary of the soil pH imputation model.

| Outcome variable: | clay | sand |
|---|---|---|
| $R^2$ | 0.557 | 0.796 |
| Model ID (hash) | 1166685592 | 1166685592 |
| Fitted on | Nov. 17, 2021 | Nov. 17, 2021 |

Appendix A: 4.2.2 Predictive Distribution

For each imputed sand and clay value, the predictive distribution was normally distributed that was centered at the mean sand (or clay) prediction of the linear regression model, with standard deviation equal to the square root of the calculated prediction variance for the predicted point. Appendix A: Table 19 summarizes that predictive distribution. The standard deviation of the predictive distribution was rather large compared to the typical values, indicating that the texture imputation model has considerable uncertainty. As for the other imputation models, this uncertainty was propagated to the biogeochemical model because a draw from the predictive distribution was used.

APPENDIX A: TABLE 19

Summary of the predictive distribution of the soil texture imputation.

| Quantity | Summary statistic | Outcome variable clay | sand |
|---|---|---|---|
| mean prediction | average across points | 23.6% | 32.4% |
| SD of the predictive distribution | SD across points | 11.8% | 19.7% |
| | average of within-field SDs | 1.4% | 1.7% |
| | averaged across points | 67.7% | 61.8% |
| single draw from the predictive distribution | SD across points | 0.0% | 0.0% |
| | average across points | 25.9% | 32.6% |
| | SD across points | 14.0% | 20.2% |
| | average of within-field SDs | 11.0% | 8.4% |

Abbreviation: SD = standard deviation.

Like for imputations of pH (see Appendix A: Section 4.1.2), "extreme" values of texture drawn from the predictive distribution were rejected, and draws from the predictive distribution were repeated until a non-extreme value was drawn. These imputations of texture were used in Saxton's equations to compute inputs to the biogeochemical model (see the various embodiments described herein). Therefore, the same constraints used by Saxton et al. (1986) were imposed on imputations of texture as described herein: that 5%<clay<60% and that sand >5%. These ranges covered most of the training dataset (described in Appendix A: Section 4.1.4): 5.2% of clay measurements were less than 5%; 3.4% of clay measurements were greater than 60%; and 0.1% of sand values were less than 5%.

Appendix A: 4.2.3 Correlation with Other Soil Properties

The texture imputation model did not explicitly capture correlations with soil properties other than texture, because the only predictors in Equation (64) are texture variables. Correlations among sand, silt, and clay may partially or fully be captured by the constraint that sand, silt, and clay add to 100%.

Appendix A: 4.2.4 Datasets Used

For sand and clay imputations, various models described herein were trained with a static dataset of point-level sand and clay measurements using the same dataset used for pH (from Indigo™ Research Partners); Appendix A: Section 4.1.4 may be referenced for a summary of that dataset. Because of the high costs of measuring texture in the lab (compared to pH), the Indigo™ Research Partners dataset has one texture measurement for every ten acres (i.e., one of out ten points in a one-acre grid sample design).

Appendix A: 4.2.5 Number of Points and Fields at which Soil Texture is Imputed Because soil texture and pH are measured on the same composite samples, the number of points and fields at which texture was imputed (Appendix A: Table 20) was identical to that for pH (Appendix A: Table 15).

APPENDIX A: TABLE 20

Summary of the number of soil texture measurements that were imputed.

| Fields | 4732 |
|---|---|
| Carbon points per field (mean ± SD) | 11.3 ± 9.7 |
| Fields with composite samples | 4120 (87.1%) |

Abbreviation: SD = standard deviation.

Appendix A: 4.2.6 Variability of Imputed and Measured Soil Texture Values

Appendix A: Table 21 shows the variability among imputed values in Indigo™ Carbon (left-hand columns) and among the training dataset in Indigo™ Research Partners (right-hand columns). The inter-quartile range and within-field variability were similar. The imputation model's minima and maxima values were less extreme than the measured values, indicating that the model is skeptical of such extreme values.

APPENDIX A: TABLE 21

Summary of the variability of bulk density measurements and imputed values. All units are g/cm$^3$.

| Texture measured in . . . Outcome variable | Indigo day | Carbon sand | Indigo clay | Partners sand |
|---|---|---|---|---|
| minimum | 5.0% | 5.0% | 0.0% | 2.0% |
| 25$^{th}$ percentile | 14.2% | 17.0% | 19.0% | 22.0% |
| 50$^{th}$ percentile | 23.5% | 26.3% | 26.0% | 31.0% |
| average | 25.9% | 32.6% | 26.8% | 37.2% |
| 75$^{th}$ percentile | 35.9% | 41.1% | 33.0% | 49.0% |
| maximum | 60.0% | 91.1% | 90.0% | 97.0% |
| SD | 14.0% | 20.2% | 14.2% | 21.0% |
| average of the within-held SDs | 11.0% | 8.4% | 6.7% | 9.3% |

Abbreviation: SD = standard deviation.

Appendix A: 4.2.7 Bias and Accuracy in Cross Validation

APPENDIX A: TABLE 22

Summary of the performance of the soil texture imputation model on held-out data in cross validation. Shown is the average of the metric, plus or minus the standard deviation, across the k = 10 folds.

| Outcome variable: | clay | sand |
|---|---|---|
| RMSE | 9.64% ± 0.30% | 9.59% ± 0.14 |
| Bias | −1.67% ± 0.20% | −0.54% ± 0.16% |

Abbreviation: RMSE = root mean squared error.

Appendix A: 4.3 Methodology for Predicting Soil pH and Texture

Soil measurements from a separate Indigo™ business line, Indigo™ Research Partners, were used within a cross validation framework to test a suite of texture and soil pH prediction models. These models were evaluated for bias and performance before a final model for each soil property is selected. For use in Indigo™ Carbon, these final models were trained on all available data from Indigo™ Research Partners and used to make texture and pH predictions at all sample locations in Indigo™ Carbon. In this section the analysis datasets, cross validation framework, considered models, and considered predictors are discussed. Results of this work are presented in the subsequent section.

Appendix A: 4.3.1 Analysis Dataset

For model selection, soil measurements from Indigo™ Research Partners were used. This dataset provided point-level measurements for model fitting and testing. Indigo™ Carbon was not used for model fitting because only composite, field-level measurements were taken.

The Indigo™ Research Partners data was subsetted for pH and for texture separately. For each soil property, all data points were subsetted where the associated soil property was measured. Fields with a minimum number of soil samples per field were further subsetted. This minimum was set in order to generate a synthetic composite measurement in each field at roughly the same sampling density in which actual composites were measured in Indigo™ Carbon. Count of points used for model selection and model fitting are outlined in Appendix A: Table 23.

APPENDIX A: TABLE 23

Filters applied to the Indigo ™ Research Partners datasets for the pH model and for the texture model.

| pH | Original data | 67475 | 100.00% |
|---|---|---|---|
| | Limit to points with pH samples | 47788 | 70.82% |
| | Limit to fields with > 20 pH samples | 46310 | 96.91% |
| Texture | Original data | 67475 | 100.00% |
| | Limit to texture samples | 6157 | 9.12% |
| | Limit to fields with > 3 texture samples | 6094 | 98.98% |

Figure 14A:
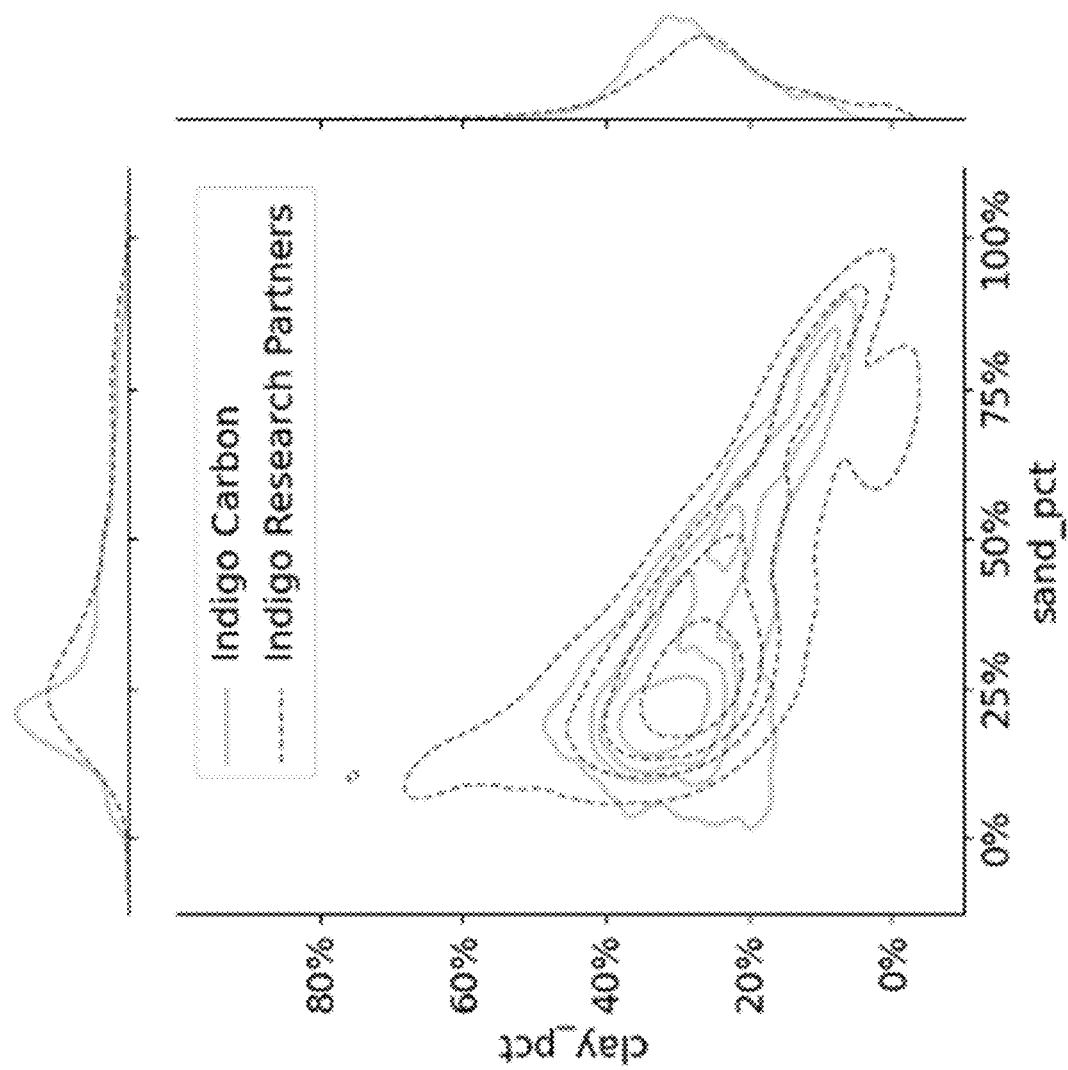
FIG. 14A illustrates a contour line chart summarizing the state of overlap between two soil sample datasets and the values of those datasets in terms of clay versus sand content according to embodiments of the present disclosure.
Figure 14B:
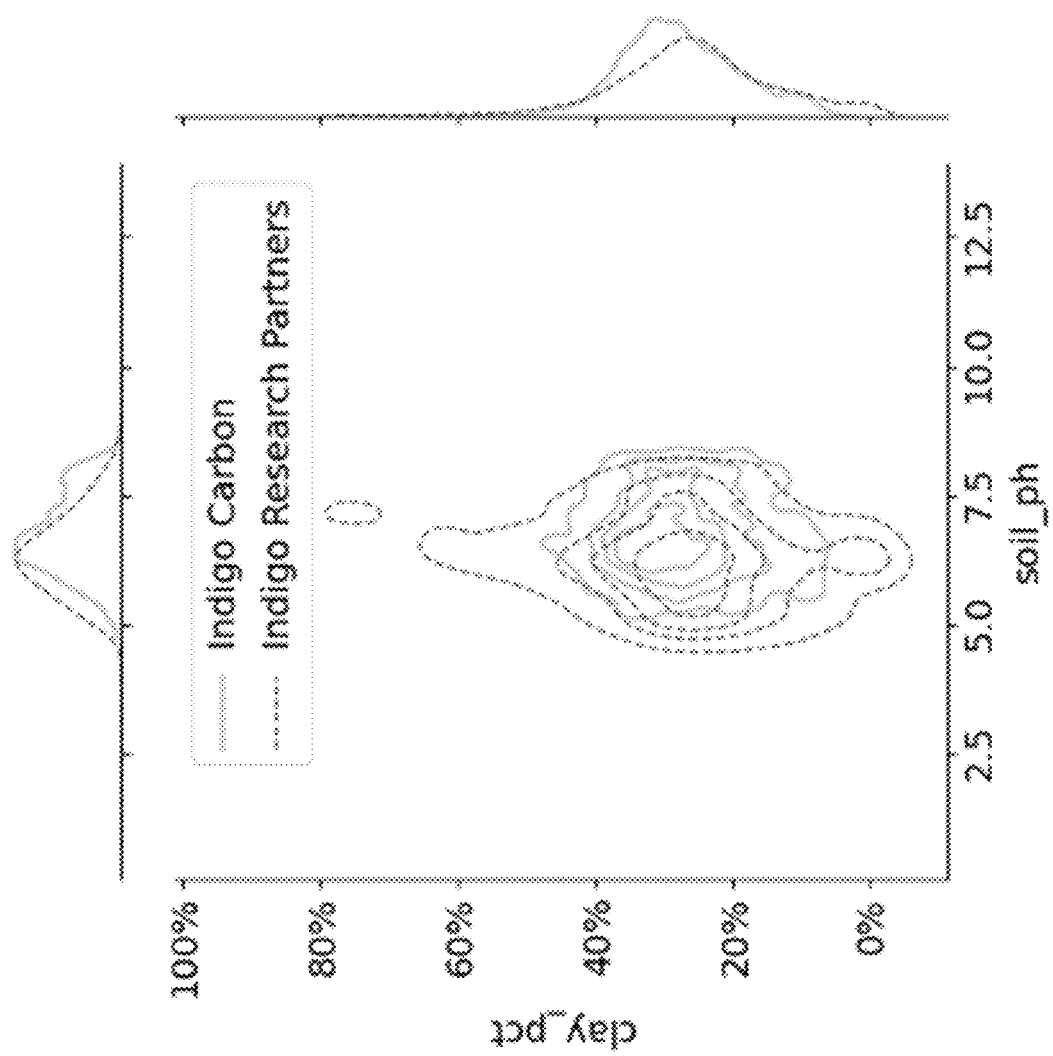
FIG. 14B illustrates a contour line chart summarizing the state of overlap between two soil sample datasets and the values of those datasets in terms of clay content versus pH according to embodiments of the present disclosure.
Figure 14C:
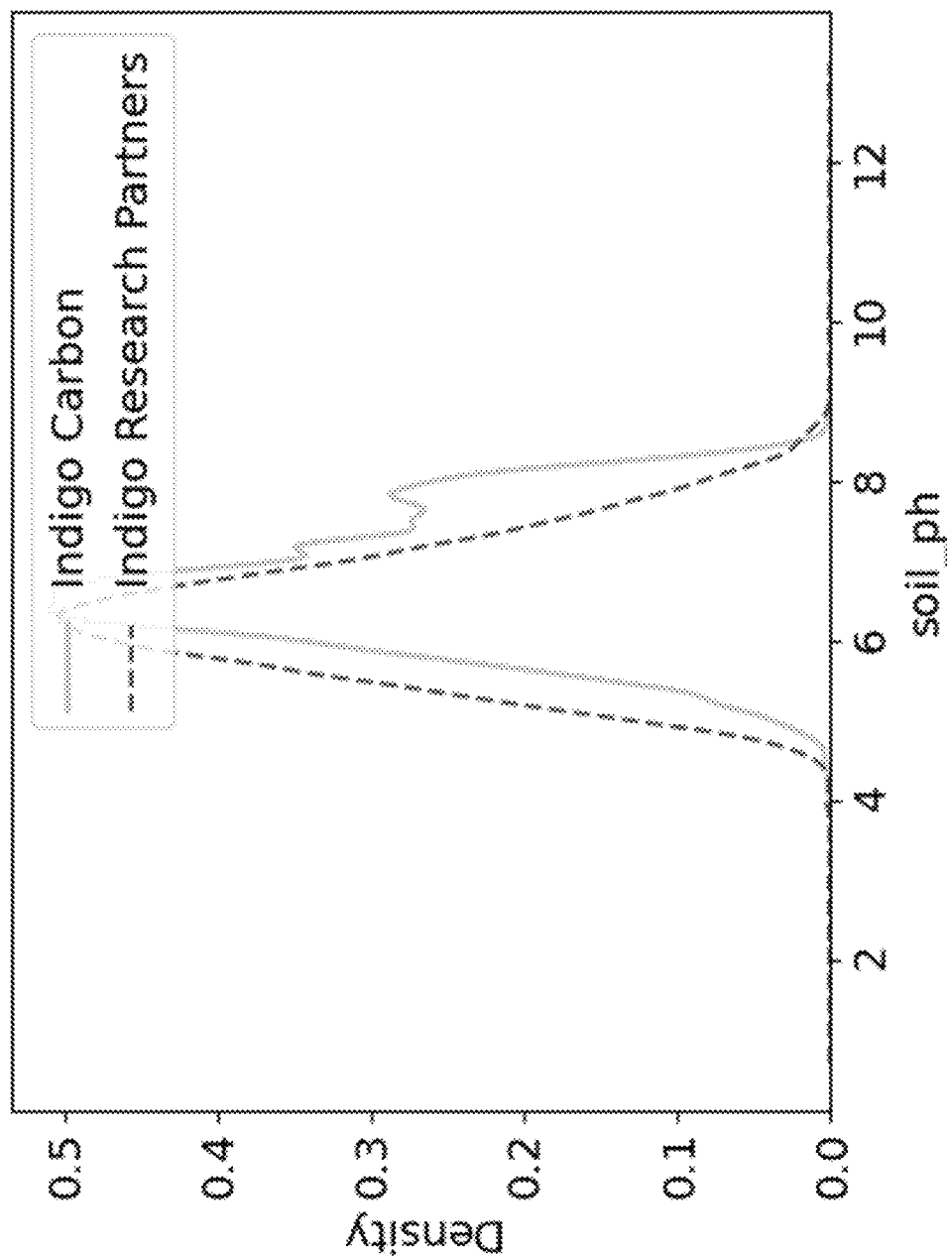
FIG. 14C illustrates a histogram chart, smoothed using a kernel density estimate, summarizing the state of overlap between two soil sample datasets and the values of those datasets in terms of pH according to embodiments of the present disclosure.
Figure 15:
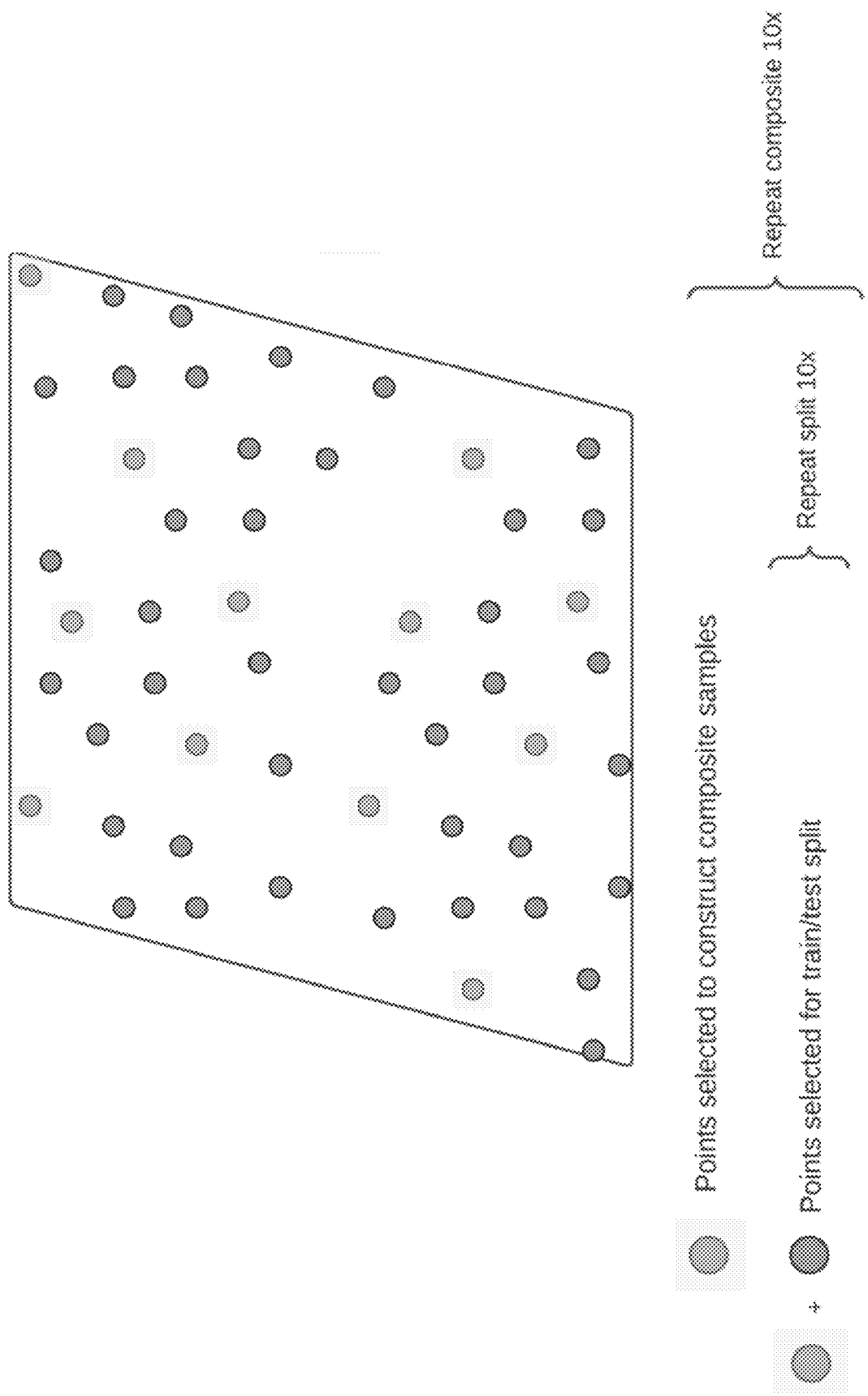
FIG. 15 illustrates a visual overview of the nested cross-validation used for pH and texture and related selection schema according to embodiments of the present disclosure.

An incomplete overlap was present in geographic coverage and in soil property values between the Indigo™ Carbon dataset on which soil properties were predicted and the Indigo™ Research Partners dataset with which the model was fit. FIG. 14A, FIG. 14B, and FIG. 14C summarize the state overlap between these two soil sample datasets and also the values of those datasets.

Appendix A: 4.3.2 Cross Validation Framework

Cross-validation experiments were used to select the model (among a menu of options described in Appendix A: Section 4.3.3) and to evaluate how well it predicted out of sample. For the cross validation experiments sample-level measurements of pH and soil texture collected in the 2018 Indigo™ Research Partners sampling campaign were used Such measurements of pH and soil texture were used to simulate taking composite measurements and validating the predictions at sample points. Our cross validation approach was structured in two steps. Each step was repeated 10 times:

Step 1: Cross validation for constructing a synthetic composite sample First, a fixed fraction of sample points were randomly selected from each field, p, from which to construct a synthetic composite sample. This composite sample was used as a predictor to train and test regressions.

The objective was to select p that approximates the density of sample points taken in Indigo™ Carbon for composite pH and texture measurements: between 1 sample/ 24 acres and 1 sample/40 acres (or one sample per every 3-5 carbon samples, where each carbon sample was taken every 8 acres).

The sampling rates in Indigo™ Research Partners were used to determine p for both Texture and pH. Appendix A: Table 24 highlights the selection of p.

APPENDIX A: TABLE 24

Fraction p of samples in Indigo Research Partners that were selected randomly to approximate the sample density in Indigo Carbon for purposes of cross-validation experiments.

| Soil property | IRP median sampling rate | p used in cross validation |
|---|---|---|
| pH | 1 sample per acre | =1/24 ≈ 5% |
| Texture | 1 sample per 10 acres | =10/24 ≈ 40% |

Step 2: Train/test splits Next, each field was split into train and test datasets, whereby a fraction, q, was selected to be in the training dataset. q was selected to be set to 50%. FIG. 3 provides a visual overview of this selection schema.

Appendix A: 4.3.3 Considered Models

All models considered were compared to each other for predicting pH and texture and these models were compared to the baseline scenarios of
1. using the composite sample for the field at each point, and
2. using the gSSURGO estimate at each point.

The models that were considered herein ranged from scaling gSSURGO, to linear regression models, logistic models, and simple machine learning algorithms. Appendix A: Table 25 summarizes the models that were considered.

Appendix A: 4.3.4 Considered Predictors

In the evaluation of models to predict pH and texture, several categories of predictors were considered. New predictors may also be considered in future iterations of the bulk density predictions. Appendix A: Table 26 describes these considered predictors.

Appendix A: Computing Average pH pH was calculated as the negative log of the concentration of hydronium ions (in moles per liter):

$$pH = -\log(h) \text{ where } h = H3O+\text{concentration}. \quad (65)$$

Therefore, the composite samples did not represent the average pH value at the sample locations. Instead, when n samples of equal volume were combined into a composite and then homogenized, the concentrations of hydronium ions in the samples were averaged, and the pH measurement was the negative log of that average concentration. Thus, the following transformation was used to simulate the pH measurement on a composite sample:

$$\overline{pH} = -\log(\overline{h}) = -\left(\frac{1}{n}\sum_{i=1}^{n} 10^{-pH_i}\right) \quad (66)$$

where the sum runs across samples i that enter into the (simulated) composite.

Appendix A: 4.4 Results of Model Selection for Soil pH and Texture

Appendix A: 4.4.1 Selected Approaches

For pH, a linear regression model on composite pH samples and point-level pH gSSURGO values led to a simple high-performing prediction of point-level pH. In the cross validation experiments, this approach produced the lowest root mean squared error of predicted values.

APPENDIX A: TABLE 25

| Models considered for imputation of soil pH and texture | |
|---|---|
| Model | About/why considered |
| Composite sample for whole field | Simplest interpolation approach serving as baseline |
| gSSURGO estimate at each sample point | Simple interpolation approach serving as baseline |
| Scale SSURGO by ratio of composite sample to composite gSSURGO | Simple approach relying on available gSSURGO values at each point |
| Linear regression of gSSURGO points sample points | Straight-forward, easy to interpret relationship between gSSURGO and measured values. Does not rely on composite measurements |
| Linear regression of composite sample and point-level attributes | Straight-foward global estimator with composite values and point-level attributes |
| Logit-transformed linear regression of composite sample and point-level attributes | Transformed global estimator to account for the bounded nature of texture and pH values |
| Decision Tree regression of composite sample and point-level attributes | Simple machine learning algorithm for predicting soil properties |

APPENDIX A: TABLE 26

Predictors considered for imputation of soil pH and texture.
Abbreviations: % SOC = soil organic carbon concentration; BD = bulk density;
IRP = Indigo ™ Research Partners

| Preditor category | Predictor | About/why considered |
|---|---|---|
| Location | Latitude and longitude | Used for geographic trends and models that use proximal points for predictions |
| | x and y coordinates in the Albers projections | Same reasons as for latitude and longitude, but locations are transformed to an equal-area projection (in meters) |
| Soil measurements | Soil organic carbon | Measured % SOC at each IRP point |
| | Bulk density | Measured BD at each IRP point |
| gSSURGO | Bulk density | Predictions are available across both Indigo Research Partners and Indigo Carbon |
| | Soil organic matter | |
| | Texture | |
| | Soil pH | |
| Lidar 10m resolution from the National Elevation Dataset (NED) | Aspect | Topography is an important property of soil that may be predictive of soil pH and texture |
| | Elevation | |
| | Slope | |
| | Topographic Position Index (TPI) | |
| | Terrain Ruggedness Idex (TRI) | |
| Pedotransfer functions (PTFs) | Pachepsky, Rawis, and Lin (2006) | PFTs are used to predict certain soil properties from soil surveys |
| | Abdelbaki (2018) | |
| | Román Dobarco et. al. (2019) | |

For texture, which was predicted with separate models for sand and clay, a logit-transformed linear regression model on composite sand or clay samples (respectively) and point-level sand or clay gSSURGO values (respectively) led to the highest performing prediction of point-level texture values.

While a different model was identified for each soil property to achieve the lowest RMSE, similar models with similar predictor values were used for pH and texture. The linear regression and logit-transformed linear regression models with point-level gSSURGO and composite measurement predictors were easy to explain and all achieved low RMSEs relative to the broader field of considered models. Furthermore, these linear regressions had clear theoretical foundations for constructing predictive distributions. Appendix A: Table 27 summarizes the performance of the considered models

APPENDIX A: TABLE 27

Results of cross validation experiments for predicting soil pH and texture. Performance of the selected models is highlighted.

| | pH | | Sand | | clay | |
|---|---|---|---|---|---|---|
| | Bias | RMSE | Bias | RMSE | Bias | RMSE |
| Composite sample for whole field | −0.267 | 0.718 | −0.026 | 9.594 | −0.041 | 7.272 |
| gSSURGO estimate at each sample point | −0.207 | 0.887 | −12.274 | 19.362 | 0.555 | 12.336 |
| Scale gSSURGO by ratio of composite sample to composite gSSURGO | −0.201 | 0.741 | 0.751 | 22.469 | 0.093 | 8.371 |
| Linear regression of gSSURGO points | −0.000 | 0.758 | 0.107 | 13.796 | −0.218 | 11.182 |
| Linear regression of composite sample and gSSURGO points | −0.001 | 0.641 | 0.004 | 9.407 | −0.008 | 7.064 |
| Linear regression of Lasso-optimal predictors | −0.002 | 0.636 | 0.017 | 9.417 | 0.020 | 7.069 |
| Logit-transformed linear regression of composite samples and gSSURGO points | N/A | N/A | −0.408 | 9.491 | −1.575 | 9.490 |
| Decision Tree regression or composite sample + gSSURGO points | −0.001 | 0.563 | −0.026 | 10.495 | 0.001 | 7.405 |

Appendix A: Acronyms

IRP A program involving field trials and other research at Indigo™ Ag.
NED A national elevation dataset made by the USGS and other partners.
PTF Pedotransfer functions are predictive functions of certain soil properties using data from soil surveys. Most PTFs are developed to predict soil hydraulic properties such as hydraulic conductivity or water retention.
TPI Topographic Position Index compares the elevation of each cell in a DEM to the mean elevation of a specified neighborhood around that cell.
TRI The mean of the absolute differences between the value of a slope in a cell and the value of its 8 surrounding cells.

What is claimed is:

1. A method for estimating greenhouse gas emissions, the method comprising:
receiving a plurality of soil sample locations within a land area and regional soil data of the land area;
determining a plurality of pre-strata based on the plurality of soil sample locations and the regional soil data, wherein each pre-stratum of the plurality of pre-strata comprises a plurality of soil sample points across the land area;
for each pre-stratum of the plurality of pre-strata:
determining a potential for bias in an estimate of emissions reduction for the pre-stratum; and
when the potential for bias is above a predetermined threshold, determining a plurality of post-strata based on the pre-stratum; and
determining a total estimated emissions reduction of the land area based on the plurality of post-strata.

2. The method of claim 1, further comprising estimating soil organic carbon (SOC) emissions reduction of the land area, wherein estimating SOC emissions reduction comprises generating a plurality of simulations of SOC emissions reduction based on soil attributes of the land area.

3. The method of claim 2, wherein the plurality of simulations comprises Monte Carlo simulations.

4. The method of claim 2, wherein the soil attributes include a percent of SOC, soil texture, pH, and bulk density.

5. The method of claim 1, wherein the regional soil data comprises land management practices.

6. The method of claim 1, wherein the regional soil data comprises soil characteristics.

7. The method of claim 1, further comprising combining at least two of the plurality of pre-strata.

8. The method of claim 1, wherein determining the plurality of pre-strata comprises applying a zone attribute table and a point attribute table.

9. The method of claim 1, wherein determining the potential for bias comprises:
determining a first average value of an attribute among observed sample locations;
determining a second average value of the attribute among all locations where samples were planned to be taken;
determining a pooled standard deviation based on a variation associated with the attribute; and
labeling the pre-strata as likely including bias when a difference between the first and second average values, divided by the pooled standard deviation, is above a predetermined threshold.

10. The method of claim 1, wherein determining the plurality of post-strata further comprises:
partitioning the land area into a plurality of fields, each field comprising one or more soil sample locations of the plurality of soil sample locations; and binning the plurality of fields into a plurality of bins based on at least one variable.

11. The method of claim 10, wherein determining the plurality of post-strata further comprises applying one or more rules to the binned plurality of fields.

12. The method of claim 10, wherein the at least one variable comprises land management practices.

13. The method of claim 10, wherein the at least one variable comprises soil texture.

14. The method of claim 10, wherein the at least one variable comprises crop type.

15. The method of claim 10, wherein binning comprises applying clustering to the plurality of fields.

16. The method of claim 15, wherein clustering comprises k-means clustering.

17. The method of claim 10, wherein at least one of the plurality of fields includes at least one observed soil measurement at the one or more soil sample locations.

18. The method of claim 17, wherein at least one of the plurality of fields includes at least one missing soil measurements at the one or more soil sample locations.

19. The method of claim 18, wherein determining the total estimated emissions reduction comprises:
for each post-stratum of the plurality of post-strata:
determining a mean emissions reduction based on the at least one observed soil measurement in the plurality of fields within the post-stratum;
determining a total emissions reduction based on the mean emission reduction and a total area of the post-stratum; and
determining a variance of the total emissions reduction.

20. The method of claim 19, wherein determining the total estimated emissions reduction further comprises:
summing each total emissions reduction; and
summing each variance.

21. The method of claim 1, further comprising determining a potential for bias for each post-stratum in the plurality of post-strata.

22. A system comprising:
a soil sample location database;
a regional soil data database; and
a computing node comprising a computer readable storage medium having program instructions embodied therewith, the program instructions executable by a processor of the computing node to cause the processor to perform a method comprising:
receiving a plurality of soil sample locations within a land area from the soil sample location database and regional soil data of the land area from the regional soil data database;
determining a plurality of pre-strata based on the plurality of soil sample locations and the regional soil data, wherein each pre-stratum of the plurality of pre-strata comprises a plurality of soil sample points across the land area;
for each pre-stratum of the plurality of pre-strata:
determining a potential for bias in an estimate of emissions reduction for the pre-stratum; and
when the potential for bias is above a predetermined threshold, determining a plurality of post-strata based on the pre-stratum; and
determining a total estimated emissions reduction of the land area based on the plurality of post-strata.

23. A computer program product for estimating greenhouse gas emissions comprising a computer readable storage medium having program instructions embodied therewith, the program instructions executable by a processor to cause the processor to perform a method comprising:
receiving a plurality of soil sample locations within a land area and regional soil data of the land area;
determining a plurality of pre-strata based on the plurality of soil sample locations and the regional soil data, wherein each pre-stratum of the plurality of pre-strata comprises a plurality of soil sample points across the land area;
for each pre-stratum of the plurality of pre-strata:
determining a potential for bias in an estimate of emissions reduction for the pre-stratum; and
when the potential for bias is above a predetermined threshold, determining a plurality of post-strata based on the pre-stratum; and
determining a total estimated emissions reduction of the land area based on the plurality of post-strata.

* * * * *